US012616832B2

(12) United States Patent (10) Patent No.: US 12,616,832 B2
Willand et al. (45) Date of Patent: May 5, 2026

(54) SYSTEMS AND METHODS FOR DELIVERING NEUROREGENERATIVE THERAPY

(71) Applicant: Epineuron Technologies Inc., Mississauga (CA)

(72) Inventors: Michael Patrick Willand, Oakville (CA); Sergio David Aguirre, Bolton (CA)

(73) Assignee: Epineuron Technologies Inc., Mississauga (CA)

( * ) Notice: Subject to any disclaimer, the term of this patent is extended or adjusted under 35 U.S.C. 154(b) by 0 days.

(21) Appl. No.: 17/670,351

(22) Filed: Feb. 11, 2022

(65) Prior Publication Data

US 2022/0233849 A1 Jul. 28, 2022

Related U.S. Application Data

(63) Continuation of application No. 16/759,257, filed as application No. PCT/US2018/057375 on Oct. 24, 2018, now Pat. No. 11,247,045.

(60) Provisional application No. 62/683,019, filed on Jun. 11, 2018, provisional application No. 62/577,141, filed on Oct. 25, 2017.

(51) Int. Cl.
    *A61N 1/05* (2006.01)
    *A61N 1/36* (2006.01)
(52) U.S. Cl.
    CPC ....... *A61N 1/0556* (2013.01); *A61N 1/36125* (2013.01); *A61N 1/36171* (2013.01)
(58) Field of Classification Search
    CPC ............... A61N 1/0551; A61N 1/0556; A61N 1/36125; A61N 1/36146; A61N 1/36171; A61N 1/0502; A61N 1/0504; A61B 5/388

USPC .......................................................... 607/50
    See application file for complete search history.

(56) References Cited

U.S. PATENT DOCUMENTS

| | | |
|---|---|---|
| 3,664,329 A | 5/1972 | Naylor |
| 3,830,226 A | 8/1974 | Staub et al. |
| 4,423,732 A | 1/1984 | Tarjan et al. |
| 4,662,884 A | 5/1987 | Stensaas et al. |
| 4,715,381 A | 12/1987 | Moberg |

(Continued)

FOREIGN PATENT DOCUMENTS

| | | |
|---|---|---|
| CN | 106039600 A | 10/2016 |
| CN | 112601488 | 4/2021 |

(Continued)

OTHER PUBLICATIONS

Extended European Search Report for EP Application No. 18870935.6 which has the same applicant as the present application, dated Jul. 2021, in 8 pages.

(Continued)

*Primary Examiner* — Paula J Stice
(74) *Attorney, Agent, or Firm* — Knobbe, Martens, Olson & Bear, LLP

(57) ABSTRACT

Systems, devices and methods are disclosed for the treatment of injured peripheral nerves or other tissue using electrical stimulation. The systems can be used either in intraoperative or peri-operative settings and incorporate the use of either a plurality of monopolar electrodes with a patch used as return or a plurality of bipolar electrodes such as a cuff. The systems can provide hands-free delivery of electrical stimulation therapy over a predetermined set of time.

18 Claims, 56 Drawing Sheets

(56)                    References Cited

U.S. PATENT DOCUMENTS

| | | | |
|---|---|---|---|
| 4,774,967 A | 10/1988 | Zanakis et al. |
| 4,919,140 A | 4/1990 | Borgen et al. |
| 4,940,065 A | 7/1990 | Tanagho et al. |
| 4,979,511 A | 12/1990 | Terry, Jr. |
| 5,314,457 A | 5/1994 | Jeutter et al. |
| 5,344,438 A | 9/1994 | Testerman et al. |
| 5,433,735 A | 7/1995 | Zanakis et al. |
| 5,487,756 A | 1/1996 | Kallesoe et al. |
| 5,702,429 A | 12/1997 | King |
| 5,814,092 A | 9/1998 | King |
| 5,913,882 A | 6/1999 | King |
| 5,951,539 A | 9/1999 | Nita |
| 5,964,702 A | 10/1999 | Grill et al. |
| 6,188,931 B1 | 2/2001 | Holmström et al. |
| 6,270,460 B1 | 8/2001 | McCartan et al. |
| 6,292,697 B1 | 9/2001 | Roberts |
| 6,292,701 B1 | 9/2001 | Prass et al. |
| 6,312,392 B1 | 11/2001 | Herzon |
| 6,436,129 B1 | 8/2002 | Sharkey et al. |
| 6,600,956 B2 | 7/2003 | Maschino et al. |
| 6,926,669 B1 | 8/2005 | Stewart et al. |
| 6,937,904 B2 | 8/2005 | Richmond et al. |
| 6,941,171 B2 | 9/2005 | Mann et al. |
| 7,120,499 B2 | 10/2006 | Thrope et al. |
| 7,160,241 B1 | 1/2007 | Herbst |
| 7,239,918 B2 | 7/2007 | Strother et al. |
| 7,277,759 B2 | 10/2007 | Overstreet et al. |
| 7,283,867 B2 | 10/2007 | Strother et al. |
| D559,987 S | 1/2008 | Strother et al. |
| 7,326,181 B2 | 2/2008 | Katims |
| 7,343,202 B2 | 3/2008 | Mrva et al. |
| 7,349,743 B2 | 3/2008 | Tadlock |
| 7,376,467 B2 | 5/2008 | Thrope et al. |
| 7,392,093 B2 | 6/2008 | Khan |
| D581,530 S | 11/2008 | Thierfelder et al. |
| 7,450,992 B1 | 11/2008 | Cameron |
| 7,483,734 B2 | 1/2009 | Colthurst |
| 7,544,171 B2 | 6/2009 | Schaden et al. |
| 7,571,002 B2 | 8/2009 | Thrope et al. |
| 7,676,271 B2 | 3/2010 | Wahlstrand et al. |
| 7,797,058 B2 | 9/2010 | Mrva et al. |
| 7,822,486 B2 | 10/2010 | Foster et al. |
| 7,848,812 B2 | 12/2010 | Crowley et al. |
| 7,878,981 B2 | 2/2011 | Strother et al. |
| 7,896,815 B2 | 3/2011 | Thrope et al. |
| 7,917,230 B2 | 3/2011 | Bly |
| 7,957,796 B2 | 6/2011 | Maschino |
| 7,957,817 B1 | 6/2011 | Gillespie et al. |
| 7,996,092 B2 | 8/2011 | Mrva et al. |
| 8,065,014 B2 | 11/2011 | Zealear |
| 8,079,865 B1 | 12/2011 | Rundle |
| 8,086,318 B2 | 12/2011 | Strother et al. |
| 8,116,882 B2 | 2/2012 | Kowalczewski |
| D658,304 S | 4/2012 | Rundle et al. |
| 8,172,768 B2 | 5/2012 | Strother et al. |
| 8,231,402 B2 | 7/2012 | Rundle |
| D665,085 S | 8/2012 | Strother et al. |
| D674,105 S | 1/2013 | Rundle et al. |
| 8,357,006 B2 | 1/2013 | Rundle |
| D683,320 S | 5/2013 | Strother et al. |
| 8,463,383 B2 | 6/2013 | Sakai et al. |
| 8,478,428 B2 | 7/2013 | Cowley |
| 8,494,625 B2 | 7/2013 | Hargrove |
| 8,500,652 B2 | 8/2013 | Strother et al. |
| 8,515,520 B2 | 8/2013 | Brunnett et al. |
| D696,404 S | 12/2013 | Golnik |
| 8,606,368 B2 | 12/2013 | Udo |
| 8,612,025 B2 | 12/2013 | Neisz et al. |
| 8,616,913 B2 | 12/2013 | Rundle |
| 8,626,302 B2 | 1/2014 | Bennett et al. |
| 8,660,646 B2 | 2/2014 | Laing et al. |
| 8,676,334 B2 | 3/2014 | Youn et al. |
| 8,700,177 B2 | 4/2014 | Strother et al. |
| 8,818,520 B2 | 8/2014 | Laing et al. |
| 8,880,189 B2 | 11/2014 | Lipani |
| 8,886,337 B2 | 11/2014 | Bennett et al. |
| 8,929,998 B2 | 1/2015 | Burgher et al. |
| 8,954,153 B2 | 2/2015 | Boggs, II |
| 8,965,499 B2 | 2/2015 | Cowley et al. |
| 8,965,516 B2 | 2/2015 | Bennett et al. |
| 8,989,855 B2 | 3/2015 | Murphy et al. |
| 8,989,859 B2 | 3/2015 | Deem et al. |
| D734,468 S | 7/2015 | Murakami |
| 9,076,187 B1 | 7/2015 | Laing et al. |
| 9,084,551 B2 | 7/2015 | Brunnett et al. |
| 9,089,708 B2 | 7/2015 | Grill et al. |
| 9,114,250 B2 | 8/2015 | True et al. |
| 9,138,579 B2 | 9/2015 | Wolpaw et al. |
| 9,227,053 B2 | 1/2016 | Bonde et al. |
| 9,245,265 B2 | 1/2016 | Laing et al. |
| 9,283,031 B2 | 3/2016 | Janssen et al. |
| 9,283,379 B2 | 3/2016 | True et al. |
| 9,339,643 B1 | 5/2016 | Moffitt et al. |
| 9,339,647 B2 | 5/2016 | Strother et al. |
| 9,345,538 B2 | 5/2016 | Deem et al. |
| 9,352,146 B2 | 5/2016 | Langhals et al. |
| 9,381,343 B2 | 7/2016 | Bennett et al. |
| 9,387,338 B2 * | 7/2016 | Burnett ................. A61N 2/008 |
| 9,399,134 B2 | 7/2016 | Simon et al. |
| 9,486,630 B2 | 11/2016 | Litvak et al. |
| 9,486,632 B2 | 11/2016 | Saab |
| 9,498,633 B2 | 11/2016 | Laing et al. |
| 9,550,061 B2 | 1/2017 | Litvak et al. |
| 9,555,245 B2 | 1/2017 | Boggs, II et al. |
| 9,630,011 B2 | 4/2017 | Lipani |
| 9,693,817 B2 | 7/2017 | Mehta et al. |
| 9,770,280 B2 | 9/2017 | Diederich et al. |
| 9,776,000 B2 | 10/2017 | Litvak et al. |
| 9,789,313 B2 | 10/2017 | Lipani |
| 9,802,051 B2 | 10/2017 | Mathur et al. |
| 9,821,163 B2 | 11/2017 | Fraga Da Silva et al. |
| 9,827,412 B2 | 11/2017 | Bennett et al. |
| 9,827,419 B2 | 11/2017 | Boggs, II et al. |
| 9,861,810 B2 | 1/2018 | Anikeeva et al. |
| 9,950,164 B2 | 4/2018 | Lipani |
| 9,956,393 B2 | 5/2018 | Perez et al. |
| 10,029,101 B2 | 7/2018 | Bennet et al. |
| 10,118,035 B2 | 11/2018 | Perez et al. |
| 10,118,037 B2 | 11/2018 | Kaula et al. |
| 10,143,840 B2 | 12/2018 | Perez et al. |
| 10,154,792 B2 | 12/2018 | Sakai et al. |
| 10,166,384 B2 | 1/2019 | Bennett et al. |
| 10,335,302 B2 | 7/2019 | Perez et al. |
| 10,376,145 B2 | 8/2019 | Perez et al. |
| 10,376,704 B2 | 8/2019 | Mathur et al. |
| 10,433,785 B2 | 10/2019 | Hausman et al. |
| 10,470,678 B2 | 11/2019 | Strother et al. |
| 10,589,089 B2 | 3/2020 | Willand et al. |
| 11,247,043 B2 | 2/2022 | Willand et al. |
| 11,247,044 B2 | 2/2022 | Willand et al. |
| 11,247,045 B2 | 2/2022 | Willand et al. |
| 11,344,250 B2 | 5/2022 | Hausman et al. |
| 11,364,381 B2 | 6/2022 | Willand et al. |
| D956,987 S | 7/2022 | Lewis et al. |
| D1,011,533 S | 1/2024 | Xia |
| 11,872,401 B2 * | 1/2024 | Scanlan ............ A61N 1/36167 |
| D1,021,823 S | 4/2024 | Zou |
| D1,023,325 S | 4/2024 | Aguiar |
| D1,055,283 S | 12/2024 | Lewis et al. |
| 12,232,944 B2 | 2/2025 | Dekeyser et al. |
| D1,075,015 S | 5/2025 | Xia |
| 12,311,178 B2 | 5/2025 | Scanlan et al. |
| 12,318,608 B2 | 6/2025 | Willand et al. |
| D1,098,461 S | 10/2025 | Walker et al. |
| 2002/0065544 A1 | 5/2002 | Smits |
| 2002/0120309 A1 | 8/2002 | Richmond et al. |
| 2003/0088274 A1 | 5/2003 | Gliner et al. |
| 2003/0225331 A1 | 12/2003 | Diederich et al. |
| 2003/0233137 A1 | 12/2003 | Edward |
| 2005/0085743 A1 | 4/2005 | Hacker et al. |
| 2005/0182455 A1 | 8/2005 | Thrope et al. |
| 2005/0182457 A1 | 8/2005 | Thrope et al. |
| 2005/0277844 A1 | 12/2005 | Strother et al. |
| 2005/0277999 A1 | 12/2005 | Strother et al. |

(56)                    References Cited

U.S. PATENT DOCUMENTS

| | | |
|---|---|---|
| 2006/0004429 A1 | 1/2006 | Mrva et al. |
| 2006/0025702 A1 | 2/2006 | Sterrantino et al. |
| 2006/0030919 A1 | 2/2006 | Mrva et al. |
| 2006/0041295 A1 | 2/2006 | Osypka |
| 2006/0149345 A1 | 7/2006 | Boggs, II et al. |
| 2006/0173507 A1 | 8/2006 | Mrva et al. |
| 2006/0194724 A1 | 8/2006 | Whitehurst et al. |
| 2006/0200207 A1 | 9/2006 | Thrope et al. |
| 2006/0200219 A1 | 9/2006 | Thrope et al. |
| 2007/0032836 A1 | 2/2007 | Thrope et al. |
| 2007/0032837 A1 | 2/2007 | Thrope et al. |
| 2007/0060955 A1 | 3/2007 | Strother et al. |
| 2007/0060967 A1 | 3/2007 | Strother et al. |
| 2007/0060968 A1 | 3/2007 | Strother et al. |
| 2007/0060979 A1 | 3/2007 | Strother et al. |
| 2007/0060980 A1 | 3/2007 | Strother et al. |
| 2007/0066995 A1 | 3/2007 | Strother et al. |
| 2007/0067000 A1 | 3/2007 | Strother et al. |
| 2007/0088406 A1 | 4/2007 | Bennett et al. |
| 2007/0123952 A1 | 5/2007 | Strother et al. |
| 2007/0191915 A1 | 8/2007 | Strother et al. |
| 2007/0239224 A1 | 10/2007 | Bennett et al. |
| 2007/0250036 A1 | 10/2007 | Volk |
| 2007/0270921 A1 | 11/2007 | Strother et al. |
| 2007/0293910 A1 | 12/2007 | Strother et al. |
| 2007/0299483 A1 | 12/2007 | Strother et al. |
| 2008/0033500 A1 | 2/2008 | Strother et al. |
| 2008/0051647 A1 | 2/2008 | Wu et al. |
| 2008/0065167 A1 | 3/2008 | Boggs, II et al. |
| 2008/0065182 A1 | 3/2008 | Strother et al. |
| 2008/0071321 A1 | 3/2008 | Boggs, II et al. |
| 2008/0071322 A1 | 3/2008 | Mrva et al. |
| 2008/0132969 A1 | 6/2008 | Bennett et al. |
| 2008/0132974 A1 | 6/2008 | Strother et al. |
| 2008/0154335 A1 | 6/2008 | Thrope et al. |
| 2008/0161874 A1 | 7/2008 | Bennett et al. |
| 2008/0172116 A1 | 7/2008 | Mrva et al. |
| 2008/0208280 A1 | 8/2008 | Lindenthaler et al. |
| 2008/0249595 A1 | 10/2008 | McDaniel |
| 2008/0269716 A1* | 10/2008 | Bonde ................ A61B 17/3468 |
| | | 607/118 |
| 2008/0300654 A1 | 12/2008 | Lambert et al. |
| 2008/0300657 A1 | 12/2008 | Stultz |
| 2009/0062896 A1 | 3/2009 | Overstreet et al. |
| 2009/0132003 A1 | 5/2009 | Borgens et al. |
| 2010/0036445 A1 | 2/2010 | Sakai et al. |
| 2010/0036454 A1 | 2/2010 | Bennett et al. |
| 2010/0100158 A1 | 4/2010 | Thrope et al. |
| 2010/0137938 A1 | 6/2010 | Kishawi |
| 2010/0152808 A1 | 6/2010 | Boggs, II |
| 2010/0152809 A1 | 6/2010 | Boggs, II |
| 2010/0152811 A1 | 6/2010 | Flaherty |
| 2010/0152812 A1 | 6/2010 | Flaherty et al. |
| 2010/0222844 A1 | 9/2010 | Troosters et al. |
| 2010/0274310 A1 | 10/2010 | Boggs, II et al. |
| 2010/0280584 A1 | 11/2010 | Johnson et al. |
| 2010/0298920 A1 | 11/2010 | Mrva et al. |
| 2010/0317956 A1 | 12/2010 | Kartush |
| 2011/0054346 A1 | 3/2011 | Hausman et al. |
| 2011/0060238 A1 | 3/2011 | Hausman et al. |
| 2011/0060242 A1 | 3/2011 | Hausman et al. |
| 2011/0060243 A1 | 3/2011 | Hausman et al. |
| 2011/0093032 A1 | 4/2011 | Boggs, II et al. |
| 2011/0125051 A1 | 5/2011 | Strother et al. |
| 2011/0257701 A1 | 10/2011 | Strother et al. |
| 2012/0142228 A1 | 6/2012 | Rundle |
| 2012/0238902 A1 | 9/2012 | Strother et al. |
| 2012/0291271 A1 | 11/2012 | Rundle |
| 2012/0296442 A1 | 11/2012 | Hausman |
| 2012/0323294 A1 | 12/2012 | Laing et al. |
| 2013/0018445 A1 | 1/2013 | Sakai et al. |
| 2013/0096641 A1 | 4/2013 | Strother et al. |
| 2013/0131753 A1 | 5/2013 | Simon et al. |
| 2013/0137288 A1 | 5/2013 | Rundle |
| 2013/0197615 A1 | 8/2013 | Rundle et al. |
| 2013/0204315 A1 | 8/2013 | Wongsarnpigoon et al. |
| 2013/0231715 A1 | 9/2013 | Grill, Jr. et al. |
| 2013/0245490 A1 | 9/2013 | Strother et al. |
| 2013/0296733 A1 | 11/2013 | Strother et al. |
| 2013/0303876 A1 | 11/2013 | Gelfand et al. |
| 2013/0317588 A1 | 11/2013 | Howard et al. |
| 2013/0338749 A1 | 12/2013 | Brunnett et al. |
| 2014/0058495 A1 | 2/2014 | Sakai et al. |
| 2014/0073985 A1 | 3/2014 | Sakai et al. |
| 2014/0081244 A1 | 3/2014 | Voeller et al. |
| 2014/0081353 A1 | 3/2014 | Cook et al. |
| 2014/0121741 A1 | 5/2014 | Bennett et al. |
| 2014/0194771 A1 | 7/2014 | Parker et al. |
| 2014/0194772 A1 | 7/2014 | Single et al. |
| 2014/0194948 A1 | 7/2014 | Strother et al. |
| 2014/0214129 A1 | 7/2014 | Waataja et al. |
| 2014/0214135 A1 | 7/2014 | Ben-David et al. |
| 2014/0236257 A1 | 8/2014 | Parker et al. |
| 2014/0243931 A1 | 8/2014 | Parker et al. |
| 2014/0277315 A1 | 9/2014 | Hanson et al. |
| 2014/0288613 A1 | 9/2014 | Laing et al. |
| 2014/0371622 A1 | 12/2014 | Hausman et al. |
| 2015/0032022 A1 | 1/2015 | Stone et al. |
| 2015/0099936 A1 | 4/2015 | Burdulis |
| 2015/0313512 A1 | 11/2015 | Hausman et al. |
| 2015/0335887 A1 | 11/2015 | Riddle et al. |
| 2016/0038072 A1 | 2/2016 | Brown et al. |
| 2016/0038074 A1 | 2/2016 | Brown et al. |
| 2016/0045745 A1 | 2/2016 | Mathur et al. |
| 2016/0158550 A1 | 6/2016 | Hou |
| 2016/0250466 A1 | 9/2016 | Boggs, II et al. |
| 2017/0239483 A1 | 8/2017 | Mathur et al. |
| 2017/0266443 A1* | 9/2017 | Rajguru ............. A61N 1/36034 |
| 2017/0281945 A1* | 10/2017 | Gill .................... A61N 1/36164 |
| 2017/0312499 A1 | 11/2017 | Linker et al. |
| 2018/0064484 A1 | 3/2018 | Diederich et al. |
| 2018/0078754 A1 | 3/2018 | Perez et al. |
| 2018/0078763 A1 | 3/2018 | Boggs, II et al. |
| 2018/0085580 A1 | 3/2018 | Perez et al. |
| 2018/0117344 A1 | 5/2018 | Mathur et al. |
| 2018/0338765 A1 | 11/2018 | Judy et al. |
| 2019/0110705 A1 | 4/2019 | Sakai et al. |
| 2019/0151660 A1 | 5/2019 | Boggs, II et al. |
| 2019/0217089 A1 | 7/2019 | Bayat et al. |
| 2019/0247652 A1 | 8/2019 | Boggs, II et al. |
| 2019/0255339 A1 | 8/2019 | Lee et al. |
| 2019/0275325 A1 | 9/2019 | Walter et al. |
| 2020/0069202 A1 | 3/2020 | Strother et al. |
| 2020/0155798 A1 | 5/2020 | Yang et al. |
| 2021/0001128 A1 | 1/2021 | Patnala et al. |
| 2021/0101011 A1 | 4/2021 | Scanlan et al. |
| 2021/0146121 A1* | 5/2021 | Scanlan ............. A61N 1/36167 |
| 2021/0283399 A1 | 9/2021 | Willand et al. |
| 2021/0386994 A1 | 12/2021 | Scanlan et al. |
| 2022/0161025 A1 | 5/2022 | Willand et al. |
| 2022/0241584 A1 | 8/2022 | Willand et al. |
| 2022/0287566 A1 | 9/2022 | Strother et al. |
| 2022/0313984 A1 | 10/2022 | Willand et al. |
| 2023/0077370 A1 | 3/2023 | Hausman et al. |
| 2024/0099632 A1 | 3/2024 | Cottrill et al. |
| 2024/0238004 A1 | 7/2024 | Lewis et al. |
| 2025/0281751 A1 | 9/2025 | Scanlan et al. |
| 2025/0288798 A1 | 9/2025 | Willand et al. |

FOREIGN PATENT DOCUMENTS

| | | |
|---|---|---|
| DE | 102007036862 | 2/2009 |
| GB | 2423020 | 8/2006 |
| GB | 2423022 | 8/2006 |
| JP | 2002-113115 | 4/2002 |
| JP | 2010-514477 | 5/2010 |
| JP | 2010-515487 | 5/2010 |
| JP | 2013-534175 | 9/2013 |
| WO | WO 2008/002917 | 1/2008 |
| WO | WO 2008/005843 | 1/2008 |
| WO | WO 2009/130515 | 10/2009 |
| WO | WO 2010/077494 | 7/2010 |
| WO | WO 2011/139779 | 11/2011 |
| WO | WO 2013/036630 | 3/2013 |

(56) References Cited

FOREIGN PATENT DOCUMENTS

| WO | WO 2013/067018 | 5/2013 |
|----|----------------|--------|
| WO | WO 2013/106884 | 7/2013 |
| WO | WO 2013/138786 | 9/2013 |
| WO | WO 2014/113813 | 7/2014 |
| WO | WO 2016/025909 | 2/2016 |
| WO | WO 2016/025910 | 2/2016 |
| WO | WO 2016/025912 | 2/2016 |
| WO | WO 2016/025913 | 2/2016 |
| WO | WO 2016/025915 | 2/2016 |
| WO | WO 2016/112398 | 7/2016 |
| WO | WO 2016/112400 | 7/2016 |
| WO | WO 2016/112401 | 7/2016 |
| WO | WO 2016/125250 | 8/2016 |
| WO | WO 2016/183689 | 11/2016 |
| WO | WO 2017/011305 | 1/2017 |
| WO | WO 2017/064500 | 4/2017 |
| WO | WO 2017/139784 | 8/2017 |
| WO | WO 2018/048954 | 3/2018 |
| WO | WO 2018/237278 | 12/2018 |
| WO | WO 2019/084182 | 5/2019 |
| WO | WO 2019/103917 | 5/2019 |
| WO | WO 2019/165108 | 8/2019 |
| WO | WO 2020/097500 | 5/2020 |
| WO | WO 2021/067498 | 4/2021 |
| WO | WO 2022/119912 | 6/2022 |
| WO | WO 2025/166078 | 8/2025 |

OTHER PUBLICATIONS

Extended European Search Report for EP Application No. 20871120.0, which has the same applicant as the present application, dated Sep. 2023, in 9 pages.

U.S. Appl. No. 16/553,043 (U.S. Pat. No. 10,589,089), filed Aug. 27, 2019, Systems and Methods for Delivering Neuroregenerative Therapy.

U.S. Appl. No. 16/687,576 (U.S. Pat. No. 11,247,044), filed Nov. 18, 2019, Devices for Delivering Neuroregenerative Therapy.

U.S. Appl. No. 17/670,323, filed Feb. 11, 2022, Devices and Methods for Delivering Neuroregenerative Therapy.

U.S. Appl. No. 16/759,257 (U.S. Pat. No. 11,247,045), filed Apr. 24, 2020, Systems and Methods for Delivering Neuroregenerative Therapy.

U.S. Appl. No. 17/670,351 (present application), filed Feb. 11, 2022, Systems and Methods for Delivering Neuroregenerative Therapy.

U.S. Appl. No. 17/335,045 (U.S. Pat. No. 11,247,043), filed May 31, 2021, Electrode Interface Devices for Delivery of Neuroregenerative Therapy.

U.S. Appl. No. 17/670,377, filed Feb. 11, 2022, Electrode Interface Devices for Delivery of Neuroregenerative Therapy.

U.S. Appl. No. 17/335,056 (U.S. Pat. No. 11,364,381), filed May 31, 2021, Methods for Delivering Neuroregenerative Therapy and Reducing Post-Operative and Chronic Pain.

U.S. Appl. No. 17/842,650, filed Jun. 16, 2022, Systems and Methods for Acute and Chronic Pain Management.

U.S. Appl. No. 29/831,001, filed Mar. 16, 2022, Stimulation Device.

International Search Report and Written Opinion for PCT appl. PCT/US2018/057375 dated Jan. 11, 2019.

International Search Report and Written Opinion for PCT appl. PCT/US20/53630 dated Feb. 19, 2021.

International Search Report and Written Opinion for PCT appl. PCT/US2025/013890 dated May 26, 2025.

Adams et al., "Computational modeling of neurons: intensity-duration relationship of extracellular electrical stimulation for changes in intracellular calcium," Journal of Neurophysiology, vol. 115(1), pp. 602-616 (2016).

Ahlborn et al., "One hour electrical stimulation accelerates functional recovery after femoral nerve repair," Exp. Neurol., vol. 208, pp. 137-144 (2007).

Al-Majed et al., "Brief electrical stimulation promotes the speed and accuracy of motor axonal regeneration," J. Neurosci., vol. 20, pp. 2602-2608 (2000).

Al-Majed et al., "Electrical stimulation accelerates and enhances expression of regeneration- associated genes in regenerating rat femoral motoneurons," Cell. Mol. Neurobiol., vol. 24(3), pp. 379-402 (Jun. 2004).

Al-Majed et al., "Electrical stimulation accelerates and increases expression of BDNF and trkB mRNA in regenerating rat femoral motoneurons," Eur. J. Neurosci., vol. 12, pp. 4381-4390 (2000).

Alrashdan et al., "Thirty minutes of low intensity electrical stimulation promotes nerve regeneration after sciatic nerve crush injury in a rat model," Acta. Neurol. Belg., vol. 110(2), pp. 168-179 (Jun. 2010).

Asensio-Pinilla et al., "Electrical stimulation combined with exercise increase axonal regeneration after peripheral nerve injury," Exp. Neurol., vol. 219(1), pp. 258-265 (Sep. 2009).

Balog et al., "Electrical stimulation for neuroregeneration in urology: a new therapeutic paradigm," Current Opinion in Urology, vol. 29(4), pp. 458-465 (Jul. 2019).

Baptista et al., "High- and low-frequency transcutaneous electrical nerve stimulation delay sciatic nerve regeneration after crush lesion in the mouse," Journal of the Peripheral Nervous System, vol. 13(1), pp. 71-80 (Mar. 1, 2008).

Barber et al., "Intraoperative Brief Electrical Stimulation of the Spinal Accessory Nerve (Best Spin) for prevention of shoulder dysfunction after oncologic neck dissection: a double-blinded, randomized controlled trial," Journal of Otolaryngology - Head & Neck Surgery, vol. 47, p. 7 (Jan. 23, 2018).

Brushart et al., "Electrical Stimulation Promotes Motoneuron Regeneration without Increasing Its Speed or Conditioning the Neuron," J. Neurosci., vol. 22(15), pp. 6631-6638 (Aug. 1, 2002).

Brushart et al., "Electrical stimulation restores the specificity of sensory axon regeneration," Exp. Neurol., vol. 194(1), pp. 221-229 (Jul. 2005).

Calvey et al., "Short-Term Electrical Stimulation to Promote Nerve Repair and Functional Recovery in a Rat Model," The Journal of Hand Surgery, vol. 40(2), pp. 314-322 (Feb. 2015).

Cavalcante Miranda De Assis et al., "The Parameters of Transcutaneous Electrical Nerve Stimulation Are Critical to Its Regenerative Effects When Applied Just after a Sciatic Crush Lesion in Mice," BioMed Research International, vol. 2014, pp. 1-8 (2014).

Chen et al., "Effects of percutaneous electrical stimulation on peripheral nerve regeneration using silicone rubber chambers," J. Biomed. Mater. Res., vol. 57(4), pp. 541-549 (Dec. 15, 2001).

Cheng et al., "The Effects of Different Electrical Stimulation Protocols on Nerve Regeneration Through Silicone Conduits," Journal of Trauma-Injury Infection, vol. 56(6), pp. 1241-1246 (2004).

Cobianchi et al., "Differential effects of activity dependent treatments on axonal regeneration and neuropathic pain after peripheral nerve injury," Experimental Neurology, vol. 240, pp. 157-167 (Feb. 2013).

Deng et al., "Daily bilateral pudendal nerve electrical stimulation improves recovery from stress urinary incontinence," Interface Focus, vol. 9(4), p. 20190020 (Aug. 6, 2019).

Eberhardt et al., "BDNF/TrkB signaling regulates HNK-1 carbohydrate expression in regenerating motor nerves and promotes functional recovery after peripheral nerve repair," Exp. Neurol., vol. 198, pp. 500-510 (2006).

Elzinga et al., "Brief electrical stimulation improves nerve regeneration after delayed repair in Sprague Dawley rats," Experimental Neurology, vol. 269, pp. 142-153 (Jul. 2015).

English et al., "Electrical stimulation promotes peripheral axon regeneration by enhanced neuronal neurotrophin signaling," Devel. Neurobio., vol. 67(2), pp. 158-172 (Feb. 1, 2007).

English, A., "Enhancing axon regeneration in peripheral nerves also increases functionally inappropriate reinnervation of targets," The Journal of Comparative Neurology, vol. 490(4), pp. 427-441 (2005).

Foecking et al., "Single session of brief electrical stimulation immediately following crush injury enhances functional recovery of rat facial nerve," J. Rehabil. Res. Dev., vol. 49(3), pp. 451-458 (2012).

(56) References Cited

OTHER PUBLICATIONS

Geremia et al., "Electrical stimulation promotes sensory neuron regeneration and growth-associated gene expression," Exp. Neurol., vol. 205, pp. 347-359 (2007).

Gordon et al., "Augmenting nerve regeneration with electrical stimulation," Neurol. Res., vol. 30, pp. 1012-1022 (2008).

Gordon et al., "Brief electrical stimulation accelerates axon regeneration in the peripheral nervous system and promotes sensory axon regeneration in the central nervous system," Motor Control, vol. 13(4), pp. 412-441 (Oct. 2009).

Gordon et al., "Brief post-surgical electrical stimulation accelerates axon regeneration and muscle reinnervation without affecting the functional measures in carpal tunnel syndrome patients," Exp. Neurol., vol. 223(1), pp. 192-202 (May 2010).

Gordon et al., "Chapter 24 Electrical Stimulation for Improving Nerve Regeneration: Where do we Stand?" International Review of Neurobiology, vol. 87, pp. 433-444 (2009).

Gordon et al., "Experimental strategies to promote functional recovery after peripheral nerve injuries," J. Peripher. Nerv. Syst., vol. 8, pp. 236-250 (2003).

Gordon, T., "Electrical Stimulation to Enhance Axon Regeneration After Peripheral Nerve Injuries in Animal Models and Humans," Neurotherapeutics, vol. 13(2), pp. 295-310 (Jan. 11, 2016).

Haastert-Talini et al., "Electrical stimulation accelerates axonal and functional peripheral nerve regeneration across long gaps," J. Neurotrauma, vol. 28(4), pp. 661-674 (Apr. 2011).

Haastert-Talini et al., "Electrical Stimulation for Promoting Peripheral Nerve Regeneration," International Review of Neurobiology, vol. 109(), pp. 111-124 (2013).

Hamilton et al., "Misdirection of regenerating axons and functional recovery following sciatic nerve injury in rats," The Journal of Comparative Neurology, vol. 519(1), pp. 21-33 (2011).

Huang et al., "Electrical stimulation accelerates motor functional recovery in the rat model of 15-mm sciatic nerve gap bridged by scaffolds with longitudinally oriented microchannels," Neurorehabil. Neural Repair, vol. 24(8), pp. 736-745 (Oct. 2010).

Huang et al., "Electrical stimulation accelerates motor functional recovery in autograft-repaired 10 mm femoral nerve gap in rats," J. Neurotrauma, vol. 26(10), pp. 1805-1813 (Oct. 2009).

Huang et al., "Electrical stimulation accelerates nerve regeneration and functional recovery in delayed peripheral nerve injury in rats," Eur. J. Neurosci., vol. 38(12), pp. 3691-3701 (Dec. 1, 2013).

Huang et al., "Electrical stimulation induces calcium-dependent release of NGF from cultured Schwann cells," Glia, vol. 58(5), pp. 622-631 (2010).

Huang et al., "Electrical Stimulation to Conductive Scaffold Promotes Axonal Regeneration and Remyelination in a Rat Model of Large Nerve Defect," Plos One, vol. 7(6), page e39526 (Jun. 21, 2012).

Jo et al., "Comparing electrical stimulation and tacrolimus (FK506) to enhance treating nerve injuries," Muscle & Nerve, vol. 60(5), pp. 629-636 (Nov. 1, 2019).

Kerns et al., "Electrical field effects on crushed nerve regeneration," Exp. Neurol., vol. 117(1), pp. 71-80 (Jul. 1992).

Kim et al., "Subthreshold continuous electrical stimulation facilitates functional recovery of facial nerve after crush injury in rabbit," Muscle Nerve, vol. 43(2), pp. 251-258 (Feb. 1, 2011).

Kim et al., "The effect of subthreshold continuous electrical stimulation on the facial function of patients with Bell's palsy," Acta Oto-Laryngologica, vol. 136(1), pp. 100-105 (Jan. 2, 2016).

Koo et al., "Wireless bioresorbable electronic system enables sustained nonpharmacological neuroregenerative therapy," Nature Medicine, p. 1 (Oct. 8, 2018).

Lal et al., "Electrical stimulation facilitates rat facial nerve recovery from a crush injury," Otolaryngol. Head Neck Surg., vol. 139(1), pp. 68-73 (Jul. 2008).

Lee et al., "Functional regeneration of a severed peripheral nerve with a 7-mm gap in rats through the use of an implantable electrical stimulator and a conduit electrode with collagen coating," Neuromodulation, vol. 13(4), pp. 299-304 (Oct. 2010).

Lee et al., "Functional regeneration of severed peripheral nerve using an implantable electrical stimulator," Conf. Proc. IEEE Eng. Med Biol. Soc. 2010, pp. 1511-1514 (2010).

Liss et al., "Electric stimulation of a transsected nerve does not seem to prevent loss of sensory neurons: an experimental study in cats," Scand. J. Plast. Reconstr. Surg. Hand. Surg., vol. 33(4), pp. 403-409 (Dec. 1999).

Longo et al., "Electromagnetic fields influence NGF activity and levels following sciatic nerve transection," J. Neurosci. Res., vol. 55(2), pp. 230-237 (Jan. 15, 1999).

López-Álavrez et al., "Chronic electrical stimulation reduces hyperalgesia and associated spinal changes induced by peripheral nerve injury," Neuromodulation (Feb. 20, 2019).

Lu et al., "Effects of electrical stimulation at different frequencies on regeneration of transected peripheral nerve," Neurorehabil. Neural Repair, vol. 22(4), pp. 367-373 (Aug. 2008).

Lu et al., "Use of Electrical Stimulation at Different Current Levels to Promote Recovery After Peripheral Nerve Injury in Rats," The Journal of Trauma: Injury, Infection, and Critical Care, vol. 67(5), pp. 1066-1072 (Nov. 1, 2009).

Macewan et al., "Therapeutic electrical stimulation of injured peripheral nerve tissue using implantable thin-film wireless nerve stimulators," Journal of Neurosurgery, pp. 1-10 (Feb. 9, 2018).

McCaig et al., "Electrical fields, nerve growth and nerve regeneration," Exp. Physiol., vol. 76(4), pp. 473-494 (Jul. 1, 1991).

McLean et al., "Delayed Nerve Stimulation Promotes Axon-Protective Neurofilament Phosphorylation, Accelerates Immune Cell Clearance and Enhances Remyelination In Vivo in Focally Demyelinated Nerves," PLOS One, vol. 9(10), page e110174 (Oct. 13, 2014).

Mendez et al., "Brief electrical stimulation after facial nerve transection and neurorrhaphy: a randomized prospective animal study," Journal of Otolaryngology - Head & Neck Surgery, vol. 45, p. 7 (Feb. 1, 2016).

Nix et al., "Electrical stimulation of regenerating nerve and its effect on motor recovery," Brain Res., vol. 272(1), pp. 21-25 (Aug. 1, 1983).

Park et al., "Effects of Repeated 20-Hz Electrical Stimulation on Functional Recovery Following Peripheral Nerve Injury," Neurorehabil. Neural Repair (Jul. 2019).

Peripulse, epineurontech.com, [online], [site visited Sep. 6, 2025], Available from internetIURL:https://www.epineurontech.com/peripulse (Year: 2025) - reference made of record by USPTO in U.S. Appl. No. 29/831,001, filed Mar. 16, 2022.

Pockett et al., "Acceleration of peripheral nerve regeneration after crush injury in rat," Neurosci. Lett., vol. 59(2), pp. 221-224 (Aug. 30, 1985).

Power et al., "Postsurgical Electrical Stimulation Enhances Recovery Following Surgery for Severe Cubital Tunnel Syndrome: A Double-Blind Randomized Controlled Trial," Neurosurgery (Aug. 20, 2019).

Rui, B., "An implantable electrical stimulator used for peripheral nerve rehabilitation in rats," Experimental and Therapeutic Medicine, vol. 6(1), pp. 22-28 (May 13, 2013).

Senger et al., "Conditioning electrical stimulation promotes functional nerve regeneration," Exp. Neurol., vol. 315, pp. 60-71 (May 2019).

Senger et al., "Electrical stimulation as a conditioning strategy for promoting and accelerating peripheral nerve regeneration," Experimental Neurology, vol. 302, pp. 75-84 (Apr. 1, 2018).

Shapira et al., "Brief Electrical Stimulation Promotes Nerve Regeneration Following Experimental In- Continuity Nerve Injury," Neurosurgery, vol. 85(1), pp. 156-163 (Jun. 11, 2018).

Singh et al., "Accelerated axon outgrowth, guidance, and target reinnervation across nerve transection gaps following a brief electrical stimulation paradigm," J. Neurosurg., vol. 116(3), pp. 498-512 (Mar. 2012).

Sobotka et al., "Intraoperative 1-Hour Electrical Nerve Stimulation Enhances Outcomes of Nerve- Muscle-Endplate Band Grafting Technique for Muscle Reinnervation," Journal of Reconstructive Microsurgery, vol. 33(8), pp. 533-543 (Oct. 2017).

(56)                    References Cited

OTHER PUBLICATIONS

Su et al., "Late administration of high-frequency electrical stimulation increases nerve regeneration without aggravating neuropathic pain in a nerve crush injury," BMC Neuroscience, vol. 19, p. 37 (Jun. 25, 2018).

Tang et al., "Direct electrical stimulation on the injured ulnar nerve using acupuncture needles combined with rehabilitation accelerates nerve regeneration and functional recovery - A case report," Complementary Therapies in Medicine, vol. 24, pp. 103-107 (Feb. 2016).

Udina et al., "Electrical stimulation of intact peripheral sensory axons in rats promotes outgrowth of their central projections," Experimental Neurology, vol. 210(1), pp. 238-247 (Mar. 2008).

Udina et al., "Rolipram-induced elevation of CAMP or chondroitinase ABC breakdown of inhibitory proteoglycans in the extracellular matrix promotes peripheral nerve regeneration," Exp. Neurol., vol. 223(1), pp. 143-152 (May 2010).

Vivó et al., "Immediate electrical stimulation enhances regeneration and reinnervation and modulates spinal plastic changes after sciatic nerve injury and repair," Experimental Neurology, vol. 211(1), pp. 180-193 (May 2008).

Wang et al., "Electrical stimulation promotes motor nerve regeneration selectivity regardless of end- organ connection," J. Neurotrauma, vol. 26(4), pp. 641-649 (Apr. 2009).

Ward et al., "Optogenetically-enhanced Axon Regeneration: Motorversus Sensory- Neuron Specific Stimulation," Eur. J. Neurosci., vol. 47(4), pp. 294-304 (Feb. 2018).

Wenjin et al., "Electrical Stimulation Promotes BDNF Expression in Spinal Cord Neurons Through Ca2+- and Erk-Dependent Signaling Pathways," Cell. Mol. Neurobiol., vol. 31(3), pp. 459-467 (Jan. 23, 2011).

Willand et al., "Electrical Stimulation to Promote Peripheral Nerve Regeneration," Neurorehabil. Neural Repair, vol. 30(5), pp. 490-496 (Jun. 1, 2016).

Witzel et al., "Electrical Nerve Stimulation Enhances Perilesional Branching after Nerve Grafting but Fails to Increase Regeneration Speed in a Murine Model," J. Reconstr. Microsurg., vol. 32(6), pp. 491-497 (Jul. 2016).

Wong et al., "Electrical stimulation enhances sensory recovery: A randomized controlled trial," Ann. Neurol., vol. 77(6), pp. 996-1006 (Jun. 1, 2015).

Xu et al. "Electrical Stimulation Promotes Regeneration of Defective Peripheral Nerves after Delayed Repair Intervals Lasting under One Month," Plos One, vol. 9(9), page e105045 (Sep. 2, 2014).

Yeh et al., "Timing of applying electrical stimulation is an important factor deciding the success rate and maturity of regenerating rat sciatic nerves," Neurorehabil. Neural Repair, vol. 24(8), pp. 730-735 (Oct. 2010).

Zhang et al., "Electrical stimulation enhances peripheral nerve regeneration after crush injury in rats," Mol. Med. Rep., vol. 7(5), pp. 1523-1527 (May 2013).

Zuo et al., "A single session of brief electrical stimulation enhances axon regeneration through nerve autografts," Experimental Neurology, vol. 323, p. 113074 (to be published Jan. 2020).

* cited by examiner

130

134

132

136

10'

10"

50

50

270

272

274

276

278

280

SYSTEMS AND METHODS FOR DELIVERING NEUROREGENERATIVE THERAPY

CROSS-REFERENCE TO RELATED APPLICATIONS

This application is a continuation of U.S. patent application Ser. No. 16/759,257, filed Apr. 24, 2020 and scheduled to issue on Feb. 15, 2022 as U.S. Pat. No. 11,247,045, which is a National Stage application in the United States of PCT Application PCT/US2018/057375, filed Oct. 24, 2018 and published on May 2, 2019 as PCT Publ. WO 2019/084182, which claims priority to U.S. Provisional Patent Application Nos. 62/577,141, filed Oct. 25, 2017, and 62/683,019, filed Jun. 11, 2018. The contents of all of the foregoing applications are incorporated by reference herein and made part of the present application in their entireties.

FIELD

This application relates generally to devices, systems and methods for locating and/or treating (e.g., regenerating, facilitating the treatment of, etc.) injured tissue, and more specifically, to devices, systems and methods that facilitate the regeneration of injured nerves (e.g., neuroregeneration).

BACKGROUND

Peripheral nerve injuries (PNI) are severely debilitating, affecting otherwise healthy patients by limiting their ability to perform activities of daily living. Peripheral nerve injuries may result from various etiologies, from complex trauma to iatrogenic and compressive neuropathies. However, despite various etiologies the mainstay to repair peripheral nerve damage is surgical repair of transected nerve ends or surgical release of compressed nerves. Unfortunately, even the best surgical procedures usually leave patients with marked deficits. Given the disability associated with PNI, a need clearly exists to improve outcomes.

Currently, clinical treatment of injured peripheral nerves is primarily surgical, either releasing the source of nerve compression or reattaching the transected nerve directly or with grafting materials. Surgery permits nerve regrowth by re-establishing nerve continuity but functional recovery remains inadequate. Generally, nerves regenerate slowly (~1 mm/day at their fastest) requiring long periods of time before reconnecting with denervated target muscle or sensory end-organs. The window of opportunity for nerve regeneration is short with the regenerative capacity of the injured neurons and the regenerative support of the distal nerve stump declining with time and distance. These factors together with the misdirection of regenerating nerves account for the frequent poor recovery.

SUMMARY

According to some embodiments, a system (and corresponding method) configured to deliver targeted electrical stimulation therapy to injured nerves is amenable to fit the needs of different injuries and clinical workflows, including different anatomical areas, injured nerves, nerve diameters, and types of nerve injury. The system can advantageously provide users with the ability to seamlessly interchange nerve interfaces to connect with and deliver neuroregenerative therapy (e.g., for neuroregeneration). The embodiments disclosed herein provide flexibility to users to apply neuroregenerative therapy prior to surgery, at the time of surgery, post-surgery, or a combination thereof, as desired or required.

According to some embodiments, additionally, the systems and methods allow for confirmation that the stimulating electrodes are functioning correctly by providing a means to verify the integrity of the electrode and/or system either through a physical self-verification or automatic verification steps. This becomes advantageous in situations where motor nerves are transected and no physical response (e.g., no muscle contraction) is present or in situations where a pure sensory nerve is transected and there are no physical responses to begin with. This same verification method allows for safe and continuous delivery of neuroregenerative therapy by monitoring current flow through the electrodes.

According to some embodiments, the systems and methods disclosed herein further allow users to perform nerve location tasks using the same or different nerve interfaces prior to commencing neuroregenerative therapy. The system is also configured to incorporate a single button that controls stimulus parameters, system modes, and therapy time providing an easy to use interface for a clinician minimizing training and complexity.

According to some embodiments, a method of stimulating a target nerve of a subject comprises, during a first phase, delivering stimulation energy of a first frequency via at least one electrode assembly, and, during a second phase, delivering to the subject stimulation energy of a second frequency for a predetermined period via the at least one electrode assembly, wherein delivering stimulation energy to the subject during the second phase creates a regenerative effect (e.g., neuroregenerative effect) to the target nerve, and wherein delivering stimulation energy during the first phase is configured to confirm at least one validation condition. In some embodiments, the second frequency is greater than the first frequency.

According to some embodiments, a method of stimulating a target nerve of a subject comprises, during a first phase, delivering stimulation energy of a first frequency via at least one electrode assembly, and, during a second phase, delivering to the subject stimulation energy of a second frequency for a predetermined period via the at least one electrode assembly, wherein delivering stimulation energy to the subject during the second phase creates a neuroregenerative effect to the target nerve, and wherein the second frequency is greater than the first frequency.

According to some embodiments, the at least one validation condition is that the at least one electrode assembly is working. In some embodiments, delivering stimulation energy during the first phase is configured to activate an indicator that the at least one electrode assembly is working. In some embodiments, the indicator comprises a visual indicator (e.g., a LED or other light source). In other arrangements, the indicator comprises a non-visual indicator (e.g., an audible indicator, a haptic feedback indicator, etc.).

According to some embodiments, the at least one validation condition is that the at least one electrode is contacting the target nerve. In some embodiments, delivering stimulation energy during the first phase is configured to facilitate locating the target nerve. In some embodiments, delivering stimulation energy at a first frequency during the first phase creates a visible and/or verbal (e.g., oral) response from the subject. In several embodiments, the visible response comprises a twitch, reflex, muscle response or other involuntary bodily movement.

According to some embodiments, the predetermined period is at least 10 minutes. In some embodiments, the predetermined period is at least 30 minutes. In some arrangements, the predetermined period is 30 minutes to 60 minutes.

According to some embodiments, the first frequency is 1 Hz to 40 Hz. In some embodiments, the first frequency is lower than 40 Hz. In some embodiments, the second frequency is 1 Hz to 100 Hz. In some embodiments, the first frequency is 1 Hz to 10 Hz, and wherein the second frequency is 10 Hz to 100 Hz.

According to some embodiments, the method further comprises positioning the at least one electrode assembly adjacent the target nerve of the subject.

The method additionally includes at least partially securing the at least one electrode assembly to the target nerve of the subject. In some embodiments, at least partially securing the at least one electrode assembly to the target nerve comprises using at least one of a suture, a barb, a tissue anchor, a flap and another type of mechanical connector. In one embodiment, at least partially securing the at least one electrode assembly to the target nerve comprises using an adhesive.

According to some embodiments, positioning the at least one electrode assembly adjacent the target nerve comprises not fastening the at least one electrode assembly to the subject. In some embodiments, wherein positioning the at least one electrode assembly adjacent the target nerve comprises aligning the at least one electrode assembly adjacent or near the target nerve (e.g., with or without the aid of an insertion tool).

According to some embodiments, wherein delivering stimulation energy to the subject during the first phase comprises delivering the stimulation energy in a repetitive burst sequence. In some embodiments, wherein repetitive burst sequence comprises at least two pulses. In some embodiments, wherein repetitive burst sequence comprises at least three pulses.

According to some embodiments, wherein the at least one electrode is included as part of a bipolar electrode assembly. In some embodiments, wherein positioning the at least one electrode assembly at or adjacent the target nerve comprises advancing the at least one electrode assembly and a lead secured to the at least one electrode through a cannula, sheath or other device with an internal opening. In some embodiments, in intraoperative settings, the at least one electrode assembly comprises a cuff electrode.

According to some embodiments, a device for stimulating a target nerve of a subject comprises at least one electrode assembly, and a lead physically coupled to the at least one electrode assembly, wherein, during a first phase, the at least one electrode is configured to deliver stimulation energy of a first frequency via at least one electrode assembly, wherein, during a second phase, the at least one electrode is configured to deliver to the subject stimulation energy of a second frequency for a predetermined period via the at least one electrode assembly, wherein delivery of stimulation energy to the subject during the second phase creates a neuroregenerative effect to the target nerve, and wherein delivery of stimulation energy to the subject during the first phase is configured to confirm at least one validation condition.

According to some embodiments, the at least one validation condition is that the at least one electrode assembly is working. In some embodiments, the device further comprises an indicator, wherein delivering stimulation energy during the first phase is configured to activate the indicator, the indicator being configured to provide confirmation that the at least one electrode assembly is working. In some embodiments, the indicator comprises a visual indicator (e.g., a LED or other light source). In some embodiments, the indicator comprises a non-visual indicator (e.g., an audible indicator, a haptic feedback indicator, etc.).

According to some embodiments, the at least one validation condition is that the at least one electrode is contacting the target nerve. In some embodiments, the delivery of stimulation energy during the first phase is configured to facilitate locating the target nerve. In some embodiments, the delivery of stimulation energy at a first frequency during the first phase creates a visible and/or verbal (e.g., oral) response from the subject. In some embodiments, the visible response comprises a twitch, reflex, muscle response or other involuntary bodily movement.

According to some embodiments, the first frequency is 1 Hz to 40 Hz. In some embodiments, the first frequency is lower than 40 Hz. In some embodiments, the second frequency is 1 Hz to 100 Hz. In some embodiments, the first frequency is 1 Hz to 10 Hz, and wherein the second frequency is 10 Hz to 100 Hz.

According to some embodiments, the delivery of stimulation energy to the subject during the first phase comprises delivering the stimulation energy in a repetitive burst sequence. In some embodiments, the repetitive burst sequence comprises at least two pulses. In some embodiments, the repetitive burst sequence comprises at least three pulses. In some embodiments, the least one electrode assembly comprises a cuff electrode.

According to some embodiments, a method of stimulating a target nerve of a subject comprises identifying the target nerve, positioning at least one electrode assembly relative to the subject to selectively stimulate the target nerve, and delivering therapeutic stimulation energy to the subject via the at least one electrode assembly for a predetermined time period to create a neuroregenerative effect to the target nerve, wherein the predetermined time period is at least 30 minutes, and wherein the at least one electrode assembly comprises a first electrode positioned immediately adjacent the target nerve and a second electrode, the second electrode being positioned physically apart from the first electrode.

According to some embodiments, the second electrode comprises a patch electrode positioned on a skin surface of the subject. In one embodiment, the first and second electrodes are included as part of a bipolar electrode assembly. In some embodiments, identifying the target nerve comprises soliciting a response from the subject via delivery of a validation stimulus to the subject. In some embodiments, the validation stimulus comprises a frequency that is lower than a frequency of the therapeutic stimulation energy. In some embodiments, the validation stimulus comprises a repetitive burst sequence with at least two pulses. In some embodiments, the repetitive burst sequence comprises at least three pulses.

According to some embodiments, a method of stimulating a target nerve of a subject comprises identifying the target nerve, positioning at least one electrode assembly adjacent to the target nerve, prior to positioning the at least one electrode assembly adjacent to the target nerve, validating that the at least one electrode is electrically activated when subjected to a validation stimulus, wherein the validation stimulus originates from a validation stimulus source, and delivering therapeutic stimulus to the subject via the at least one electrode assembly for a predetermined time period to create a neuroregenerative effect to the target nerve, wherein the therapeutic stimulus originates from a therapeutic stimulus source, wherein the predetermined time period is at least 30 minutes.

According to some embodiments, the validation stimulus source is the same as the therapeutic stimulus source, such that the validation stimulus source and the therapeutic stimulus source comprise a single stimulus course. In some embodiments, the single stimulus source comprises a hand-held device. In some embodiments, the validation stimulus source is different from the therapeutic stimulus source. In some embodiments, the validation stimulus comprises lower frequency than the therapeutic stimulus. In some embodiments, the validation stimulus comprises a repetitive burst sequence with at least two pulses. In some embodiments, the repetitive burst sequence comprises at least three pulses (e.g., 3, 4, 5 pulses, more than 5 pulses, etc.).

According to some embodiments, the present application discloses an electrical stimulation system comprising one or more electrodes that may be used for intraoperative or peri-operative nerve stimulation. In some embodiments, the system comprises a relatively small size, suitable to fit into the palm of an end-user. In some embodiments, one or more of the configurations disclosed herein provide the ability to interface the system with different electrodes. In some embodiments, the system is designed to be single use and disposable providing end-users, such as surgeons or other practitioners, the ability to use the system intraoperatively (e.g., provided the system is sterilized and packaged in appropriate packaging material).

In some embodiments, the various systems, devices and methods disclosed herein provide a practitioner with a way of locating a damaged nerve and treating it with electrical stimulation. The embodiments can be used intra-operatively or peri-operatively.

In some embodiments, the system can be used in peri-operative settings. The housing of the system can include controls (e.g., one or more sets of controls) to change the stimulus amplitude and/or other settings.

In some embodiments, the system comprises one or more controls to start, stop, pause, restart and/or otherwise alter the delivery of energy to heal injured tissue. In some embodiments, the system additionally comprises circuitry to enable power to the system and thus provide stimulation only when the appropriate interface has been connected. Visual indicators may be included on the housing or the connected interface. These indicators may provide end-users with signals relaying information regarding the status of the system, the active interface use, the mode it is operating in, the stimulus settings, and/or the time remaining on the delivery of the treatment. The indicators may comprise multiple light emitting diodes, graphical displays, or similar emissive elements. The housing also may contain an element used to secure the system to a surgical drape or other structure. This element may be but is not limited to an adhesive, strap, hook, or clip.

Additional aspects of the system include the ability to provide either monopolar or bipolar stimulation. In the case of intraoperative use, where the exposed injured tissue is preferably a nerve, the system may be deployed using a bipolar or monopolar electrode apparatus to interface with the injured nerve. The described electrode apparatus may allow the user to interface any diameter nerve by wrapping the electrode carrier body around the nerve and securing the wrapped portion in place using tabs. Lateral deflection of the tabs releases the wrapped nerve allowing easy removal of the electrode. One aspect of the electrode apparatus is that it is molded in a flat or open configuration allowing the electrode to spring back to this configuration when wrapped around a nerve. Molded tabs on the electrode allow the head portion of the electrode to be secured underneath them preventing the electrode to spring back to its flat configuration and maintaining a wrap around the interfaced nerve to deliver the appropriate stimulation treatment.

In some embodiments, for peri-operative use, an electrode is placed either during a surgical procedure or peri-operatively using a percutaneous method. In some embodiments, a monopolar electrode can be used where the electrode interface may not be in contact with the nerve directly. In such arrangements, the system can connect or otherwise couple to a return electrode (e.g., which can include a patch type electrode placed on the skin and connected to the system directly).

According to some embodiments, additional aspects of the system include a stimulation signal (e.g., that may comprise either constant voltage or constant current pulses). In some embodiments, a constant current pulse is used. In some embodiments, constant current stimulation amplitudes range from 0 to 20 milliamperes (e.g., 0-1, 1-2, 2-3, 3-4, 4-5, 5-6, 6-7, 7-8, 8-9, 9-10, 10-15, 15-20 milliamperes, values within the foregoing ranges, etc.).

According to some embodiments, for safe stimulation over a period a time, biphasic pulse outputs are used. This can help ensure that no net charge is being delivered at the electrode interface. In some embodiments, charge balancing is accomplished using a passive element (e.g., such as a capacitor coupled to the output of the stimulator). In some embodiments, active methods sample the output offset of the stimulator in a feedback loop and/or correct this either by generating additional pulses of the correct polarity or injecting a reverse offset to ensure that the net charge is zero. Other methods not specifically described herein may also be employed.

According to some embodiments, additional aspects of the system include a test mode (e.g., to allow the user to first deliver low-frequency stimulation (e.g., from 0.1 to 10 Hz) that permits the end-user to visualize if the injured tissue responds to stimulation). In some embodiments, the various configurations enable the user to adjust the stimulus output to a desired level and initiate the therapeutic delivery of electrical stimulation. Additional parameters can be adjusted.

According to some embodiments, additional aspects of the system include a modification of the first phase of stimulation and housing to accommodate a bipolar probe electrode to serve as a nerve locator. In some embodiments, the test mode can be modified to deliver electrical stimulation pulses sufficient to elicit a strong muscle contractile response following probe connection with a peripheral nerve. In several arrangements, the test mode provides stimulation doublet pulses (e.g., doublets) used to exploit the muscle catch-like property where successive stimuli lead to fused contractions. In certain embodiments, doublets allow for a greater muscle excursion and can be helpful in nerve location.

According to some embodiments, a method for treating injured tissue (e.g., nerve) comprises first interfacing tissue with an electrode suitable to the use-case (e.g., intra or peri-operative, other procedure, etc.). The method can also comprise securing or otherwise coupling an electrode to the system. In some embodiments, the system is then enabled to provide test stimulation to verify the responsiveness of the tissue to electrical stimulation. In some embodiments, the system is configured to permit the user to modify one or more operational parameters (e.g., amplitude). The method further includes the user initiating neuroregenerative therapy to treat the injured tissue (e.g., targeted nerve).

According to some embodiments, the methods disclosed herein are configured to provide a targeted approach to treating injured tissue with electrical stimulation. In some embodiments, unlike other stimulation systems, the systems, devices and methods disclosed herein can be configured to enable users to choose whether to apply the system intra-operatively using a pre-determined suitable electrode inter-face or peri-operatively using a suitable electrode interface. In some embodiments, the length of a surgical procedure will determine how the device is applied.

BRIEF DESCRIPTION OF THE DRAWINGS

These and other features, aspects and advantages of the present application are described with reference to drawings of certain embodiments, which are intended to illustrate, but not to limit, the concepts disclosed herein. The attached drawings are provided for the purpose of illustrating concepts of at least some of the embodiments disclosed herein and may not be to scale.

DETAILED DESCRIPTION

Figure 1:
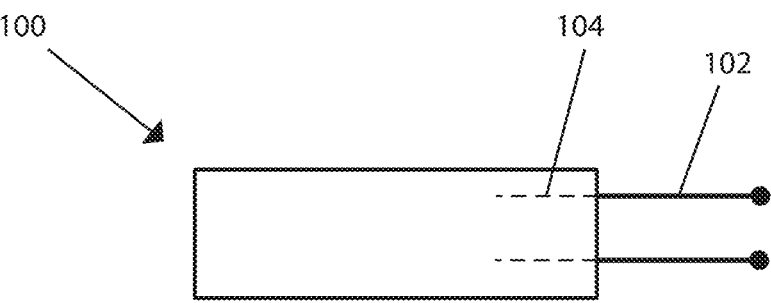
FIG. 1 illustrates a schematic of various configurations of the system according to one embodiment.
Figure 1:
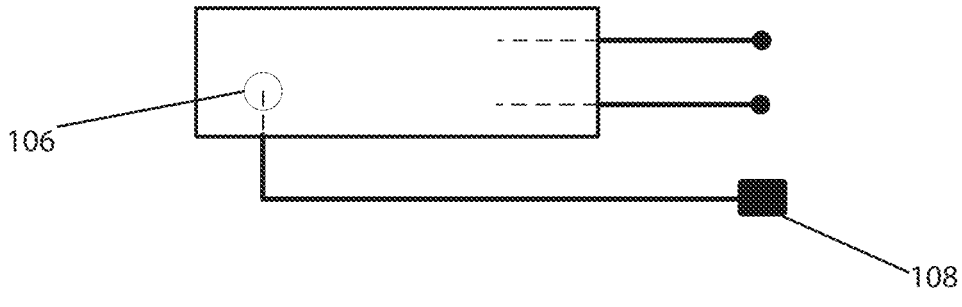
Figure 1:
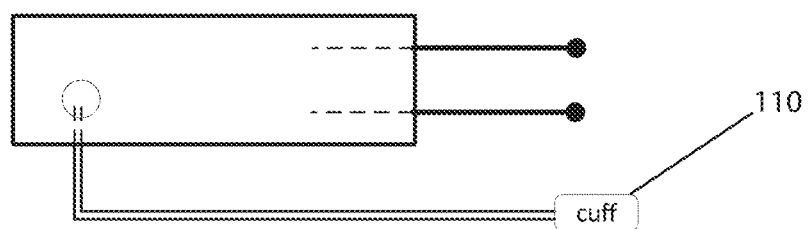

The devices, systems and associated methods described herein may be used during surgical procedures to locate nerve tissue, test nerve tissue excitability and/or provide neuroregenerative therapy (e.g., electrical stimulation) to treat targeted nerve tissue (e.g., injured nerve tissue). The embodiments disclosed herein can be used for peripheral nerves; however, other types of nerves can also be targeted, such as, for example, nerves in the autonomic system or nerves in the central nervous system. For example, peripheral nerves may include the median nerve in the upper limb, the sciatic nerve in the lower limb, smaller nerves (e.g., the intercostal branches in the thorax), etc. Autonomic nerves may include, without limitation, the vagus nerve. Nerves in the central nervous system may reside in the spinal cord or brain.

In some embodiments, a system (and corresponding method) configured to deliver targeted electrical stimulation therapy to injured nerves is amenable to fit the needs of different injuries and clinical workflows, including different anatomical areas, injured nerves, nerve diameters, and types of nerve injury. The system can advantageously provide users with the ability to seamlessly interchange nerve interfaces to connect with and deliver neuroregenerative therapy (e.g., for neuroregeneration). The embodiments disclosed herein provide flexibility to users to apply neuroregenerative therapy prior to surgery, at the time of surgery, post-surgery, or a combination thereof, as desired or required.

Additionally, the systems and methods allow for confirmation that the stimulating electrodes are functioning correctly by providing a means to verify the integrity of the electrode and/or system either through a physical self-verification or automatic verification steps. This becomes advantageous in situations where motor nerves are transected and no physical response (e.g., no muscle contraction) is present or in situations where a pure sensory nerve is transected and there are no physical responses to begin with. This same verification method allows for safe and continuous delivery of neuroregenerative therapy by monitoring current flow through the electrodes.

In some embodiments, the systems and methods disclosed herein further allow users to perform nerve location tasks using the same or different nerve interfaces prior to commencing neuroregenerative therapy. The system is also configured to incorporate a single button that controls stimulus parameters, system modes, and therapy time providing an easy to use interface for a clinician minimizing training and complexity.

There exists a need for a purposely designed system that can accommodate an appropriate nerve interface for prolonged stimulation and deliver electrical stimulation to injured nerves to accelerate nerve regeneration. Many medical disciplines can benefit from using the disclosed system and interface to accelerate nerve regeneration. These disciplines include but are not limited to: plastic surgery, orthopedic surgery, otolaryngology, oral surgery, and neurosurgery. In addition, clinical diagnoses that would be improved from using the disclosed device include but are not limited to: sharp lacerations, nerve transection, nerve compression, compressive neuropathy, cancer injury to nerve, peripheral neuropathy, iatrogenic nerve injury, obstetrical brachial plexus palsy, neonatal brachial plexus palsy, facial paralysis, and radiculopathy.

More specifically, the disclosed system and interface is designed for intraoperative use and/or peri-operative use, and may improve surgical outcomes in the following situations: nerve transection, nerve decompression, nerve transfer, nerve graft, neurolysis, nerve allograft, thoracic outlet decompression, carpal tunnel release, cubital tunnel release, and tarsal tunnel release. While these listed examples may benefit from the disclosed device, the list is not exhaustive and only provides an example of what medical conditions may be treated.

In some arrangements, during the course of certain surgical procedures (e.g., complex or complicated surgical procedures), nerves may not be visible and/or may be surrounded by connective tissue, scar tissue and/or other type of tissue. Devices such as nerve locators can be used to probe tissue using electrical stimuli to test and confirm if the tissue is a nerve. Furthermore, there are instances where a nerve locator is used to test for motor components of a nerve fascicle prior to a nerve transfer procedure.

In some embodiments, a nerve may be transected or cut (e.g., partially transected, mostly transected, fully transected, etc.), crushed and/or otherwise injured or damaged. In such instances, the injured nerve(s) may benefit from application of stimulation therapy. For example, in some embodiments, brief but continuous electrical stimulation applied to the proximal segments of the injured nerves can provide therapy and/or other benefits to the targeted nerve (s). In some embodiments, such a treatment can accelerate nerve regeneration of injured nerves. This treatment is referred to herein as neuroregenerative therapy.

The various embodiments disclosed herein offer one or more advantages. For example, the devices and systems described herein provide the ability to function as a hand-held, dual-purpose technology that is designed and otherwise configured to deliver both nerve location/testing functionality and neuroregenerative therapy (e.g., continuous stimulation, intermittent stimulation, etc.) for the treatment of injured nerves (e.g., neuroregeneration). An additional advantage of the described embodiments is the ability to switch between bipolar and monopolar stimulation nerve probes as well as other probes or electrodes that can be interfaced with the system.

In some embodiments, the surgeon or other practitioner benefits by using the various devices, systems and/or methods disclosed hereon. For example, the various embodiments disclosed herein can be fully integrated, can replace multiple (e.g., two or more, separate, etc.) devices and/or systems, can be controlled using a single hand and/or can provide one or more benefits or advantages.

Another benefit provided by one or more of the embodiments discussed herein is that the disclosed devices/system may apply continuous stimulation for a pre-defined period of time allowing the system to be used hands free (e.g., without the need to manipulate or otherwise use a button or other controller to deliver stimulating energy) when used to treat injured tissue.

General System Overview

In one embodiment, the system comprises of a housing, a nerve probe, a port for additional electrodes, visual indicators, a power source, a stimulus pulse generator/controller, a central processing unit, and user controls. With specific reference to the schematic of FIG. 1, the system 100 can be configured to function in multiple configurations. Additional configurations of the system may also exist, even though not specifically illustrated in FIG. 1 and/or other figures of the present disclosure. For any of the embodiments disclosed herein, a device or system can include fewer components and/or features, as desired or required. For example, in some arrangements, a device or system does not include a visual indicator, a power source and/or the like.

In one configuration, the nerve probe 102 is bi-polar, that is, comprising two separate electrode conductors that are internally connected to a stimulus generator. In another configuration, as also illustrated in FIG. 1, the nerve probe may be bi-polar, that is comprising of two separate electrode conductors. However, in the illustrated arrangement, the conductors 104 can be shorted together internally essentially producing a single probe. This connected probe may function in some embodiments as a monopolar probe if an appropriate return electrode is connected to the system's electrode port 106. As shown schematically in FIG. 1, the return electrode 108 can comprise a needle, surface pad and/or another conductive material so long as a return path is present. Additional details regarding such embodiments are provide herein.

In the configurations discussed above, the system 100 may be used to probe nerve tissue with a stimulus being delivered at or near the nerve probe. Thus, the system 100 can be used as a nerve locator or evaluator. The bi-polar or monopolar configurations may be advantageous to surgeons depending on the location of the nerve that is being probed or the type of surgical procedure being performed.

In yet another configuration, such as in the embodiment also shown in FIG. 1, a cuff-type electrode 110 that is configured to interface (e.g., directly, indirectly, etc.) with a nerve may be connected to the system's electrode port. Such an embodiment can be advantageous for delivering neuroregenerative therapy to an injured nerve. In such a configuration, the stimulus output may be driven (e.g., entirely) to the plugged-in electrode and not the nerve probe.

In some embodiments, the electrode that is plugged into the port may comprise of one or more electrode contacts, and through the electrode port, may be physically connected to the stimulus generator. Regardless of the exact configuration used, in some embodiments of the present application, the system can be configured to detect if and which electrode is plugged into the port and ensure the appropriate stimulation is output is being driven. Additional details about various system embodiments, components, portions, subsystems and/or the like are provided below.

Housing

Figure 2A:
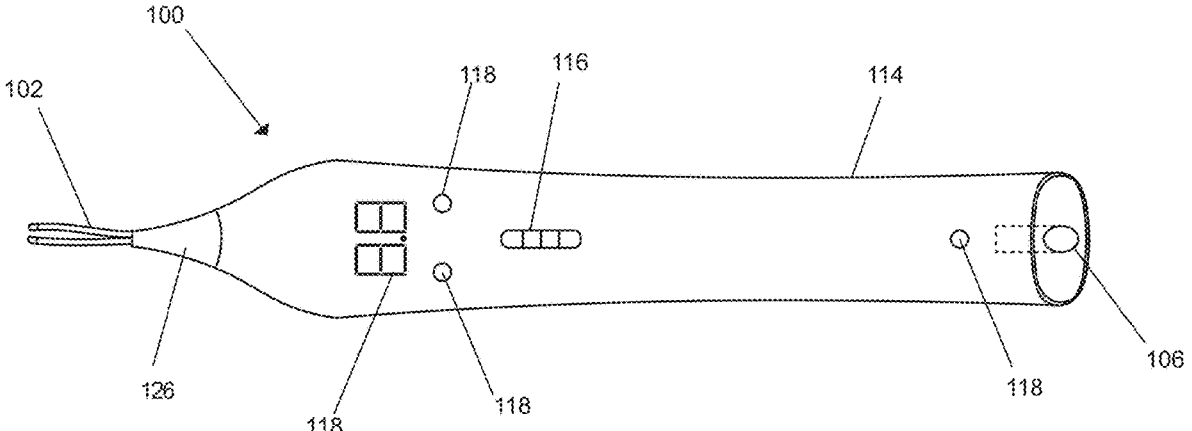
FIG. 2A illustrates a top view of a hand-held nerve locator according to one embodiment.

In some embodiments, as illustrated in FIG. 2A, the system can comprise a housing 114 that may include user controls 116, visual indicators 118, a power source, a stimulus pulse generator/controller, a central processing unit and/or any other component or portion, as desired or required. As shown, the housing can include one or more materials, such as, for example, thermoplastic type material (e.g., polyethylene, polypropylene, polyvinyl chloride, polystyrene, polyamides, polyesters, polyurethanes, etc.), thermoplastic elastomers (e.g., in some embodiments resulting in a soft grip-able texture), metals or alloys (e.g., stainless steel, aluminum, other brushed or polished metals or alloys, etc.), composite materials and/or the like, as desired or required.

In some embodiments, the housing and accompanying internal components can be configured to be reused. Thus, such components or portions can be designed and otherwise configured to be sterilized and/or otherwise cleaned. For example, the system can be sterilized via exposure to ethylene oxide, chlorine dioxide, vaporized hydrogen peroxide, gamma rays, electron beams and/or the like.

Figure 2B:
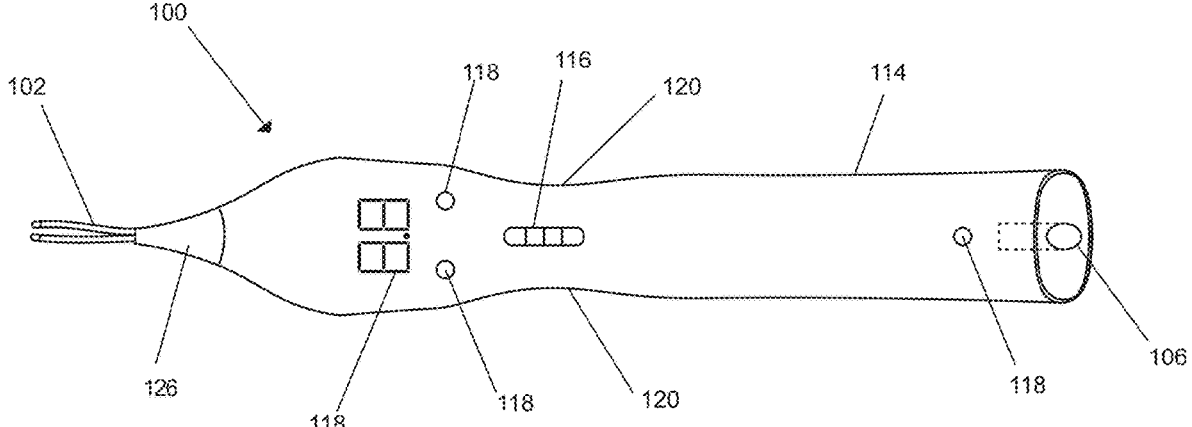
FIG. 2B illustrates a top view of a hand-held nerve locator according to one embodiment incorporating lateral grooves to facilitate holding using one hand.

According to some embodiments, the housing is designed to fit ergonomically into the hand of a surgeon, as illustrated in FIG. 2B. Thus, in some arrangements, the housing is shaped with grooves or scallops 120 and/or the housing includes an ergonomic shape to facilitate holding regardless of the handedness (e.g., right-handedness or left-handedness) of the user. In other embodiments, the housing is specifically designed for a single handedness of a user (e.g., right-handedness or left-handedness). Such grooves or scallops 120 can be symmetrical, non-symmetrical, aligned, offset and/or otherwise configured. As shown, in one embodiment, the deepest portion of the grooves 120 may be offset from the widest portion of the housing in range of 0.1 to 10 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10 mm, distances between the foregoing, etc.).

Figure 2C:
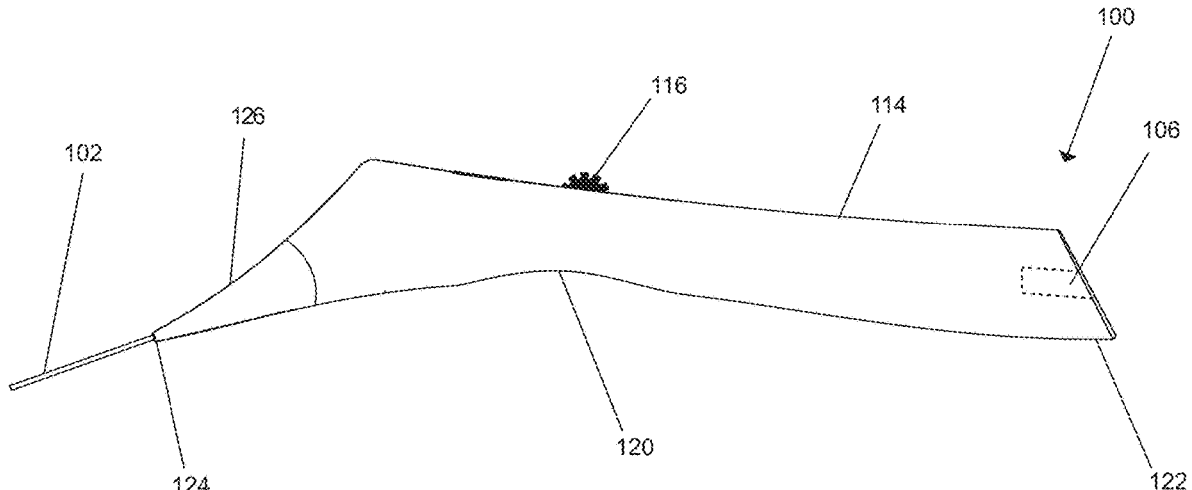
FIG. 2C illustrates a side view of a hand-held nerve locator according to one embodiment incorporating a verti-cal groove to facilitate rotation and access to controls using one hand.
Figure 2D:
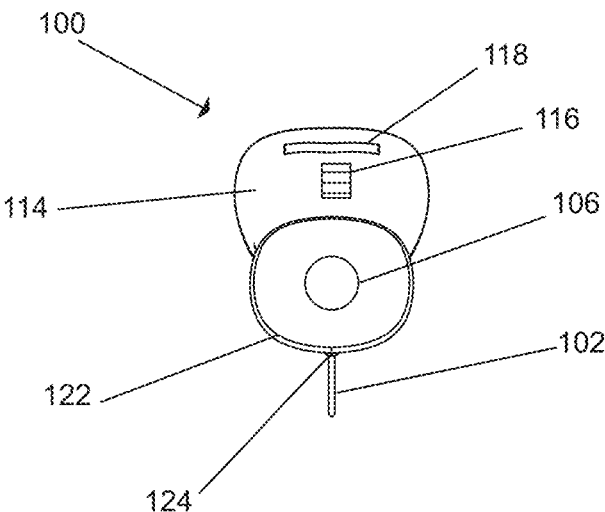
FIG. 2D illustrates a rear view of the hand-held nerve locator according to one embodiment showing access to the nerve port.

In some embodiments, the grooves 120 may be along the longitudinal axis, horizontal axis, the underside of the housing, or a combination of above. See, for example, FIG. 2C. In some embodiments, the housing comprises a proximal end 122 and distal end 124. The distal end 124 can include visual indicators 118 and a nerve probe 102 or a combination thereof. In some embodiments, the proximal end comprises a nerve port 106 that may include a nerve probe 102.

In some embodiments, the distal end and proximal end may be collinear or offset. For example, in some arrangements, the distal end and proximal end are offset by an angle ranging from 1° to 30° (e.g., 1-2, 2-3, 3-4, 4-5, 5-6, 6-7, 7-8, 7-8, 8-9, 9-10, 10-15, 15-20, 20-25, 25-30, 5-25, 10-20°, angles between the foregoing ranges, etc.), resulting in an angled distal end (e.g., relative to the proximal end). In some embodiments, such an angled distal end configuration can advantageously facilitate use of the device as shown, e.g., in FIG. 2C. Additionally, the angled offset can help prevent the housing from rolling (e.g., off a table, cart, other platform, etc.) if placed on a moderately inclined or uneven surface such as when a surgeon or other practitioner may set aside the housing to perform other operative tasks.

In some embodiments, the length of the housing, or the distance from proximal to distal ends, can be 10 to 40 cm (e.g., 10-15, 15-20, 20-25, 25-30, 30-35, 35-40, 15-25, 20-40 cm, lengths between the foregoing ranges, etc.). In other embodiments, the length of the housing can be less than 10 cm or greater than 40 cm, as desired or required by particular application or use. Further, the width (e.g., diameter or cross-section dimension) of the housing can be 0.5 to 3 cm (e.g., 0.5-1, 1-1.5, 1.5-2, 0.5-2, 2-2.5, 2.5-3 cm widths between the foregoing ranges, etc.).

In some embodiments, the proximal end of the housing comprises a hook-shaped or other curved or angled extension or an enclosed ring physically connected to the housing. In some arrangements, the extension may be used to hang the housing from an IV pole, another type of hook and/or the like.

In some embodiments, the housing may include a slot or opening to facilitate a pull-tab that interfaces with a battery. The pull-tab may allow for separation of the battery contacts preventing powering of the system. This is advantageous as it, among other things, prolongs the shelf life of the system. In some embodiments, the pull-tab slot or opening is located at, in or along the proximal end of the housing and the width of the slot may range from 5 mm to 30 mm (or the width of the housing). The height of the slot can range from 0.1 to 2 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-1.5, 1.5-2 mm, heights between the foregoing ranges, etc.).

As illustrated in FIGS. 2A to 2D, the system 100 can comprise a first set of user operable controls 116 for adjusting the parameters of the stimulus being delivered. In some embodiments, the system is configured to permit the user to discretely control the stimulus parameters, for example the stimulus amplitude or pulse width, to determine the threshold of nerve activation (e.g., threshold testing) and/or the like. This can be particularly relevant when a nerve is encompassed by scar tissue and/or other tissue (e.g., and requires a relatively large stimulus current to depolarize). Dissection of the scar and/or other obstructing tissue can result in a lower requirement for activation current.

In one embodiment, the controls may include two buttons. In another arrangement, the first set of controls may include a slider or similar feature or device. In yet another arrangement, the first set of controls may include a wheel control (e.g., a roller, a wheel, etc.). However, any other type of control (e.g., button, dial, etc.) can be incorporated into the device, either in lieu of or in addition a slider and/or a wheel control. In some arrangements, when using the wheel control, a discrete set of steps may allow for adjusting the stimulus amplitude. Thus, the wheel and/or any other control can be configured to be moved between discrete steps or positions. However, in other arrangements, the stimulus amplitude can be selected along a range of non-discrete levels (e.g., along a continuous spectrum of amplitudes). In some arrangements, the wheel may be coupled to a rotary encoder to discretize the movement of the wheel. In other arrangements, the rotary encoder may include detents to provide tactile feedback to the user when engaging the control.

According to some arrangements, the system may also include a secondary set of user operable controls. Such secondary controls can be configured to start, stop and/or pause the initiation or cessation of the treatment. In one embodiment, the secondary control may be used to power the system on and off. In some arrangements, the secondary set of controls may be placed near the first set of user operable controls. In one embodiment, the secondary control may be part of the primary user control. For example, the slider or wheel control may be coupled to a switch such that pressing the slider or wheel control results in activation of a momentary switch or similar. Any other type of control (e.g., button, switch, foot pedal, touchscreen, etc.) can be used.

In one embodiment, the system comprises a pull-tab control (e.g., as described herein) to control power to the system. In some arrangements, the system includes a switch or button used to control power to the system.

According to some embodiments, as discussed in greater detail herein, the system can also comprise a nerve port 106 coupled (e.g., physically coupled, operatively coupled, etc.) to the housing. This can allow users to connect (e.g., physically or operatively couple) a separate electrode to the system. As a control, the act of plugging in or physically connecting a separate electrode to the system may change the operating mode of the system as described earlier in system configurations.

In some embodiments, shown in FIGS. 2A to 2D, the nerve port may be included in the proximal aspect 122 of the housing. In some arrangements, the nerve port can allow for connections parallel to the longitudinal axis of the housing (see, e.g., FIG. 2D). In other arrangements, the nerve port may be included such that the connected component connector is perpendicular (e.g., exactly perpendicular, or generally or substantially perpendicular) to the longitudinal axis of the housing. In one embodiment, the act of plugging in or physically connecting a separate electrode to the system enables the system to power on.

Figure 3:
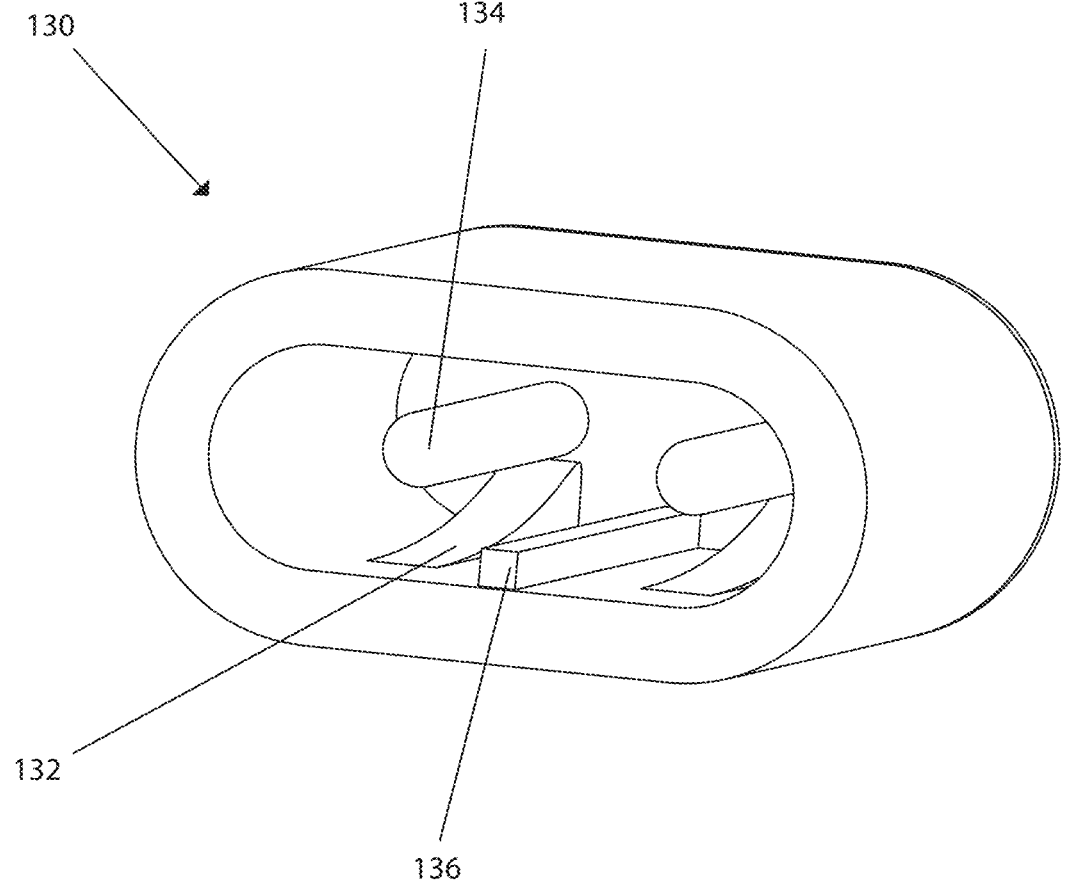
FIG. 3 illustrates an oblique view of a modified touch-proof jack according to one embodiment used to provide a contact for jack detection circuitry.

To detect if an electrode is present and physically connected to the system, a modified jack 130 may be included with the nerve port, as depicted in FIG. 3. For example, in some embodiments, the jack 130 can comprise a touch-proof jack (e.g., designed according to IEC 60601). The modified jack may include a flexible contact 132 that may be in physical contact with the main pin 134. However, in such an embodiment, upon introduction of an electrode lead connector, the physical connection between the flexible contact and main pin can be configured to be broken. In some arrangements, the jack can include one or more flexible contacts. In other arrangements, a polarity stand-off 136 may be included with the jack 130 to ensure the correct polarity of the plug being connected. In some embodiments, a standard touch-proof jack 130 with multiple pins/contacts or equivalent is used. In other embodiments, the jack or coupling 130 can be differently configured or designed (e.g., with another set of features or components), as desired or required.

Figure 4:
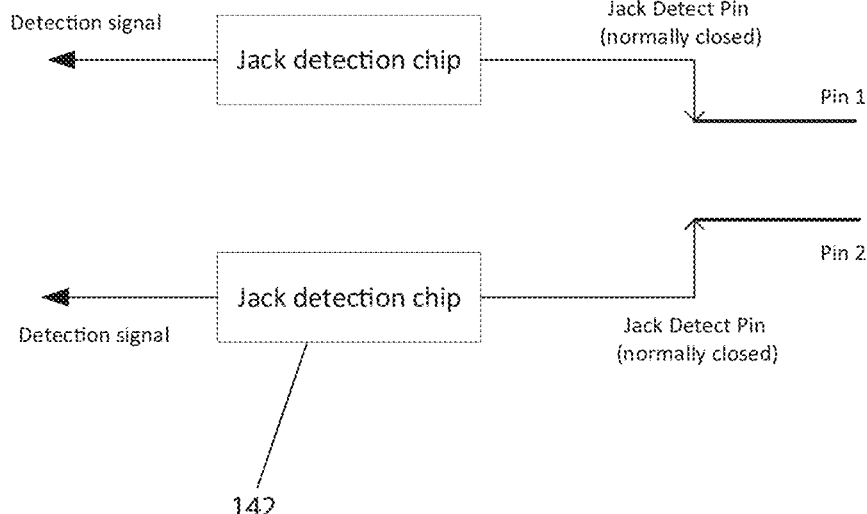
FIG. 4 illustrates a schematic of jack detection circuitry according to one embodiment configured to detect medical touchproof connections.

In some embodiments, the contacts on the jack may be wired to a jack detection circuit shown 142, such as the one illustrated in FIG. 4. This circuit 142 can include a microcontroller and passive components that may be used to detect the status of the connection.

In one embodiment, the circuit 142 includes standard jack detection chips 142 used in the mobile phone industry to detect headsets. These chips may include but are not limited to NCX8193 from NXP Semiconductors or MAX13330 from Maxim Semiconductor. In some arrangements, the chips can be configured to include the benefit of moisture detection, which allows the system to prevent enabling full power or other settings if moisture is detected in the jack housing. This may arise, for instance, when the system is used in an intraoperative setting.

Indicators

In several embodiments, the system comprises at least one set of indicators 118. In one embodiment, the first indicator may include a bar graph type display made by placing at least two visual emitting devices (e.g., LEDs) near one another. In some arrangements, the first indicator may include a multi-segment (e.g., 7-segment) display, as shown in FIG. 2A. The multi-segment (e.g., 7-segment) display may include more than one digit and decimal place, as desired or required. In some embodiments, the first indicator may comprise of a liquid crystal display (LCD), a plasma display, cathode ray tube display (CRT), organic light-emitting diode display (OLED), thin-film transistor display (TFT) and/or any other type of display.

In one embodiment, the purpose of such displays or indicators is to convey information regarding stimulus parameters, such as, for example and without limitation, amplitude, pulse width, frequency, duration, other time parameter and/or the like. In some arrangements, the display is configured to provide information related to time, such as, for example, a timer or count-down clock. Such information can be beneficial and advantageous in determining the time remaining or elapsed of a treatment application and can help guide the surgeon or other practitioner is conducting neuroregenerative therapy (e.g., such as brief electrical stimulation, other type of electrical stimulation, etc.) of injured or other targeted nerve tissue. In some arrangements, a combination of stimulus parameters, time-related parameters and/or any other data or information is displayed on the indicator. Such data and/or information, regardless of its exact nature, can be displayed in an alternating manner, via user controlled switch and/or the like. In some arrangements, the user can customize the type and/or manner in which the data and/or information is provided by the indicator (e.g., what data/information is provided, how it is provided to the user, etc.).

By way of example, according to some arrangements, the first set of indicators may be used to indicate power being delivered to the system. In one example, when the previously described pull-tab (or similar feature or component) is used to control power delivery to the system and a user pulls the tab, the first indicator may illuminate indicating that the system is powered.

In some embodiments, the system comprises additional indicators, as desired or required. For example, the system can include a second (or additional) set(s) of indicators 118 that can advantageously provide to the practitioner or other user additional data and/or information provided by a first indicator (e.g., time-related data or information, stimulus parameters, etc.). In some embodiments, the system may include a third set of indicators 118. In one embodiment, the third set of indicators 118 is located at or near the distal aspect of the housing. However, the indicator(s) of the system, regardless of how many are included, what data/information they are configured to provide, etc., can be included at any location, as desired or required. By way of example, the third set of indicators can comprise LEDs situated in a cap 126 that acts as a light pipe. Such a cap can be physically (e.g., directly or indirectly) coupled to the housing 114. In some arrangements, the cap and light pipe may can be designed and/or otherwise configured to permit visibility from any direction, such as, for example, when viewing the housing from above, below, beside, behind and/or the like (e.g., due to the angled distal aspect).

In some embodiments, an indicator (e.g., a first, a second, a third indicator, etc.) can be configured to display the status of the system. For example, a first solid color can indicate the state (e.g., active or inactive) of the output. In some arrangements, the output may be physically (e.g., directly or indirectly) connected or coupled to the nerve probe. Thus, for instance, in some arrangements, a first solid color may indicate if the nerve probe is active. In one specific example, referring to the previously described system configurations, a first solid color may indicate the nerve probe is active in either a bi-polar or monopolar configuration.

In some embodiments, a set of indicators (e.g., a third set of indicators) can be configured to flash (e.g., on/off) a first color to indicate output of a stimulus. In some arrangements, the flashing may be timed to coincide with the output of a stimulus pulse. In other arrangements, the flashing may be asynchronous with the output of a stimulus pulse. Any other type of configuration can be used to provide data and/or other information to the user via the indicators (e.g., different textual and/or graphical representation, different alert effects, etc.), as desired or required.

In some embodiments, the flashing is replaced with a pulsating output. In some arrangements, the pulsating output may include the ramping up of the light intensity from zero to a predetermined maximum and then a ramp down from the maximum to zero. In some arrangements, the pulsating output starts the ramping up from a non-zero intensity value and concludes the ramp down from the maximum to a non-zero intensity value.

In some embodiments, a visual indicator (e.g., the third set of visual indicators) can be configured to flash or pulsate to indicate an open circuit between the stimulating electrode and the return electrode. In one specific example, if there is no contact between the bi-polar tips of the nerve probe, an open circuit would be indicated that may trigger the flashing or pulsating of the visual indicator. In another specific example, when the system is operating in the previously described monopolar configuration, the lack of current flow between the stimulating electrode and the return electrode may trigger the flashing or pulsating of the visual indicator. In some embodiments, the flashing of an indicator (e.g., the third indicator) with a first color may occur at stimulus settings greater than zero.

In some embodiments, flashing or pulsating of an indicator (e.g., the third indicator) may occur with a second color. In some arrangements, the second color may be different from the first color. By way of example, the flashing or pulsating of the second color may indicate a closed circuit. In one embodiment, if there is current flow contact between the bi-polar tips of the nerve probe, an indication of a closed circuit would be provided, which trigger the flashing or pulsating of the visual indicator. In another specific example, when the system is operating in the previously described monopolar configuration, when current flow is present between the stimulating electrode and the return electrode, the flashing or pulsating of the visual indicator may be activated or triggered.

In some embodiments, the system may include a fourth (or additional) set(s) of indicators 118, as desired or required for a particular application or use. In some arrangements, the fourth set of indicators may be present next or near to the nerve port 106. In some embodiments, the fourth set of indicators may indicate the status of the nerve port 106. In some arrangements, the fourth set of indicators may function similarly to the third set (and/or other sets) of indicators and can comprise of multiple colored indicators and/or similar outputs.

The indicators described above can be incorporated into any of the device or system embodiments described herein and may be modified as desired or required.

Central Processing Unit

In some embodiments, any of the system configurations described herein can be part of a smart system with various electronic features, safety mechanisms and/or the like. Details about some of such features, mechanisms and/or other properties are provided herein.

Figure 5:
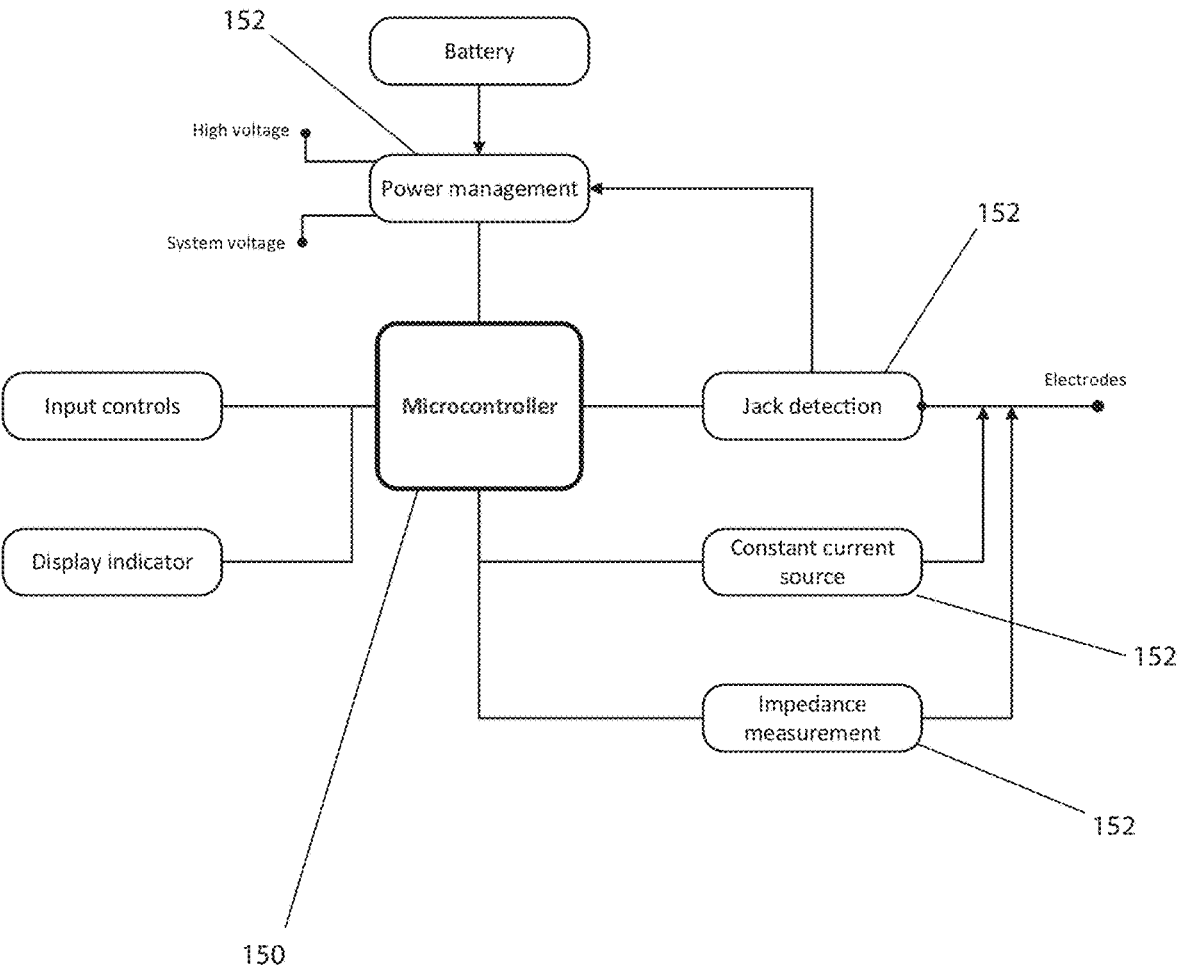
FIG. 5 illustrates a schematic view of the main micro-controller and sub-systems that interact with the microcon-troller to create the system according to one embodiment.

In some embodiments, a control sub-system or central processing unit of the system can be built in association (e.g., around) a microcontroller 150. In some arrangements, the microcontroller is configured to be programmed, to store and execute code and/or otherwise carry out certain tasks to property and effectively operate the system. In some embodiments, the microcontroller contains timing features, e.g., enabling a timed stimulus output. In other embodiments, the microcontroller interfaces with at least one or more sub-systems 152 that are described herein (see, e.g., FIG. 5).

Power Source

In some embodiments, any of the systems disclosed herein can be designed to be relatively small, to be disposable, to include handheld operation and/or to include other desired or required features. In other arrangements, the system may be reusable.

In some embodiments, the system is powered or electrically energized using an energy source, such as a battery, an AC source and/or the like. In some arrangements, the power source comprises a battery with a standard lithium coin cell. In other arrangements, however, if a larger capacity is needed, type N batteries or other similar alkaline batteries may be substituted. In some arrangements, the battery may be rechargeable. Any other type of battery or other local power source can be used, as desired or required.

In some embodiments, the system may include a power management sub-system. In these embodiments, the power management sub-system may include one or more sub-components, such as, for example, a low-noise low-dropout switching type regulators to maintain stable operating voltages in the range of 3 to 5 V. For example, in some embodiments a Texas Instruments LP5912 can be used.

In some embodiments, the power-management sub-system comprises a second sub-component having a means to generate higher voltages required to stimulate tissue. In such embodiments, the power management sub-system can include a low-power step-up boost converter, such as, by way of example and without limitation, a Texas Instruments TPS61096A. In some embodiments, the higher voltage range may be between 10 and 50 V (e.g., 10-15-15-20, 20-25, 25-30, 30-35, 35-40, 40-45, 45-50, 20-40, 25-35 V, values between the foregoing, etc.).

In some embodiments, the sub-components of the power management sub-system are regulated (e.g., enabled and disabled) via a microcontroller 150. In other arrangements, the act of physically connecting or plugging in an electrode into the nerve port 106 may enable or disable the sub-components of the power management sub-system via the jack detection circuitry 142 that was described herein.

In some embodiments, the power management sub-system may include a tilt sensor. Such a tilt sensor can be configured to provide data and/or other information to the user. For example, data or information can relate to whether the system was placed on a flat surface or is being held in a non-horizontal position. In some arrangements, the output of the tilt sensor may engage a low power mode through the power management sub-system.

Output Stage

In some embodiments, the system comprises a stimulus output stage sub-system. In some arrangements, the electrical output of such a sub-system is configured to selectively stimulate tissue. The system microcontroller can be configured to generate a rectangular stimulus pulse that is conditioned by the stimulus output stage sub-system. The stimulus output stage sub-system can be configured to generate the stimulus pulse. In some embodiments, the stimulus pulse comprises of a biphasic constant current or voltage pulse.

In some embodiments, the stimulus output stage sub-system comprises a capacitively-coupled output, e.g., to help ensure that a net-zero charge is being delivered to the tissue. In some embodiments, the stimulus output stage sub-system comprises a H-bridge used to switch current polarity. The H-bridge can be coupled to a current source, as desired or required. In some embodiments, the current source comprises a Howland current pump.

According to some embodiments, the stimulus output stage sub-system is configured to generate stimulus pulses with pulse durations ranging from 1 to 500 microseconds (e.g., 1-5, 5-10, 10-20, 20-30, 30-40, 40-50, 50-60, 60-70-70-80, 80-90-100, 100-120-120-140, 140-160, 160-180, 180-200, 200-250, 250-300, 300-350, 350-400, 400-450, 450-500, 0-20, 1-30, 0-40, 0-50, 0-100, 50-150, 100-200, 100-300 microseconds, durations between the foregoing ranges, etc.). In some arrangements, the sub-system is configured to generate stimulus pulses amplitudes ranging from 0-20 mA (e.g., 0-1, 1-2, 2-3, 3-4, 4-5, 5-6, 6-7, 7-8, 8-9, 9-10, 10-15, 15-20 mA, values between the foregoing, etc.). In some arrangements, the sub-system is configured to generate pulse trains in the frequency range of 0.1-100 Hz (e.g., 0.1-0.5, 0.5-1, 1-2, 2-3, 3-4, 4-5, 5-10, 10-15, 15-20, 20-25, 25-30, 30-40, 40-50, 50-60, 60-70, 70-80, 80-90, 90-100, 20-80-40-60, 10-70 Hz, frequencies between the foregoing, etc.).

Figure 6A:
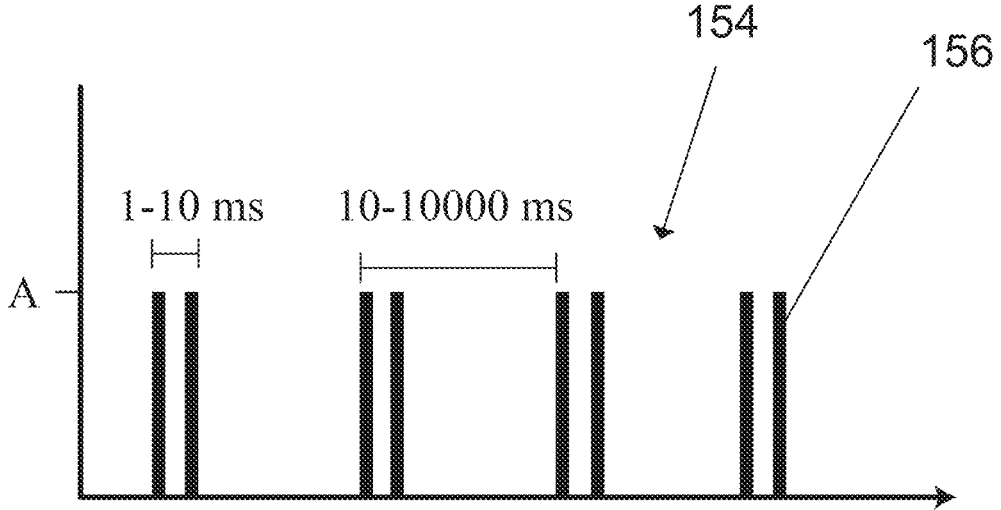
FIG. 6A illustrates a graph depicting doublet stimulus pulses at an arbitrary amplitude according to one embodi-ment.

According to some embodiments, the pulse train 154 comprises one or more pulses at an amplitude A separated by a short inter-pulse interval, called a doublet pulse 156, in the range of 1-10 ms (e.g., 1-2, 2-3, 3-4, 4-5, 5-6, 6-7, 7-8, 8-9, 9-10 ms, intervals between the foregoing, etc.). One embodiment of such a configuration is illustrated schematically in FIG. 6A. In some embodiments, use of doublet pulses allows exploitation of a muscle's natural catch like property resulting in greater muscle contraction or visible response.

Figure 6B:
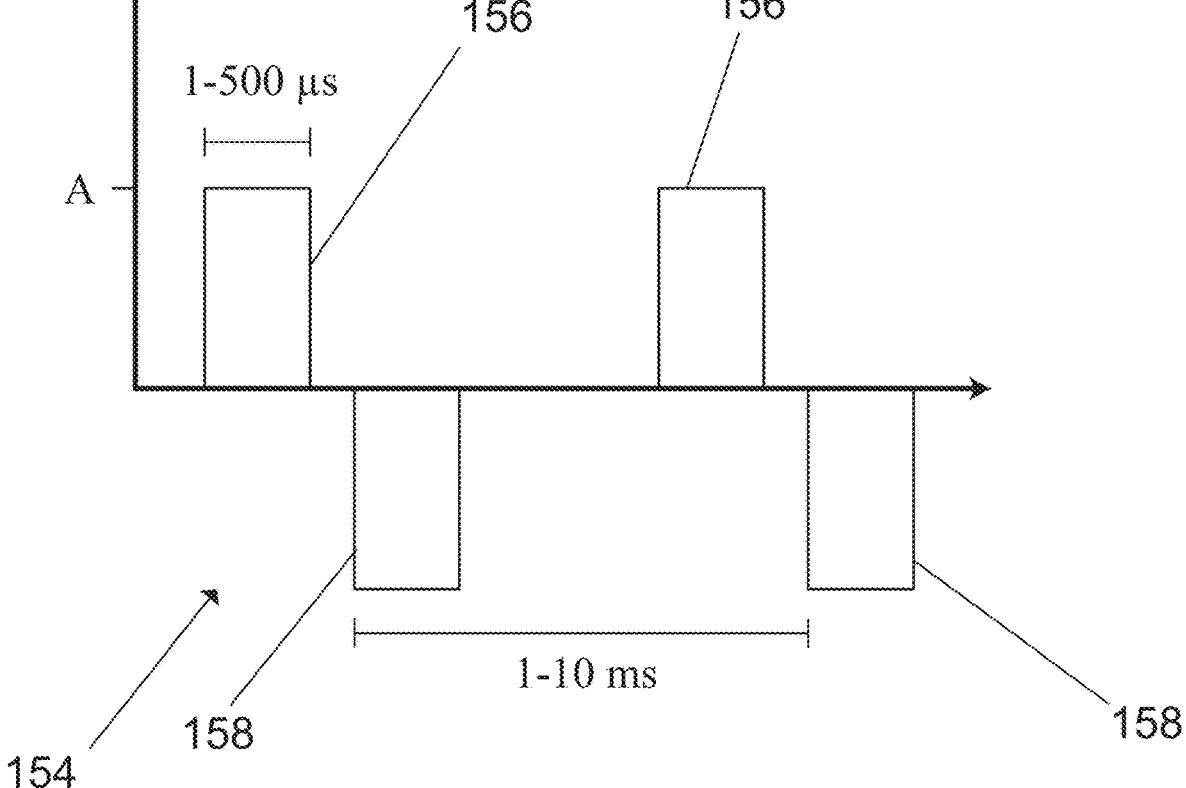
FIG. 6B illustrates a graph depicting bi-phasic doublet stimulus pulses at an arbitrary amplitude according to one embodiment.
Figure 6C:
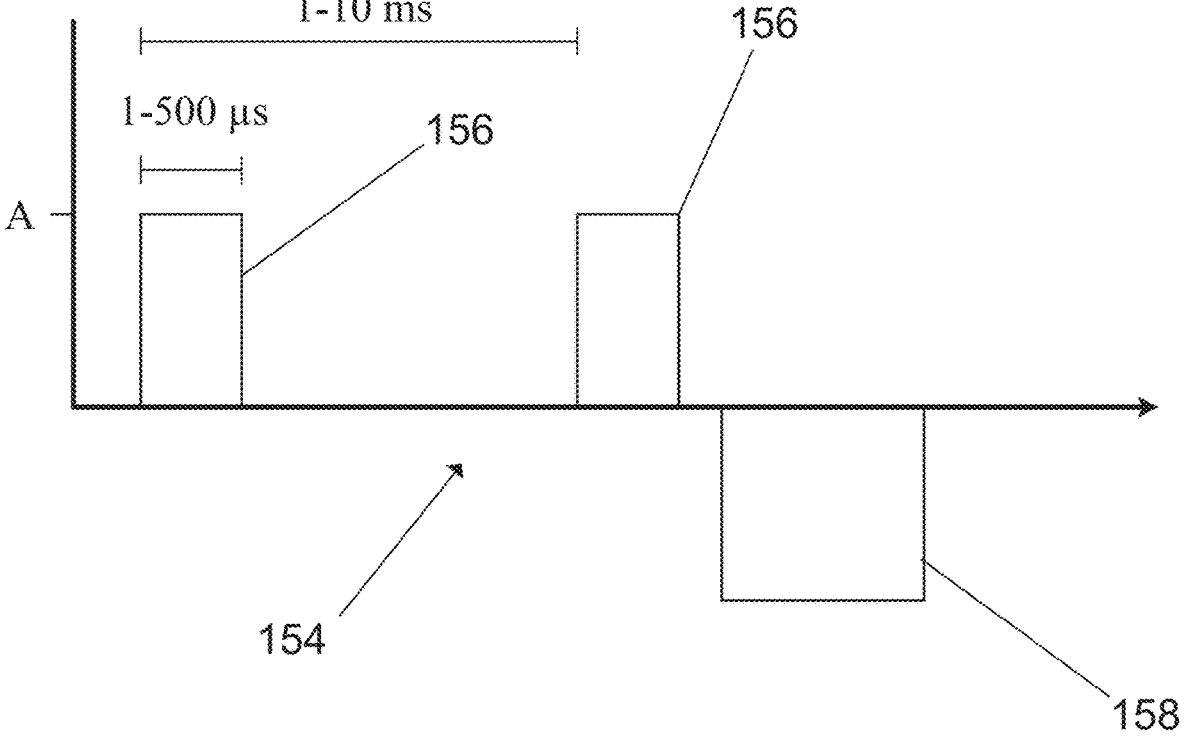
FIG. 6C illustrates a graph depicting using a single charge balancing pulse following a doublet stimulus pulse at an arbitrary amplitude according to one embodiment.
Figure 6D:
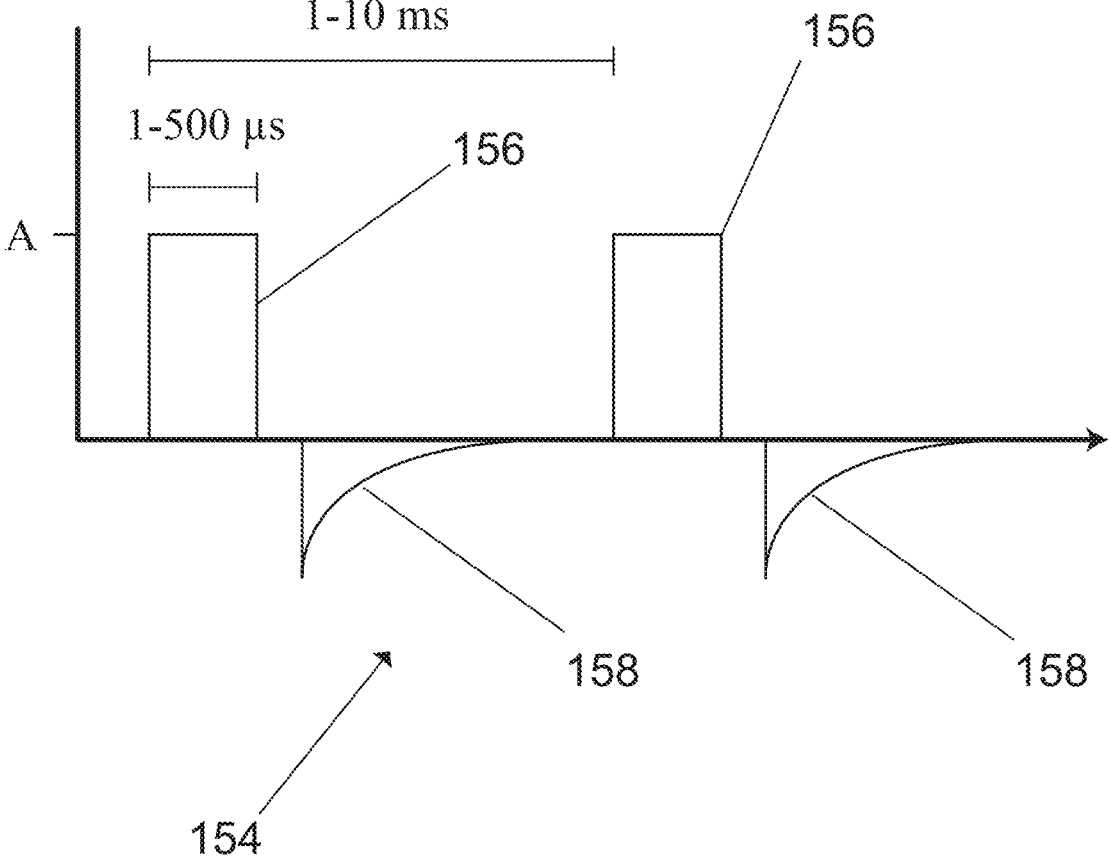
FIG. 6D illustrates a graph depicting exponentially rising charge balancing pulses following each pulse in a doublet pulse train at an arbitrary amplitude according to one embodiment.

In some embodiments, the doublet pulses 156 may be charge balanced individually, that is, each doublet pulse may be followed by a charge recovery pulse 158 that is equal duration but opposite polarity. See, e.g., FIG. 6B. In other arrangements, the doublet pulse may be charged balanced as a whole, such that a charge recovery pulse 158 that is equal in duration to the sum of the individual doublet pulse 156 durations. See, e.g., FIG. 6C. In other arrangements, the charge recovery pulse may be generated passively by AC coupling the stimulator output. Such an embodiment produces exponentially decaying charge recovery pulses 158 that are followed by each output pulse (e.g., each doublet pulse may include a passively generated charge recovery pulse), as shown in FIG. 6D. In some embodiments, the sub-system generates stimulus pulses, amplitudes, and/or trains sufficient to depolarize nerve fibers and elicit action potentials.

Safety Mechanisms

To ensure patient safety, in some embodiments, electrical energy is only delivered to the stimulating electrode or nerve probe 106 that is in contact with neural tissue when the impedance is less than 10 kOhm (e.g., less than 10 kOhm, less than 9 kOhm, less than 8 kOhm, less than 7 kOhm, less than 6 kOhm, less than 5 kOhm, less than 4 kOhm, less than 3 kOhm, less than 2 kOhm, less than 1 kOhm, etc.). In some embodiments, electrical energy is only delivered to the stimulating electrode or nerve probe 106 that is in contact with neural tissue when the impedance is between 0 and 10 kOhm (e.g., 0-1, 1-2, 2-3, 3-4, 4-5, 5-6, 6-7, 7-8, 8-9, 9-10 KOhm, impedances between the foregoing ranges, etc.).

In some embodiments, a system according to any of the configurations disclosed herein includes an impedance measurement sub-system. Such a sub-system can comprise a circuit that generates a sin-wave with said circuit coupled to a constant current source and further coupled to a set of electrodes. In some embodiments, the constant current source may comprise of a Howland current pump.

In some embodiments, the sin wave is generated using a microcontroller's digital to analog converter. In other arrangements, a microcontroller's pulse-width modulation output is used and coupled to a low-pass filter. In some arrangements, the low-pass filter comprises passive components, while in other arrangements the filter comprises active components (e.g., an active filter).

In some embodiments, the impedance measurement sub-system includes an instrumentation amplifier coupled to the electrode path used to measure impedance. Impedance measurement can be calculated within the sub-system and sent (e.g., digitally) to the microcontroller. In other arrangements, the microcontroller samples the analog impedance value and converts the value to a digital representation internally.

In some embodiments, when an electrode is properly placed in contact with neural tissue, the electrode-tissue impedance will be smaller than the impedance when the electrode is not in contact with tissue. In some arrangements, the impedance is such circumstance is typically less than 10 kOhm (e.g., 0-1, 1-2, 2-3, 3-4, 4-5, 5-6, 6-7, 7-8, 8-9, 9-10, 3-8, 1-10, 4-8 KOhm, impedances between the foregoing ranges, etc.). Such lower resistance can exist because healthy, internal human tissue provides a relatively low resistance electrical pathway through which electrical current may pass. In some embodiments, resistances exceeding a threshold value (e.g., 10 kOhm) can be an indication of improper placement of the electrode. In some arrangements, the system is configured of recognizing values exceeding such a threshold.

In some embodiments, the system is configured to periodically detect the impedance during the continuous application of electrical stimulation. In some arrangements, if relatively high impedance is detected (e.g., high compared to a threshold level or upper limit), the system can be designed and otherwise configured to pause the application of continuous electrical stimulation and enable an indicator 118 on the housing 114 to alert the operator. In other arrangements, the system is configured to terminate (e.g., automatically stop) the stimulus output and/or prompt the user. In some embodiments, the indicator comprises a visual indicator; however in other embodiments, the indicator can include an auditory indicator and/or any other type of indicator, either in addition to or in lieu of visual indication.

As noted herein, to further enhance patient safety, in some embodiments, the output of the system is capacitively coupled to prevent net DC charge inflow into the electrode tissue interface.

Nerve Probe and Electrodes

A nerve probe 102 can be used to probe tissue to test for excitability. Bodily tissues such as nerves may conduct action potentials towards a muscle when probed using physical means, electrical stimulation and/or the like resulting in a muscle twitch, reflex or contraction. According to some embodiments, the devices and systems disclosed herein include a nerve probe physically coupled to the housing and electrically coupled to the stimulus output stage sub-system.

In some embodiments, the nerve probe comprises a single conductive element in the shape of a cylinder or rod that extends from the housing's distal end. In other embodiments, the shape of conductive element can vary. In some arrangements, the nerve probe is entirely (or nearly entirely) electrically insulated except for a small de-insulated component on the distal aspect of the nerve probe. For example, the majority of the nerve probe is electrically insulated (e.g., over 70%, 70-100%, 80-95%, etc.). The area of de-insulation can range from 0.1 mm$^2$ to 10 mm$^2$ (e.g., 0.1-0.5, 0.5-1, 1-2, 2-3, 3-4, 4-5, 5-6, 6-7, 7-8, 8-9, 9-10, 2-8, 1-9, 4-8 mm$^2$, areas within the foregoing ranges, etc.). In some embodiments, the insulation may be manually configured to de-insulate the probe by a varying percentage, such as, for example 1-30% (e.g., 1-2, 2-3, 3-4, 4-5, 5-10, 10-15, 15-20, 20-25, 25-30%, percentages within the foregoing ranges, etc.).

In some arrangements, the single conductive element functions as a cathode or stimulating electrode. In such an arrangement, an appropriate return path for current to flow is necessary. In some embodiments, the return path may be provided by connecting a return electrode to the nerve port 106. The return electrode can comprise a needle, a surface pad, another conductive element and/or the like.

In some embodiments, the nerve probe comprises a plurality of conductive elements. In some arrangements, one or more of the conductive elements can be designed and otherwise configured to function as a return electrode or anode, while one or more of the conductive elements can be designed and otherwise configured to function as cathodes or stimulating electrodes.

In some embodiments, the conductive elements comprise one or more metals or alloys (e.g., stainless steel, platinum, iridium, gold, etc.). In one arrangement, the conductive elements comprise platinum or 90/10 platinum iridium, gold. The conductive elements can comprise any other conductive metal, alloy and/or other material, as desired or required.

In some embodiments, the length of the conductive elements is 0.5 to 10 cm (e.g., 0.5-1, 1-2, 2-3, 3-4, 4-5, 5-6, 6-7, 7-8, 8-9, 9-10, 3-7, 5-10, 0-5 cm, lengths within the foregoing ranges, etc.). However, the length of the conductive elements can be greater than 10 cm to meet the requirements of a particular application or use. The diameter or other cross-sectional dimension of the conductive elements can be 0.1 to 5 mm (e.g., 0.1-0.2, 0.2-0.3, 0.3-0.4, 0.4-0.5, 0.5-1, 1-2, 2-3, 3-4, 4-5, 0.1-2, 1-2 mm, values within the foregoing ranges, etc.). However, the diameter (or other cross-sectional dimension) of the conductive elements can be greater than 5 mm and/or to meet the requirements of a particular application or use.

In some embodiments, the system does not include a nerve probe. Instead, for such configurations, the system can rely on an appropriate electrode apparatus to be connected to the nerve port. In some arrangements, the electrode apparatus comprises monopolar or bipolar catheter type apparatus. Such arrangements can be particularly advantageous in peri-operative scenarios where the lead may be placed intraoperatively and, due to its shape, may be easily removed from a closed incision or percutaneous access point.

In some embodiments, a nerve cuff electrode apparatus is connected to the nerve port. A cuff electrode can be particularly advantageous in intraoperative settings where a dissected nerve is easily accessible. However, as discussed herein, for any embodiments disclosed in this application, the electrode can include a configuration other than a cuff electrode.

Certain embodiments of a nerve cuff electrode apparatus 10 are illustrated in FIGS. 7 to 11. As shown, the nerve cuff electrode apparatus 10 can comprise a carrier body 12. In some embodiments, the carrier body 12 and/or other portions of the apparatus 10 comprise one or more insulative materials, such as, for example, silicone rubber, other elastomeric and/or polymeric materials and/or any other materials. One or more materials can be used, either in lieu of or in addition to rubber, such as, for example and without limitation, thermoplastic elastomers, elastomeric polyurethanes and/or the like. In some embodiments, the material(s) included in the apparatus are flexible so as to permit bending without breaking, fracturing and/or other damage brought about by movement during use.

In some embodiments, the electrode apparatus 10 is arranged in a longitudinal manner with the length being considerably longer than the width. For example, in some embodiments, the ratio of the length to width of the electrode apparatus 10 can be between 1:1 to 20:1 (e.g., 2:1, 3:1, 4:1, 5:1, 6:1, 7:1, 8:1, 9:1, 10:1, 15:1, 20:1, ratios within the foregoing ranges, etc.). In some embodiments, electrode apparatus 10 comprises two ends, a head portion 16 and a tail portion 26.

Figure 7A:
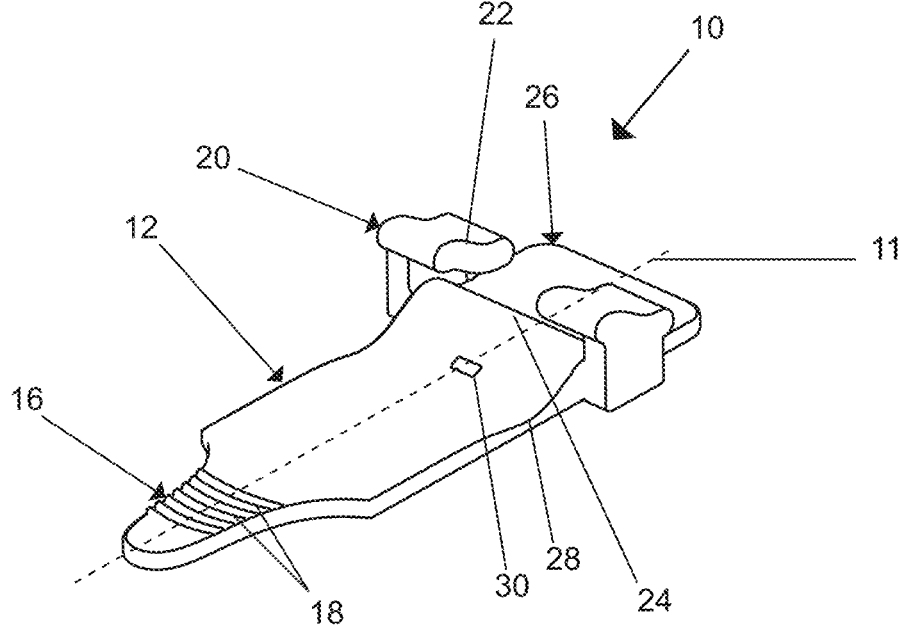
FIG. 7A illustrates a perspective view of an embodiment of the apparatus where the electrode configuration is monopolar with a single electrode pad being present in the thickest portion of the carrier according to one embodiment.

As shown in FIG. 7A, the apparatus 10 can include a longitudinal axis 11 that extends longitudinally or lengthwise along the apparatus 10. The length of the device can be 20 to 80 mm. The width of the apparatus 10 (e.g., the dimension perpendicular to the longitudinal axis 11) can be 5 to 30 mm. Thus, in some embodiments, the length of the apparatus 10 is 2 to 5 times the width of the apparatus. However, in other arrangements, the width can be equal or greater than the length. In some embodiments, the thickness of the head portion 16 can be 1.5 mm. In some arrangements, the thickness can range from 0.1 mm to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5 mm, thicknesses within the foregoing ranges, etc.), as desired or required.

The head portion can contain a tapered end 16 that is rounded and contains gripping structures 18 that aid a surgeon in handling the electrode apparatus. In some embodiments, the gripping structures 18 are present on either side of the tapered end of the carrier. However, in other embodiments, gripping structures 18 are included only on one side. In some embodiments, the gripping structures 18 include ridges, recesses, protrusions and/or the like. In some embodiments, such structures 18 are formed into the surface or body of the apparatus, and thus, form a unitary structure with the portion in which they are included. For example, the ridges or other structures 18 can be molded (e.g., injected molded) together with the main portion of the apparatus. However, in other arrangements, the gripping structures 18 are separate from the main portion of the apparatus and/or are created after the main portion of the apparatus is formed (e.g., via one or more connections technologies or methods, by removal of material, etc.). In some embodiments, the gripping structures are replaced by a through-hole or multiple holes where one or more sutures can be threaded.

With continued reference to FIG. 7A, the tail portion 26 of the apparatus 10 can be non-tapered. However, in other configurations, at least a portion of the tail portion 26 is tapered, as desired or required. In some embodiments, the tail portion 26 comprises rounded or curved corners to facilitate handling of the apparatus. In some embodiments, the tail portion comprise one or more areas that are substantially thicker than the head portion to encompass a through-hole in the longitudinal axis 11 that allows for placement of electrode lead wires. In some embodiments, the thicker area can be greater than 1 times thicker than the head portion (e.g., 1 to 5, 1 to 10, 1 to 20 times thicker, etc.), but not thicker than the grooved body 24. In some embodiments, the thickening of the tail portion may be in the opposite direction from the thickening of the grooved body 24 and can also include a through-hole in a diagonal direction from the bottom face of the tail portion to the midbody to allow accommodation of an electrode lead wire.

As shown in FIG. 7A, the mid portion of the carrier can include two features: a grooved body 24 and a winged locking mechanism 20. The grooved body 24 can be structured and configured so that when a surgeon places a nerve on the electrode apparatus 10, the nerves longitudinal axis is perpendicular (e.g., substantially perpendicular) to the electrode's longitudinal axis 11, with the nerve itself naturally settling in the thinner mid-portion 28 of the grooved body, in some embodiments.

In some embodiments, the winged locking mechanism may be positioned in various locations longitudinally and may include more than one set (e.g., 2 wings) at each location. In some embodiments, the locking wings are positioned in a staggered arrangement.

The thinner mid-portion 28 of the grooved body 24 can be shaped to facilitate placement of a nerve and to wrap or bend the head portion 16 of the apparatus around (e.g., at least partially around) the nerve. In terms of nerve placement, in some embodiments, the thinner mid-portion 28 follows the shape of a semi-circle or other circular or curved shape. This can help prevent the nerve tissue from sliding off the electrode apparatus 10. The radius of curvature of the thinner mid-portion 28 can range from 1 to 10 mm (e.g., 1-2, 2-3, 3-4, 4-5, 5-6, 6-7, 7-8, 8-9, 9-10, 2-8, 4-8, 5-10 mm, radii within the foregoing ranges, etc.). In some arrangements, the radius of curvature is greater than 10 mm (e.g., 10-15, 15-20, 10-20, 10-50 mm, radii between the foregoing, greater than 50 mm, greater than 100 mm, etc.), as desired or required.

In some embodiments, the thinner mid-portion 28 of the grooved body 24 is flat and tangent to the head portion 16 of the electrode apparatus 10. The thickness of the mid-portion can range from 0.1 mm to 5 mm. In some arrangements, such as the desired curved shape described above, the thinnest section can be 0.1 mm (e.g., 0.05 mm to 2 mm). In some embodiments, the thinnest section can be 10% (e.g., 5-25%) of the thickest section of the head portion 16 of the electrode apparatus 10. The thickness of the mid-portion 28 can be designed and otherwise configured to adjust for how flexible the apparatus is when the head portion 16 is wrapped around a nerve.

In some embodiments, the grooved body 24 of the mid portion 28 comprises of a uniform or a generally uniform thickness. That is, the mid portion is of similar thickness as the connected head portion 16, providing a flat plane. In some arrangements, the carrier may include electrodes placed on the underside of the carrier 12. In some embodiments, the locking mechanisms may be engaged in a reverse orientation such that when carrier is folded, the head portion 16 engages the locking mechanism from the direction of the tail portion.

In some arrangements, the desired curved shape described herein follows the shape of a semi-circle or other partially rounded or curved shape with a uniform thickness to that of the head portion 16. In some arrangements, the base of the semi-circular groove can protrude, at least partially, below the plane of the head portion 16 to create a larger circumference for nerve placement.

In some embodiments, the groove also contains one or more conductive electrodes 30 that may be present in various configurations as outlined further below. In some arrangements, the purpose of the groove is to facilitate interfacing with a nerve while preventing or limiting slippage of the nerve. Such a configuration can also, in some embodiments, facilitate contact between the nerve and the conductive electrode(s) 30. Once the nerve is in place, the surgeon or other practitioner can grasp the tapered head portion 16 of the carrier (e.g., using either forceps, his/her fingers, other devices or methods, etc.) and can wrap (e.g., at least partially) the nerve. In some embodiments, to lock the cuff in place, the tapered head portion 16 is placed underneath the winged locking mechanism 20. Since the electrode apparatus can advantageously be configured to accommodate different diameter nerves or nerve bundles, the surgeon or other practitioner can apply as much or as little wrapping pressure to sufficiently cover the nerve. To securely lock the tapered head portion 16, the surgeon can laterally deflect the winged locking tabs 22 and place the tapered head portion 16 underneath them and then release the tabs.

In one embodiment, the carrier is molded in a flattened or opened position. For example, the carrier can be bent and placed underneath the locking tabs 22. In some embodiments, a natural bias force exists that presses or otherwise urges the tapered head portion 16 against the locking tabs 22 preventing the tapered portion from sliding further down the longitudinal axis 11 of the apparatus and potentially compressing the interfaced nerve.

In some arrangements, when a surgeon or other practitioner is finished using the electrode apparatus 10, he or she can laterally deflect the locking tabs 22, and the tapered head portion 16 of the carrier can be configured to spring back due to the bias force pushing back to its original flat or open conformation. Such a feature can allow for quick release of the interfaced nerve. Accordingly, the surgeon or other practitioner can then pull the nerve cuff from the tail end 26 and slide it from beneath the interfaced nerve without damaging it.

With continued reference to FIG. 7A, a single conductive electrode pad 30 is placed on the grooved portion of the carrier 24. In some arrangements, this is the thickest portion of the carrier and serves one or more purposes (e.g., to provide an insulative barrier to prevent current spread, to provide stiffness to reduce the probability of electrode pad delamination during the time it is flexed around the nerve and then released, etc.).

Figure 7B:
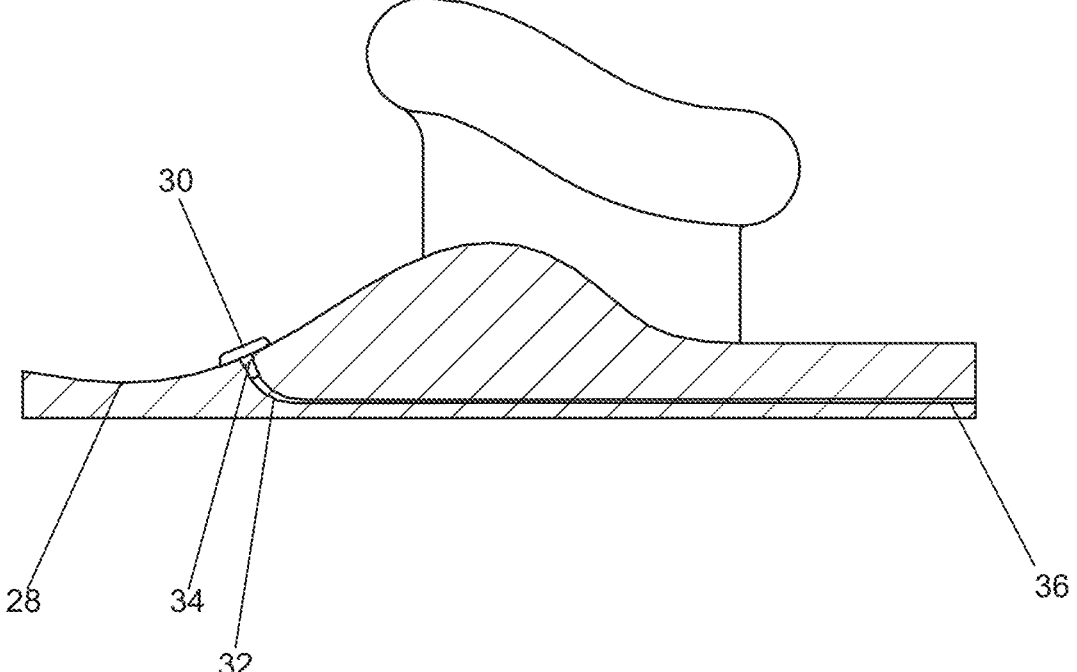
FIG. 7B illustrates a cross-sectional view of the carrier showing the attachment of the single electrode pad to a lead wire with the lead wire being externalized from the carrier at the tail portion according to one embodiment.

In some embodiments, the electrode pad 30 comprises a monopolar single contact configuration. A lead wire 32 can be coupled to the electrode pad 30 (e.g., via laser or resistance welding, crimping, using other technologies or techniques, etc.). In some embodiments, a physical conductive connection is made with the electrode pad. FIG. 7B illustrates a cross-sectional view through a midplane of the electrode apparatus 10. As shown, an electrode pad 30 is coupled to a lead wire 32. The tail end of the lead 36 can be externalized from the electrode apparatus.

Figure 8A:
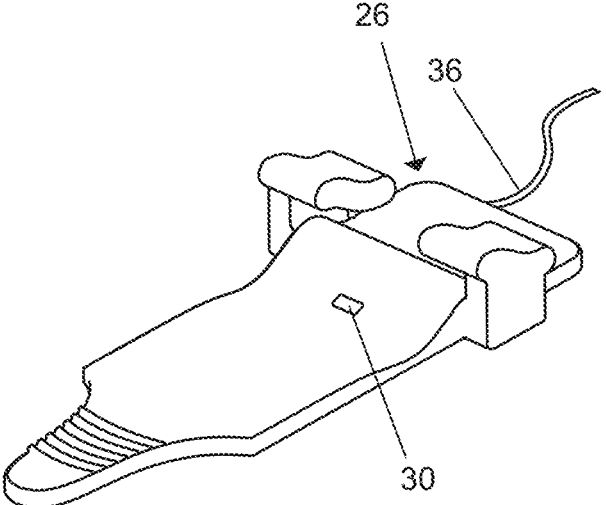
FIG. 8A illustrates a perspective view of the apparatus with lead cable exiting the carrier along the longitudinal axis from the tail end of the carrier according to one embodiment.
Figure 8B:
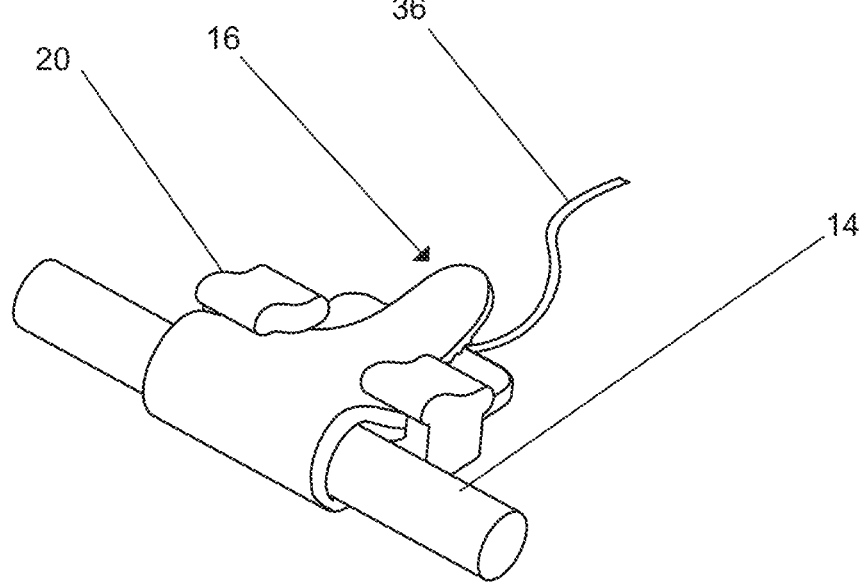
FIG. 8B illustrates a perspective view of the locking mechanism being engaged with the carrier being wrapped around a tubular structure according to one embodiment.
Figure 8C:
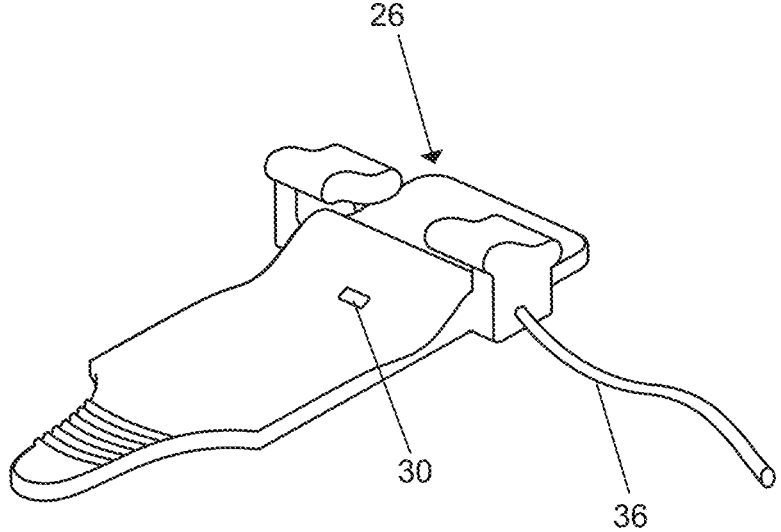
FIG. 8C illustrates a perspective view of the apparatus with lead cable exiting the carrier perpendicular to the longitudinal axis according to one embodiment.

According to some embodiments, as shown in FIG. 8A, the tail end of the lead 36 exits the apparatus from the tail end of the carrier 26, parallel or generally parallel to the longitudinal axis of the carrier. In some arrangements, when interfaced with a nerve 14 (see FIG. 8B), the apparatus 10 with secured head portion 16 using the winged locking mechanism 20 has the lead wire positioned conveniently away from the nerve. Accidental pulling or movement of the lead wire can move the interfaced nerve 14 in a direction close to perpendicular to its longitudinal axis. In another embodiment, as shown in FIG. 8C, the tail end of the lead wire 36 can exit perpendicular to the longitudinal axis 11 of the carrier 12.

Figure 9A:
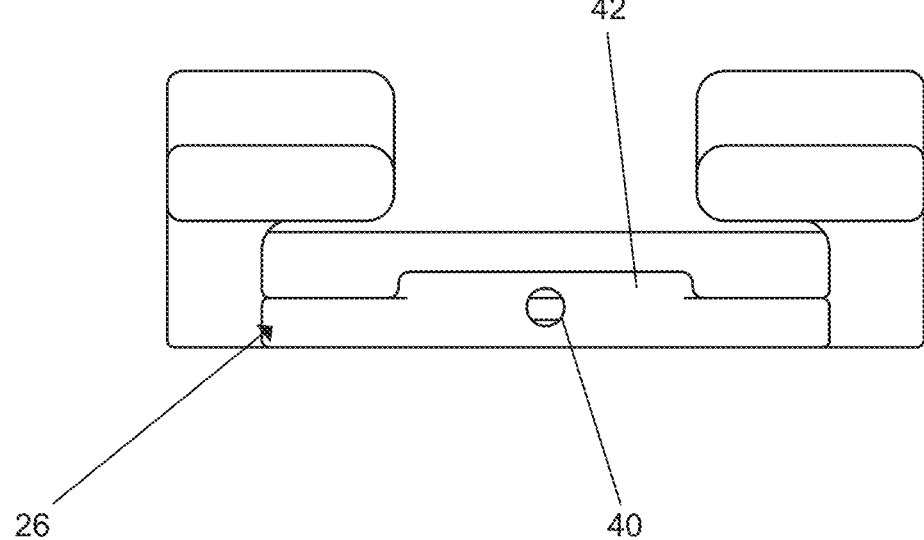
FIG. 9A illustrates a rear view of the apparatus showing a single through-hole starting at the tail portion of the apparatus and used to place an electrode according to one embodiment.
Figure 9B:
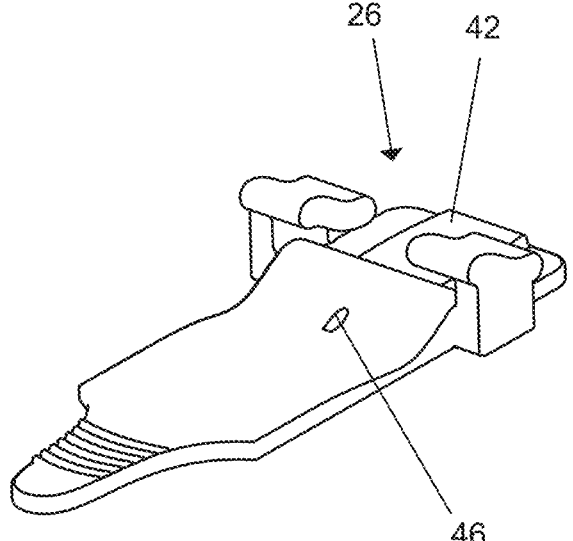
FIG. 9B illustrates a perspective view of the apparatus shown in FIG. 3A and highlights the exit portion of the through-hole.

In some arrangements, as shown in FIG. 9A, the electrode pad 30 and lead wire 32 are connected to the carrier via a through-hole 40. In some embodiments, the through-hole is cut or otherwise created in a thickened portion 42 of the tail end of the carrier 26. In some embodiments, as depicted in FIG. 9B, the through-hole can be a straight line from the tail end of the carrier 26 and can exit through a hole or other opening 46 of the grooved body 24.

In some embodiments, the through-hole containing lead wire 32 comprises one or more through-holes with the angle between their longitudinal axis varying. Such a configuration can result in a chamber where a lead wire 32 can be placed similar to what is shown in FIG. 7B. In some arrangements, the longitudinal axes of the through-holes are angled at 45 degrees (e.g., 30-60 degrees) to one another. In some arrangements, such an angle is between 0 and 90 degrees (0-10-10-20, 20-30, 30-40, 40-50, 50-60, 60-70, 70-80, 80-90, 45-90, 45-60, 15-45 degrees, angles within the foregoing ranges, etc.), as desired or required.

In some embodiments, the electrode pad 30 is secured to the apparatus via a secondary enlarged electrode area 34 that is substantially larger than the through-hole in which the lead wire is inserted. In some embodiments, the electrode pad 30 is protruding relative to the adjacent portions of the apparatus. In other arrangements, the electrode pad may be insert molded flush or recessed relative to the adjacent portions of the apparatus. In other arrangements, the electrode pad is secured by an enlarged secondary electrode area 34 and/or is flush or recessed relative to the adjacent portions of the apparatus, as desired or required.

Figure 10A:
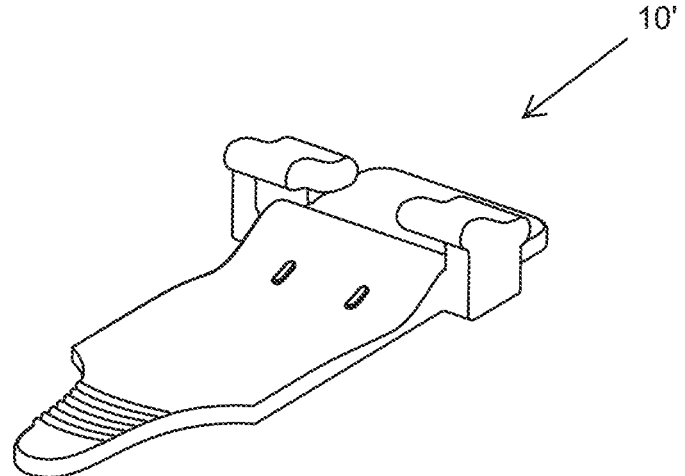
FIG. 10A illustrates a perspective view of one embodi-ment of the apparatus where the electrode configuration is bipolar with two electrode pads according to one embodi-ment.

According to some embodiments, as illustrated in FIG. 10A, the electrode contact pads of an electrode apparatus 10' are not limited to a single conductive pad. Instead, as shown, the apparatus can include two (or more) pads placed in a bipolar configuration (e.g., in a similar manner to the single electrode pad 30). The spacing between bipolar pads can be 5 mm. In some arrangements, the spacing can range from 0.1 mm to 5 mm or from 0.1 mm to the width of the electrode apparatus.

Figure 10B:
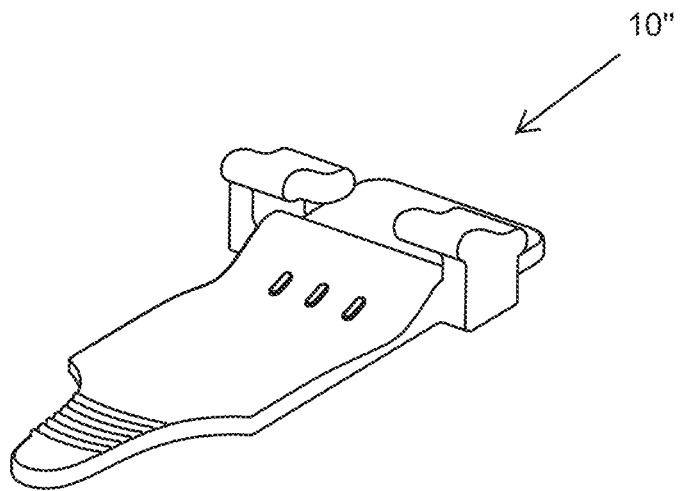
FIG. 10B illustrates a perspective view of one embodi-ment of the apparatus where the electrode configuration is tripolar with three electrode pads according to one embodi-ment.

For more precise or selective stimulation of axons within a nerve, a tripolar electrode pad configuration may be used, as shown in the electrode apparatus 10″ of FIG. 10B. The spacing between adjacent electrode pads may range from 0.1 mm to 2 mm. In some arrangements, a plurality of more than three electrode pads can be introduced with contact spacing ranging from 0.1 mm so long as the electrode pads fit into the width of the apparatus.

Figure 11A:
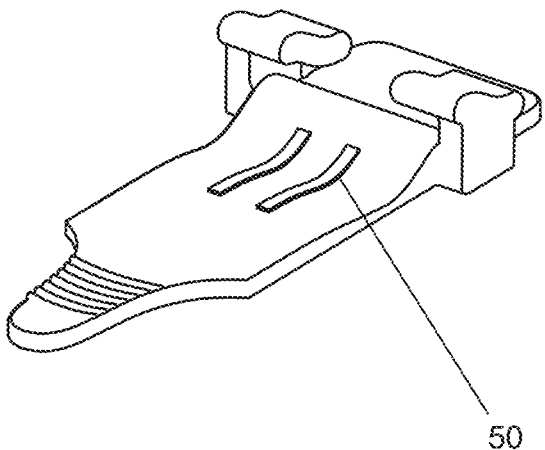
FIG. 11A illustrates a perspective view of one embodi-ment of the apparatus where the electrode configuration is bipolar with two electrode pads that are made from metallic foil and oriented in a longitudinal direction along the grooved portion of the carrier according to one embodiment.
Figure 11B:
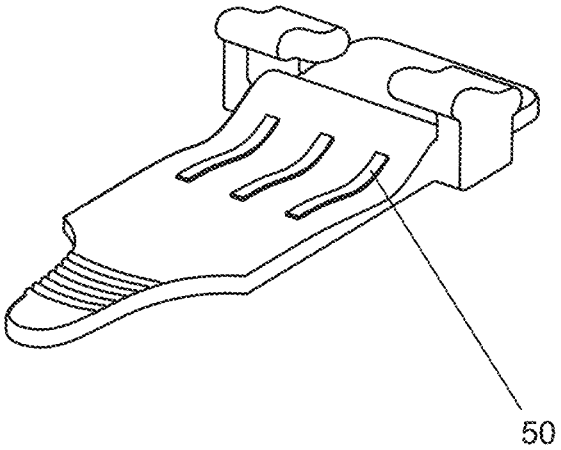
FIG. 11B illustrates a perspective view of one embodi-ment of the apparatus where the electrode configuration is tripolar with three electrode pads that are made from metal-lic foil and oriented in a longitudinal direction along the grooved portion of the carrier according to one embodiment.

In yet other embodiments, as illustrated in FIGS. 11A and 11B, electrode pads can be in the configuration of a conductive electrode strip 50 and either printed on the carrier, glued to the carrier using adhesive and/or disposed on the carrier using some other method or technology. In some embodiments, the electrode pads comprise metallic foil (e.g., platinum iridium 90/10) and arranged in a bipolar configuration (FIG. 11A). In some embodiments, the metallic foil can comprise gold and/or any other conductive material, either in addition to or in lieu of platinum iridium, as desired or required. In some embodiments, as depicted in FIG. 11B, a tripolar configuration of foil strips can be used. The spacing between adjacent strips can be similar to the spacing between electrode pads described above.

Figure 11C:
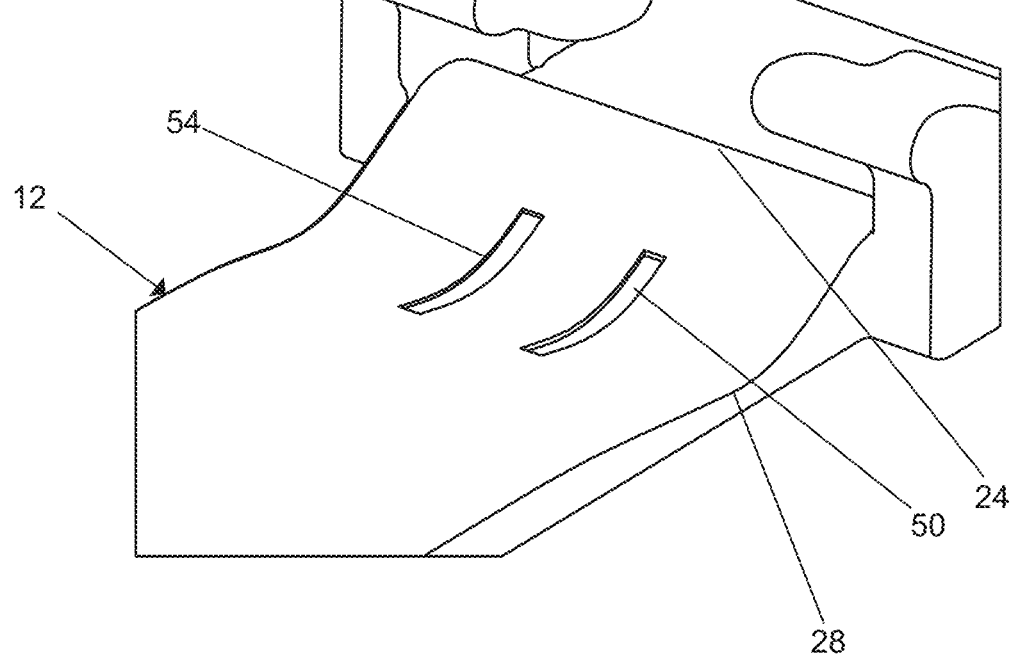
FIG. 11C illustrates a closer perspective view of one embodiment of the apparatus where the electrode configu-ration is bipolar with two electrode pads that are made from metallic foil and oriented in a longitudinal direction along the grooved portion of the carrier according to one embodi-ment.

The conductive electrode strip 50 can be embedded within the carrier body 12, as shown in FIG. 11C. In some embodiments, the carrier comprises laser cut windows or other openings 54 to at least partially expose the metal contacts and permit interfacing with tissue. According to some arrangements, the majority of the foil is placed within the thinner mid-portion of the grooved body 28 or grooved body 24 of the carrier 12. This can be particularly helpful with respect to conductive strip electrode placement, in some embodiments, to minimize or reduce potential delamination when the head portion 16 is wrapped around the nerve 14 and interfaced with the winged locking mechanism 20. The conductive electrode strips can be configured in a variety of ways including an array arrangement of a plurality of electrode strips (more than 3, e.g., 4, 5, 6, etc.), as desired or required for a particular application or use. In some embodiments, as discussed in greater detail herein, the electrode apparatus 10 can be used to record tissue or nerve activity as well deliver electrical stimulation.

Figure 12:
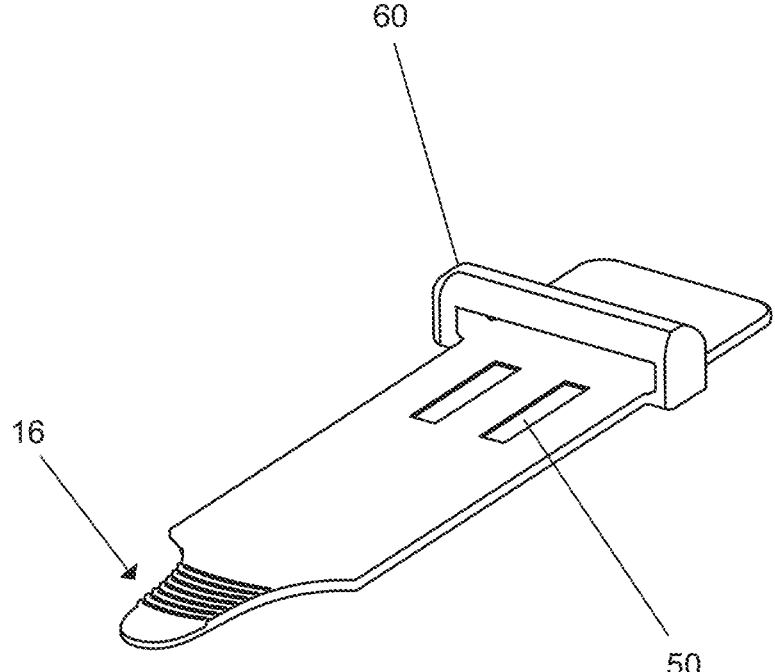
FIG. 12 illustrates a perspective view of an embodiment where the locking mechanism is a circular strap according to one embodiment.

FIG. 12 illustrates yet another embodiment of an electrode apparatus. As shown, the locking apparatus can include a strap 60 that allows a surgeon or other practitioner to pull the head portion 16 of the carrier body 12 under the strap 60 (e.g., using forceps or some other tool). Such movement can permit the surgeon or other practitioner to size the carrier body 12 to fit a nerve appropriately. As in previous embodiments, the molding of the electrode apparatus 10 in a flat configuration can create a biasing force (e.g., to press upwardly on the strap when the head portion 16 of the carrier is threaded under the strap). Such a biasing force can help prevent or reduce the likelihood of the head portion 16 from undesirable movement. Additionally, the friction of the elastomeric material can further prevent or reduce the likelihood of movement of the head portion 16 of the carrier body 12 while engaged with the strap 60. In some embodiments, in order to remove the electrode apparatus from the nerve, the surgeon or other practitioner may cut or otherwise compromise the strap 60. This can release the head portion 16, and the biasing force can allow the electrode apparatus 10 to return to a flat or generally flat conformation.

In some embodiments, a conductive electrode strip 50 can be included in any of the electrode configurations disclosed herein. The strips can extend to the location of the strap 60 in one direction and to the tapered portion of the head portion 16 of the apparatus. The conductive strips 50 can be attached or otherwise coupled to the electrode carrier body 12 (e.g., as previously described). The electrodes may not be limited to the described strips but may also include other electrode embodiments described previously.

Figure 13:
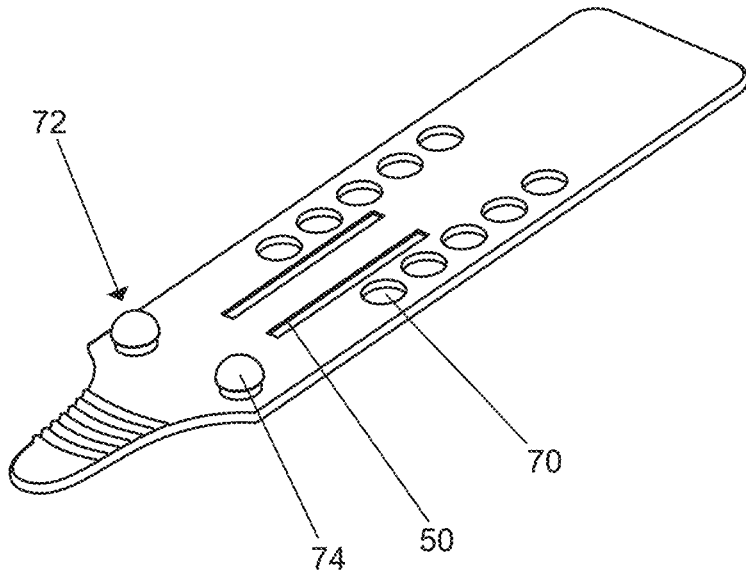
FIG. 13 illustrates a perspective view of an embodiment where the locking mechanism is a set of paired apertures arranged longitudinally along the carrier and one pair of protrusions or buttons that engage with the apertures accord-ing to one embodiment.

In some arrangements, as shown in FIG. 13, the locking apparatus includes one or more paired apertures 70 and one pair of corresponding protrusions 72 or buttons with a surface protrusion (e.g., with a diameter that is larger than the aperture). The apertures can range in diameters (or other cross-sectional dimensions) from 1 to 10 mm (e.g., 1-2, 2-3, 3-4, 4-5, 5-6, 6-7, 7-8, 8-9, 9-10, 2-8, 4-8, 1-5, 5-10 mm, dimensions within the foregoing ranges, etc.). However, the diameters or other cross-sectional dimensions can be greater than 10 mm or smaller than 1 mm, as desired or required for a particular application or use. The corresponding paired buttons or protrusions 72 can include a cap 74 (e.g., a hemi-spherical cap) with a diameter or other cross-sectional dimension that may be equal to or larger than the paired aperture 70. In some embodiments, the protrusions comprise a cylindrical (or generally cylindrical) section that is attached to the carrier body 12 and may be smaller than the hemi-spherical cap 74.

In some embodiments, one or more different locking mechanisms can be combined such that the head and tail ends are fastened more securely. In some embodiments, the head portion 16 is fastened with a winged mechanism at a given longitudinal position and additionally fastened with a secondary mechanism (e.g., of the same winged mechanism or other mechanism), to provide additional locking strength in securely holding the head portion. The surgeon or other practitioner can determine whether using additional locking mechanisms is necessary at the time of use.

In any of the embodiments disclosed herein, one or more conductive electrode strips 50 can be included. The strip(s) can extend to the last pair or locking apertures 70 in one direction and to the paired buttons 72 in the other direction. The conductive strips 50 can be attached to the electrode carrier body 12 as previously described. The electrodes may not be limited to the described strips, but may also include other electrode embodiments described herein, as desired or required for a particular application or use.

In some embodiments, the carrier body 12 includes two or more sets of winged locking mechanisms (e.g., placed on either side of a symmetrical groove within the carrier body). In some arrangements, the carrier body can comprise one or more electrodes within the groove. The carrier body and accompanying locking mechanisms can be configured to engage with a second carrier body containing one or more electrodes. In some embodiments, the second carrier body is equal to or longer than the first carrier body. The second carrier body can be placed on top of the first carrier body and engage the locking mechanisms in order to secure a nerve placed between both carrier bodies.

The distance between the locking mechanisms and the groove can be variable or can be symmetrical with respect to the grooves center line. In some arrangements, the locking mechanisms include a strap or locking apertures as described herein.

Figure 14:
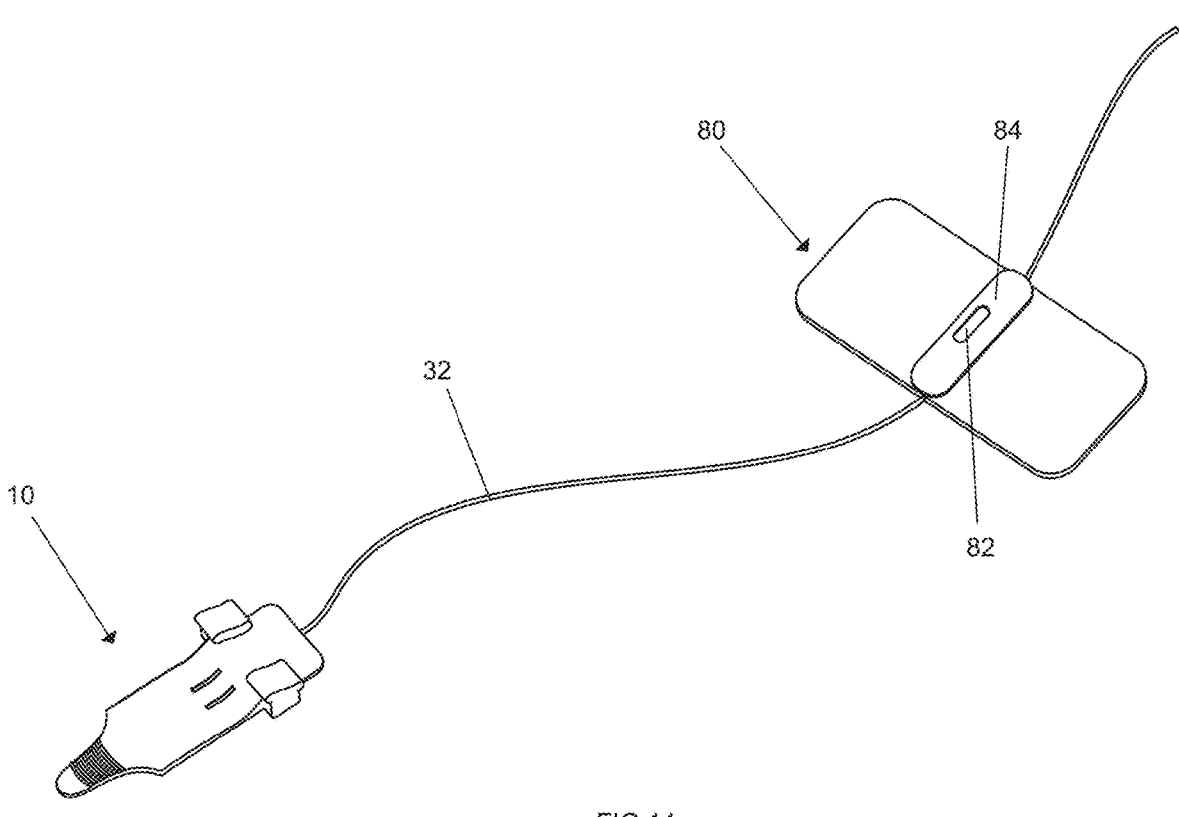
FIG. 14 illustrates a perspective view of an embodiment where an adhesive patch containing a visual indicator is coupled to the proximal end of the lead wire of the electrode apparatus according to one embodiment.

According to some embodiments, as shown in FIG. 14, an adhesive patch 80 is added to the lead wire 32. This can advantageously assist to stabilize the electrode apparatus 10 and prevent (or at least reduce the likelihood of) any inadvertent movement. By way of example, such movement can occur if a user accidentally pulls on the lead wire 32 or interacts with the wire during a surgical procedure. The adhesive patch 80 can be affixed (e.g., directly or indirectly)

to a part of the anatomy that is close to an incision or other area being treated or targeted.

In one embodiment, the adhesive patch 80 comprises carbon impregnated rubber or similar elastomeric materials. The elastomeric materials used for the patch 80 can be impregnated with conductive elements, as desired or required. In one embodiment, the adhesive patch 80 (e.g., one side of patch) can include a conductive adhesive gel (e.g. Parker Labs Tensive Conductive Adhesive Gel).

The adhesive patch 80 can include a rectangular shape. For example, in some embodiments, the patch is rectangular and comprises a length of 10 mm to 100 mm and a width of 5 mm to 50 mm. Thus, in some embodiments, the length of the adhesive patch 80 is 1.5 to 5 times the width of the adhesive patch 80. In one embodiment, the distance of the adhesive patch 80 to the electrode apparatus 10 may range from 50 mm to 300 mm. The size, orientation, dimensions and/or other properties of the patch can be different than disclosed herein. For example, in some arrangements, the shape of the patch is circular, oval, triangular, other polygonal, irregular and/or the like.

With continued reference to FIG. 14, the adhesive patch 80 can comprise one or more visual indicators 82, such as LEDs, to provide a status indication to the user. The indicator can be powered by a connected device such as an electrical stimulator or biological amplifier.

In some embodiments, the indication is configured to confirm proper delivery of stimulus pulses or high impedance of the electrode. In some arrangements, the indicator is configured to display, in the case of neuroregenerative therapy, a timer or stimulation amplitude levels. Any other data, information, confirmation and/or the like can be configured to be provided to the user, as desired or required.

In some embodiments, the adhesive patch 80 comprising one or more indicator(s) 82 (e.g., visual indicator(s)), can include a molded section 84 to embed the indicator. In some arrangements, the molded section includes additional circuitry (e.g., to power the indicator, to control the indicator, to provide other non-visual cues to the end user, etc.), as needed or required.

In some embodiments, the electrode apparatus 10 that is connected to the adhesive patch 80 comprises a single electrode contact resulting in a monopolar stimulation field. In some arrangements, the adhesive patch 80 can function as a return electrode for the monopolar stimulation field.

Figure 15A:
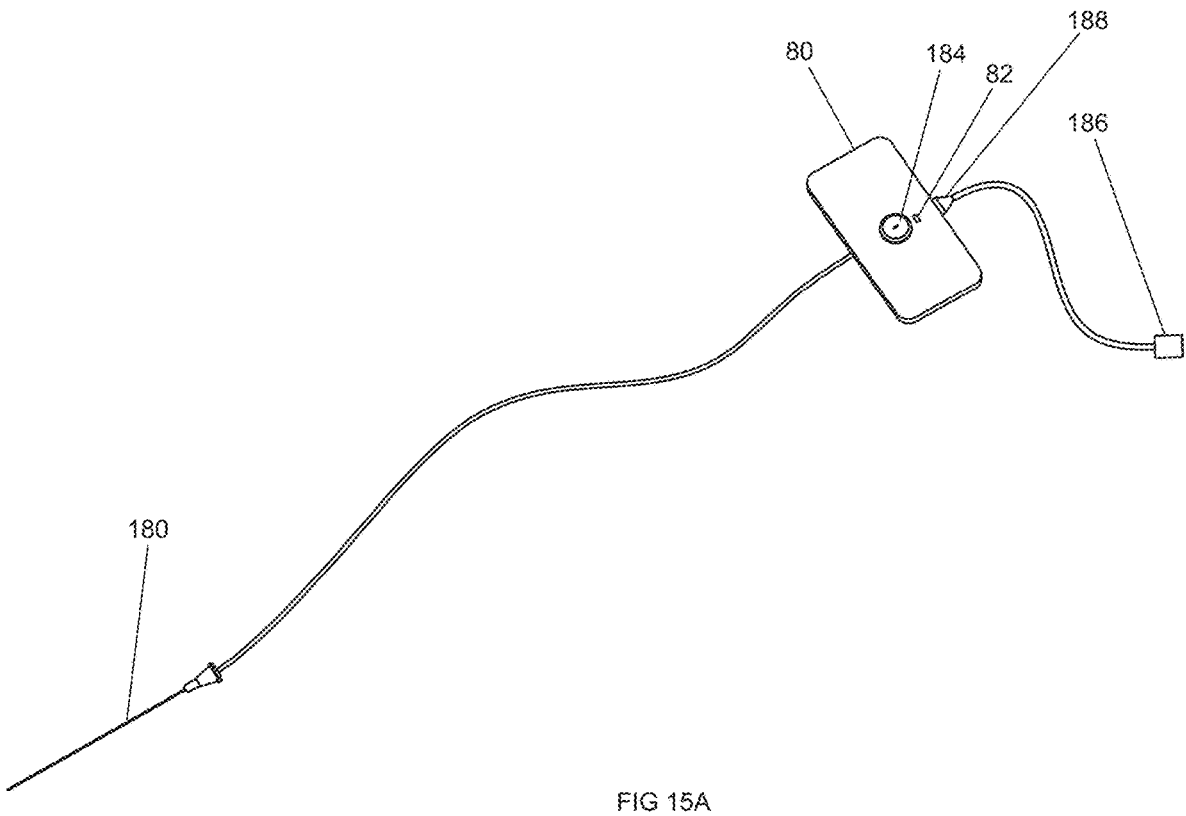
FIG. 15A illustrates a perspective view of an embodiment where an adhesive patch is coupled to a monopolar needle electrode with the patch serving as a return according to one embodiment.
Figure 15B:
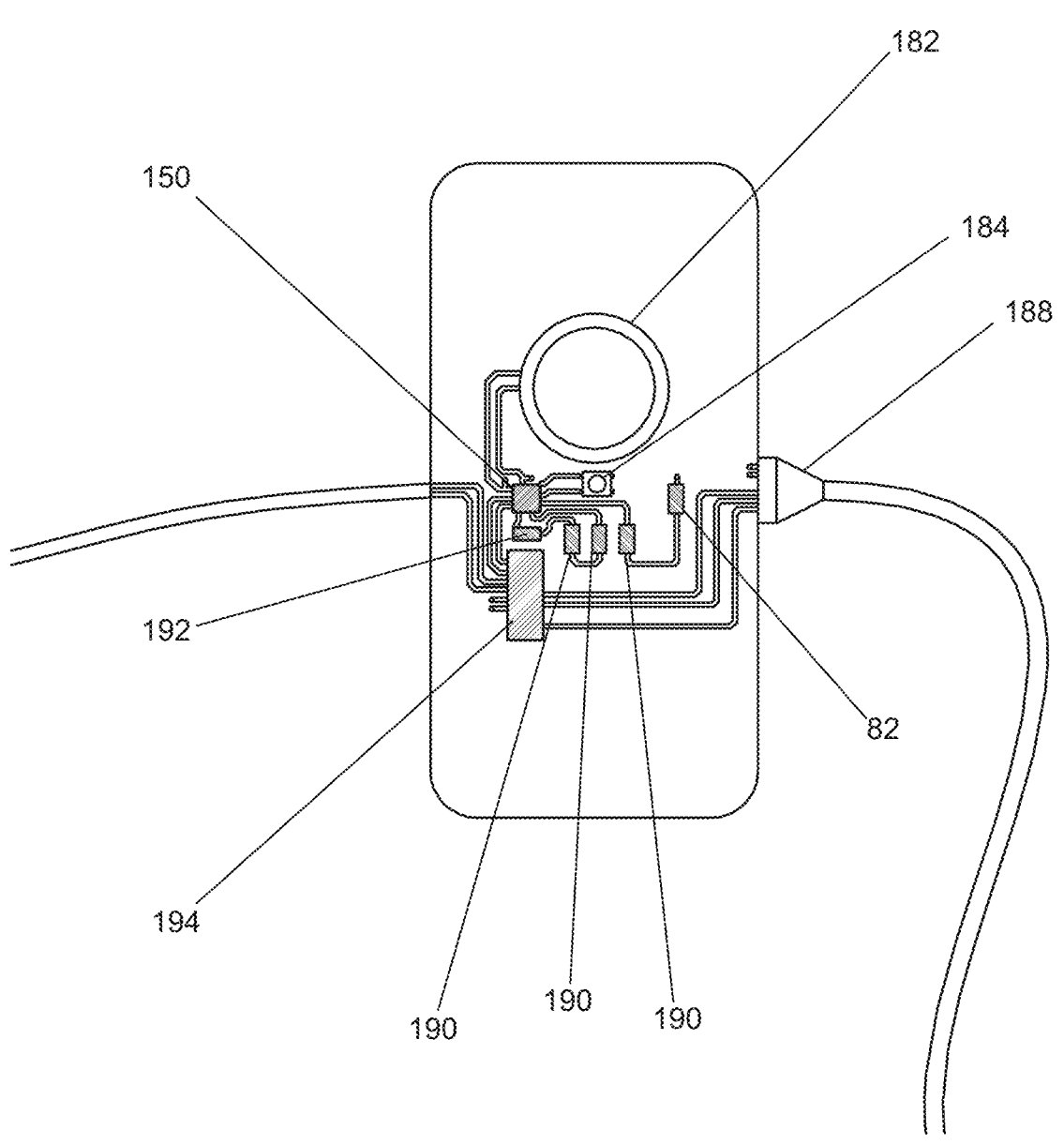
FIG. 15B illustrates a top view of the circuitry layer of the adhesive patch stimulator according to one embodiment.

In other arrangements, as illustrated in FIG. 15A, the adhesive patch 80 may connect to a monopolar electrode 180 that comprises a needle or needle-like apparatus. The adhesive patch 80 comprises circuitry to shape and deliver stimulus pulses to a connected electrode (see, e.g., FIG. 15B). In some arrangements, the patch and circuitry are powered by an included battery source 182. The circuitry can comprise elements similar to those described herein with reference to other embodiments for the electrical stimulation system, such as a microcontroller 150. In some embodiments, the circuitry comprises a time (e.g., 555 timer) or similar device, component or feature used to generate the stimulus pulses. In the embodiments discussed above, associative passive elements can also comprise the circuitry such as resistors 190 and capacitors 192, as needed or required.

In some embodiments, the adhesive patch 80 comprising circuitry used to shape and deliver stimulus pulses, may include one or more indicators 82 (e.g., visual indicators), as described in greater detail herein. In some embodiments, the function of the adhesive patch 80 and included circuitry is to test the connectivity and placement of the monopolar electrode.

In some embodiments, as illustrated in FIG. 15A, the adhesive patch 80 includes a push-button 184 used to initiate or deliver one or more stimulus pulses to the electrode 180. In some arrangements, such a push-button 184 can also be configured to change the stimulus amplitude and/or other stimulus parameters (e.g., frequency, pulse width and/or the like), as desired or required for a particular application or use.

In some embodiments, the adhesive patch 80 may include a multi-segment display (e.g., a 7-segment display). The 7-segment or other multi-segment display can comprise more than one digit and decimal place, as desired or required. The display can include a liquid crystal display (LCD), a plasma display, an organic light-emitting diode display (OLED), a thin-film transistor display (TFT) and/or any other type of display, as desired or required for a particular application or use. The display may provide information such as stimulus parameters, therapy time remaining, battery power levels, mode of operation, connectivity with other devices, etc.

In some arrangements, the adhesive patch 80 comprises a connector 186 used to interface with a second stimulation system. Such a connector can function similarly to the previously described nerve port embodiments. In some arrangements, the connector 186 comprises a molded component 188 that interfaces with the adhesive patch 80 (e.g., seamlessly or nearly seamlessly). In some embodiments, the second stimulation system includes a battery with greater capacity or any other type of system, device, component and/or the like, as desired or needed for a particular application or use. The second stimulation system can include elements similar to stimulation systems described with reference to other embodiments herein. In some embodiments, the second stimulation system may be incorporated into the adhesive patch.

Figure 15C:
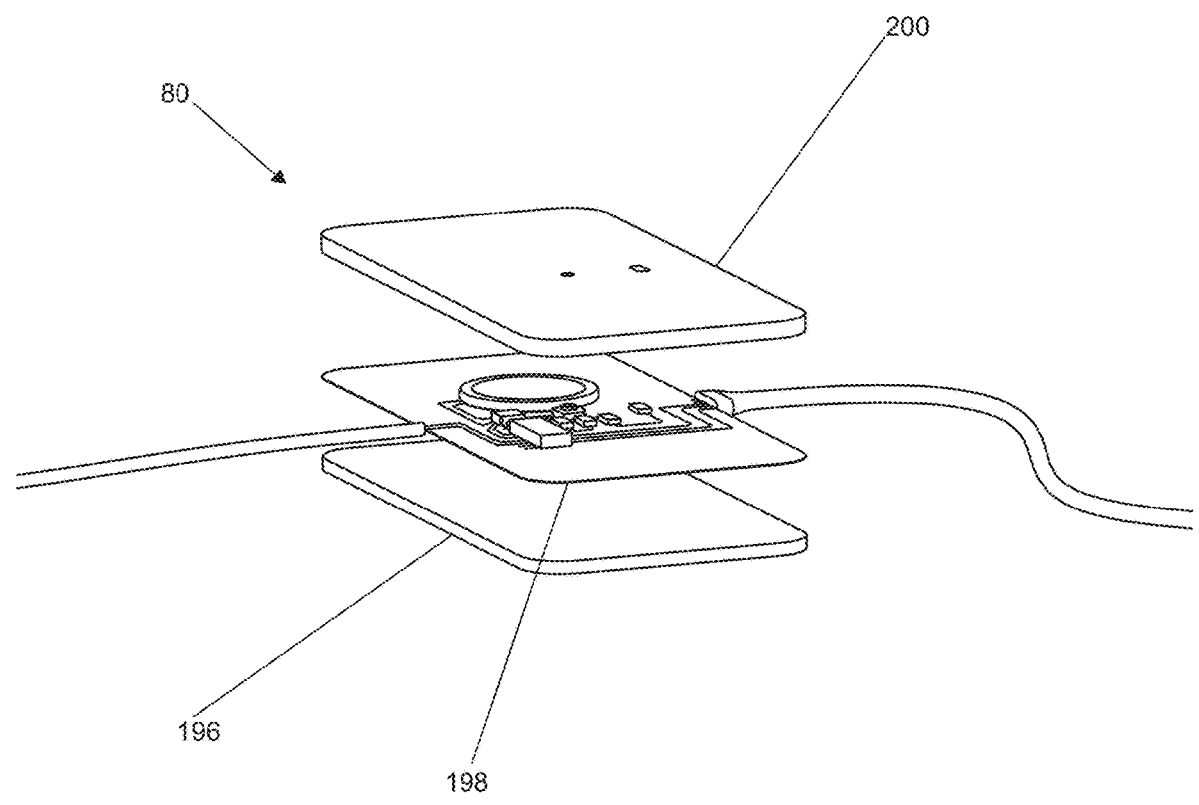
FIG. 15C illustrates an exploded view of the assembly of the adhesive patch stimulation system incorporating a con-ductive rubber skin interface, a circuitry layer and a elasto-meric protective layer according to one embodiment.

According to some embodiments, the circuitry present on the adhesive patch may include elements such as switches 194 or other components or features to direct the stimulus output from the first or second stimulation system. In some embodiments, the adhesive patch comprises of multiple layers (see, e.g., FIG. 15C). Some of the layers in such a confirmation can include a gelled conductive rubber layer 196, a layer incorporating electrical circuitry and other electrical elements 198, an elastomeric protective layer 200 and/or any other layers or components.

Figure 16A:
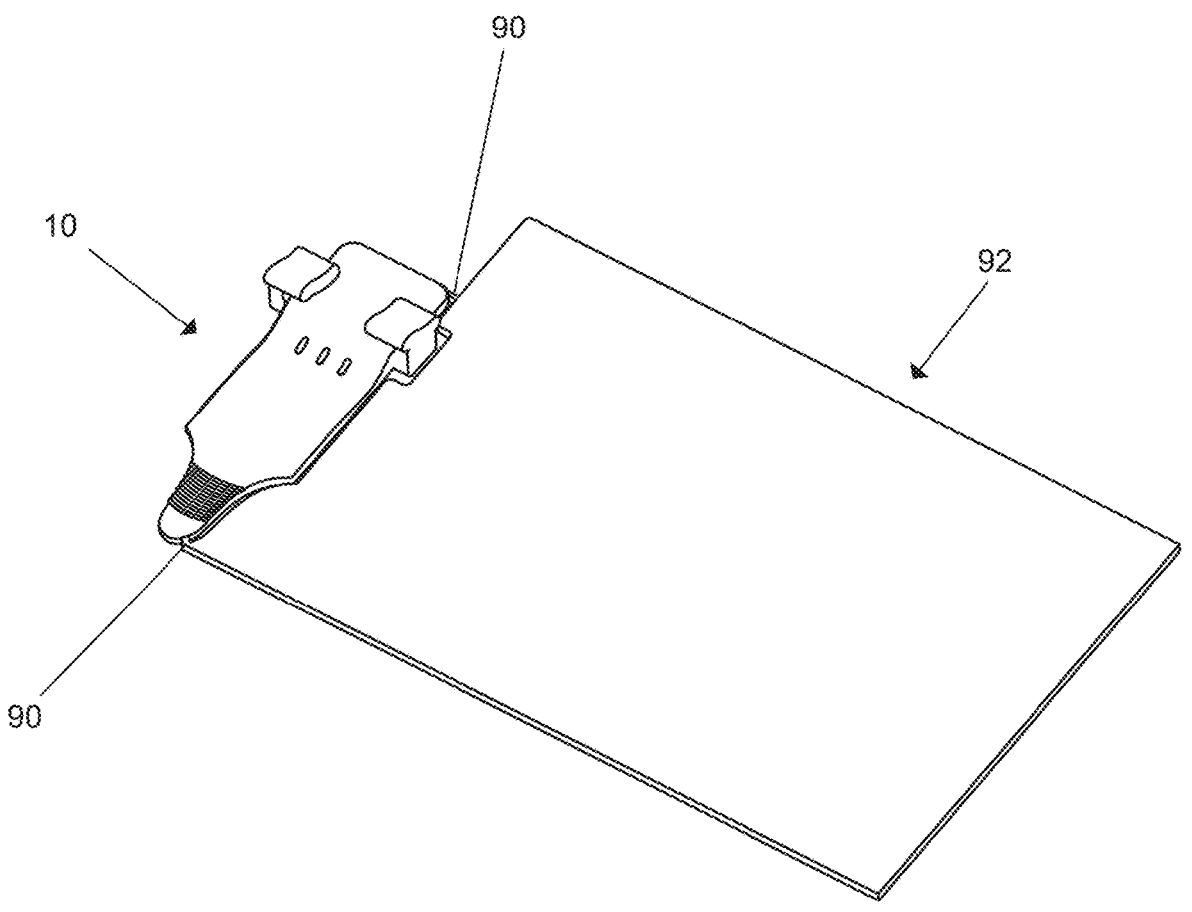
FIG. 16A illustrates a perspective view of an embodiment of the apparatus showing the carrier coupled to a polymer background material used for isolating a tissue of interest from surrounding tissue according to one embodiment.

In some embodiments, as depicted in FIG. 16A, the electrode carrier body 12 is coupled (e.g., directly or indirectly) via one or more small tabs 90 to a polymer or microsurgical background material 92. Such a material 92 can typically be used to separate or isolate a nerve or other tissue from surrounding tissue, allowing a surgeon or other practitioner to focus (e.g., solely or more exclusively) on repair or dissection of the isolated tissue.

Figure 16B:
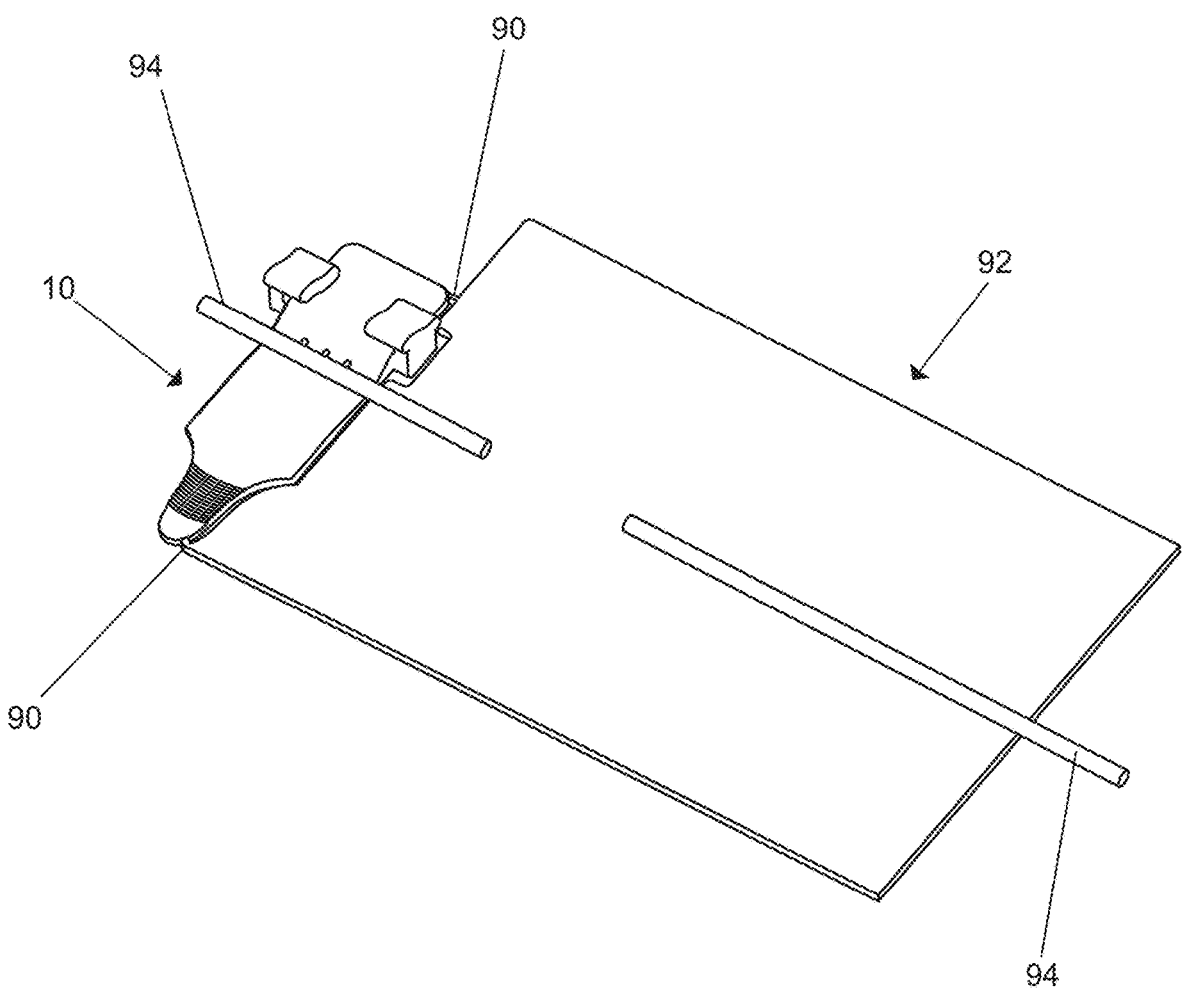
FIG. 16B illustrates a perspective view of an embodiment of the apparatus showing the carrier coupled to a polymer background material used for isolating a tissue of interest from surrounding tissue with a transected nerve situated on the background material according to one embodiment.

According to some embodiments, as illustrated in FIG. 16B, the carrier 12 and coupled background material are used to isolate an injured nerve 94 (e.g. a transected nerve) with the proximal end of the injured nerve placed on the electrode apparatus 10. The distal end of the injured nerve 94 can be placed on the background material. If, by way of example depicted in FIG. 16B, a transected nerve does not require a nerve graft to bridge the distance between proximal and distal ends, the coaptation of both nerve ends can be accomplished directly on top of the background material. If a nerve graft is to be used to bridge the gap between proximal and distal ends of a transected nerve, the insertion of the nerve graft can be accomplished on the background material.

Figure 16C:
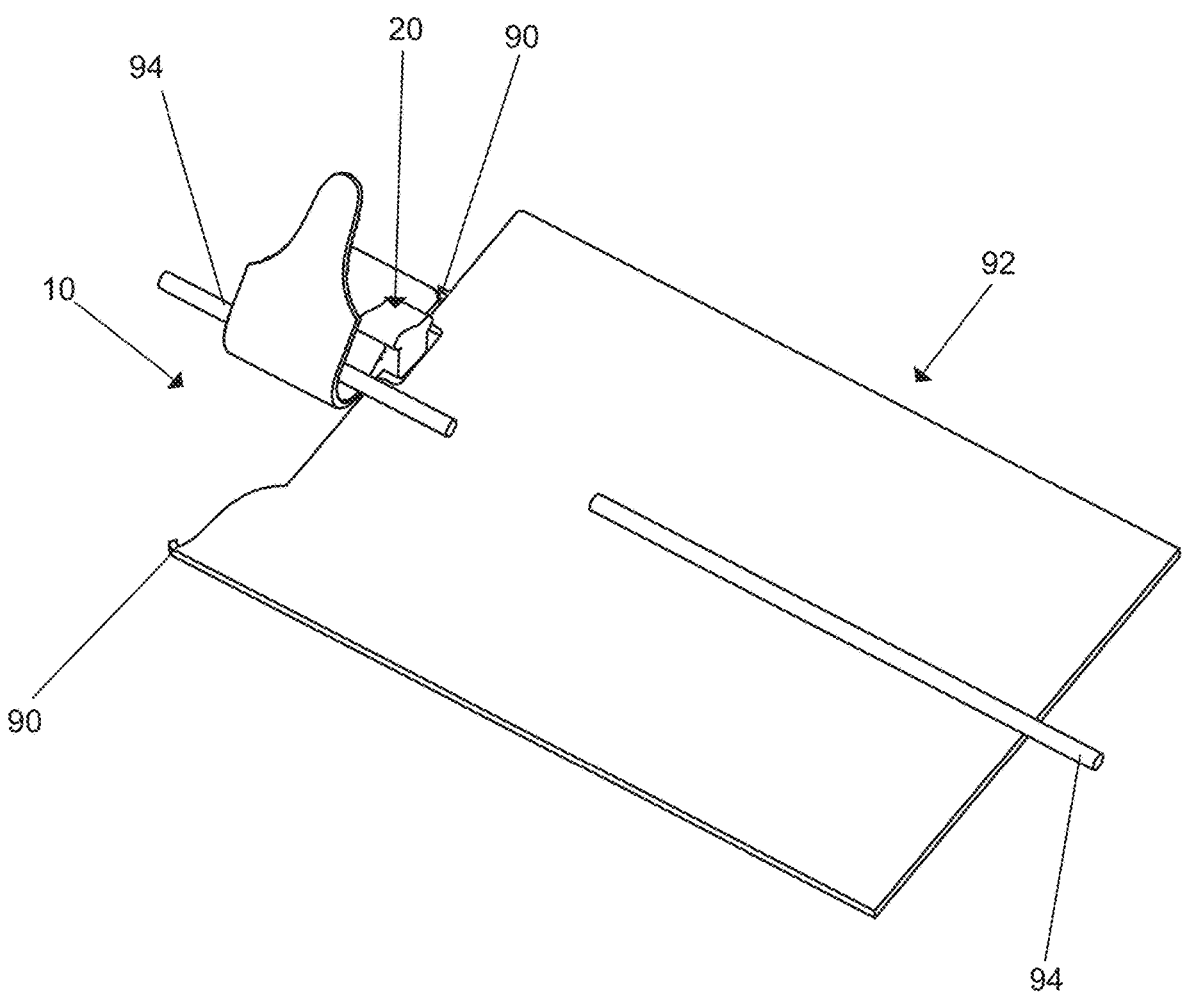
FIG. 16C illustrates a perspective view of an embodiment of the apparatus showing the carrier being folded to wrap the nerve while still partially coupled to a polymer background material used for isolating a tissue of interest from surrounding tissue with a transected nerve situated on the background material according to one embodiment.

In one embodiment, prior to repair of the injured nerve 94 (e.g., immediately prior to such repair), the electrode apparatus 10 can be disconnected from the background material by cutting (or otherwise compromising) the tabs 90. In some embodiments, the disconnected carrier body 12 can then wrap or surround the injured nerve 94, as shown in FIG. 16C, with wrapping of the proximal nerve stump prior to engaging the winged locking mechanism 20, and neuroregenerative therapy (e.g., relatively brief electrical stimulation) may be delivered to accelerate and facilitate nerve regeneration. During this time, a surgeon can perform a nerve repair or graft installment distally (e.g., immediately distally) to the electrode apparatus with the distal aspect of the proximal portion of the nerve and the distal transected nerve 94 being positioned on the background material 92.

For any of the embodiments disclosed herein, or equivalents thereof, a lead wire 32 connected to the conductive electrode pads 30 can be coupled (e.g., connected) to a stimulus output sub-system. This can help provide stimulation pulses to depolarize axons or electrically stimulate tissue. In other embodiments, the lead wire may be connected to a biological amplifier to record signals from a nerve or other tissue and/or to any other system, subsystem, device and/or the like, as desired or needed for a particular application, indication or use.

Figure 17A:
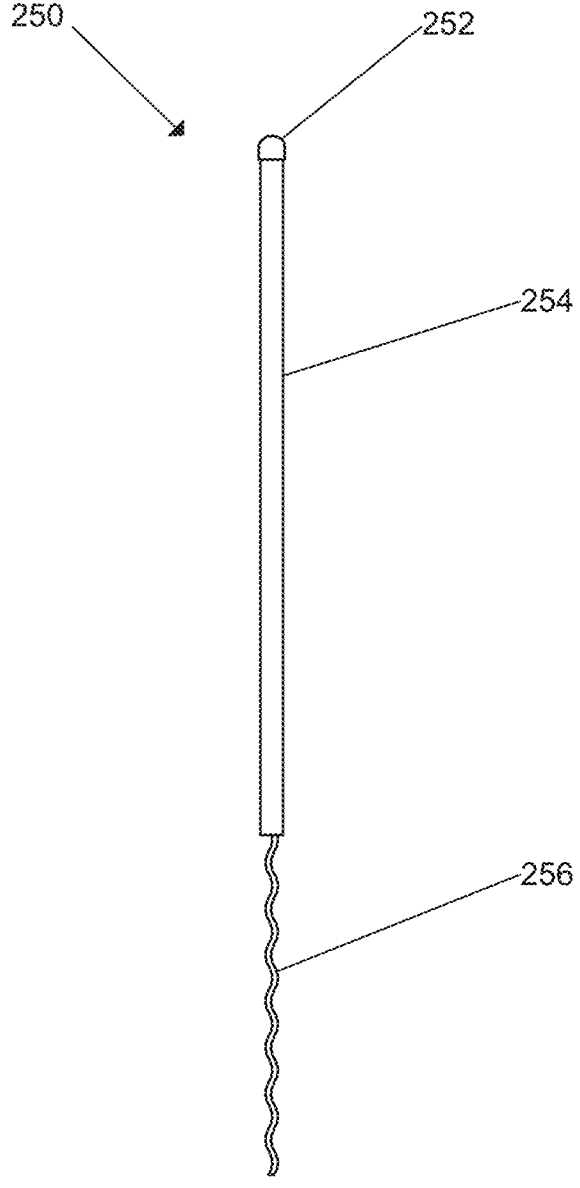
FIG. 17A illustrates one embodiment of an electrical lead.

According to some embodiments, a percutaneous electrode lead 250 may be coupled to the adhesive patch 80. The electrode lead, as illustrated in FIG. 17A, may comprise of one or more conductive elements 252. The conductive elements can be placed on or near the tip of the lead, as illustrated in one example in FIG. 17A. In other arrangements, the conductive elements 252 can be positioned along the length of the lead, either in lieu of or in addition to being at or near the tip of the lead, as desired or required.

In some embodiments, the electrode lead comprises a circular or curved shape (e.g., at least a partial circular or curved shape) and comprises an outer diameter (or other cross-sectional dimension) of 0.1 to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 1-4, 0.5-4, 1-4 mm, ranges between the foregoing, etc.). In some arrangements, the diameter or other cross-sectional dimension is determined (at least in part, e.g., largely) by the lead housing 254 (e.g., the size, shape and/or other characteristics of the lead housing). In other embodiments, the electrode comprises a needle.

Figure 17B:
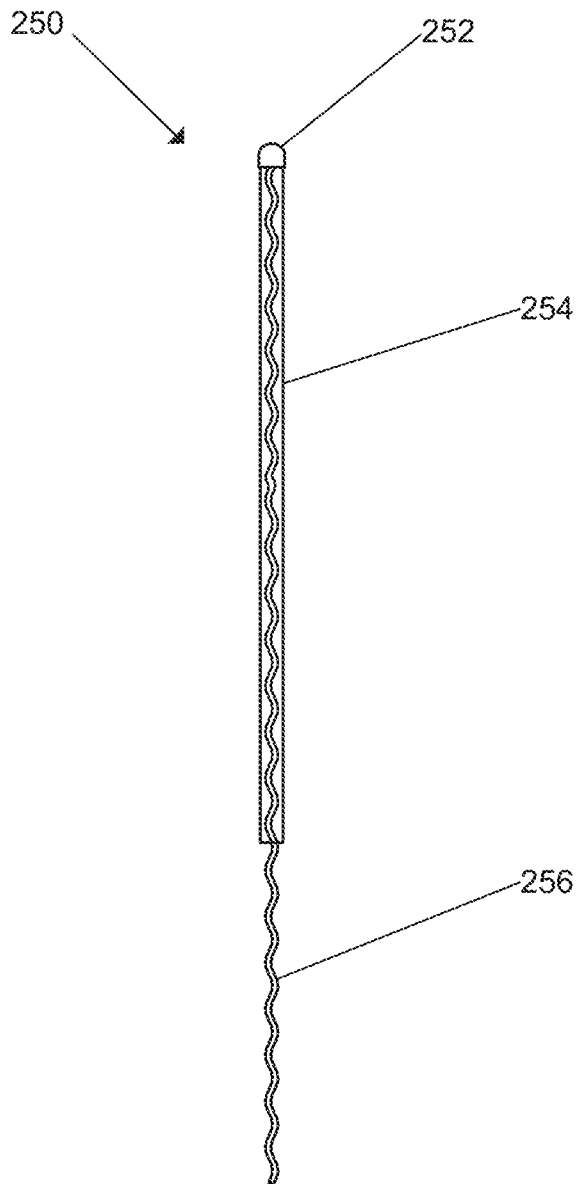
FIG. 17B illustrates one embodiment of an electrical lead.

The lead housing 254 can comprise one or more elastic or semi-elastic materials, such as, for example, silicone rubber (e.g., silicone rubber tube), polyurethane, other polymeric materials, other types of elastomeric or rubber materials, other flexible or semi-flexible materials, etc. The lead can be placed near a nerve through an existing incision or through a percutaneous approach (e.g., where a needle or other sharp object with a cannula are utilized to provide access to the nerve). The flexibility of its materials/construction and/or similar physical characteristics of the lead housing 254 can be selected to facilitate for easy removal of the percutaneous electrode lead 250. In some embodiments, the lead housing 254 comprises a lead wire 256 that is physically connected to a conductive element 252, as illustrated, e.g., in FIG. 17B.

In some embodiments, the lead housing can comprise of a uniform or continuous material thickness throughout the length of the lead. In other embodiments, the lead housing includes areas of different thickness that serve as bendable joints that can provide added flexibility for shaping the lead. In some arrangements, desired shapes are retained until other forces are applied that reshape the lead, for example manual manipulation or the act of lead removal. In other embodiments, these joint segments may comprise of materials different from the rest of the housing. In some embodiments, the joint segments may be more or less flexible than the remainder of the lead housing.

In some embodiments, the lead housing may include a coiled wire that is used to provide shape memory for the lead. This can be particularly advantageous in areas where the lead is required to bend and maintain its shape. In some arrangements, the coiled wire spans the length of the lead. In other arrangements, the coiled wire may only span a first length or portion (e.g., the first 10 cm or less, such as, for example, 0-10, 2-8, 1-5, 5-10 cm, lengths between the foregoing ranges, etc.) of the lead. However, the extent of the coiled wire need not be limited to these distances (e.g., can be greater than 10 cm, as desired or required). In some embodiments, the coiled wire is physically coupled (e.g., directly or indirectly) to an electrode. In other embodiments, the coiled wire is not electrically coupled to any stimulating electrodes. In some embodiments, the coiled wire serves as an electrical connector to other circuitry located at, along or near the distal end of the lead housing. Depending on the application, required flexibility and memory properties and/or other design considerations, the spacing between adjacent coils is zero (e.g., the coils are touching one another) or is a fixed distance. In some embodiments, the coiled wire is insulated or uninsulated. In some arrangements, the coiled wire is encased in flexible material such as various durometers of Pellethane® or Pebax® or similar thermoplastic polyurethanes or elastomers materials.

In some embodiments, the percutaneous electrode lead 250 can be connected to an extension wire that is then connected to the stimulation unit to provide more length in cases where the stimulation unit is placed further from the area where the electrode lead 250 is placed. The extension wire can comprise an additional length of 30 to 100 cm (30-40, 40-50, 50-60, 60-70, 70-80, 80-90, 90-100, 50-80 cm, distances between the foregoing ranges, etc.). The extension wire may be of similar or different material properties with at least one end that interfaces the electrode lead and makes electrical contact and at least one end that interfaces the stimulation unit and makes electrical contact. In some embodiments, when the stimulation unit, the extension wire and electrode lead are connected, they function as an integrated unit and perform similarly as described.

In some embodiments, the electrode lead housing 254 includes fiducial and/or other markers to help indicate distance from the tip of the lead. Other markers (e.g., fiducial markers) can include radiopaque markers or high echogenicity markers for image guided placement of the lead. Image guided placement of the electrode lead 250 may be advantageous in situations where direct visualization of the injured nerve and/or the electrode lead is not possible. Such situations, for example, may arise when a patient is undergoing a nerve repair or decompressive procedure under local anesthesia. Depolarization of axons is not possible within the region that is anaesthetized. In some embodiments, in order to provide neuroregenerative therapy to the injured nerve, it is advantageous to place the electrode lead 250 proximal to the region of anesthesia. In some embodiments, for the therapy to be effective (or more effective), the electrical field that is produced by the lead must depolarize the non-anesthetized proximal branches of the injured nerve. In one non-limiting example, a patient may undergo carpal tunnel release under local anesthesia, a procedure that anesthetizes the wrist. In some embodiments, proximal branches of the medial nerve, such as in the forearm, are not superficial, and image-guided placement of the electrode lead 250 would be advantageous to a surgeon in order to precisely target the proximal component of the injured median nerve. In some arrangements, image-guided placement also assures that blind insertion of the lead does not result in damage to surrounding vascular structures.

In another example, insertion of the electrode lead using image guidance may also be advantageous in situations where a nerve repair or other surgery may have been performed previously but the patient did not receive electrical stimulation therapy at time of the original repair procedure. In such situations, placement of the electrode lead using image guidance can take place hours, days, or weeks following a repair procedure. Placement of the electrode may also occur prior to a nerve repair procedure. Such placement may elicit an electrical stimulation conditioning effect of the cell body. Image guidance may be performed using ultrasound, fluoroscopy, x-ray, or other imaging modalities.

In some embodiments, the markers comprise one or more protrusions and/or recesses (e.g., dimples or reverse dimples). In such configurations, the protrusions, recesses and/or similar features can serve a dual or multi-faceted purpose or function. For example, not only could such features function as a fiducial marker, but they can also help restrict (or limit) movement of the lead when placed inside an object (e.g., cannula, sheath, another cylindrical object, another object with one or more openings, etc.).

Figure 17C:
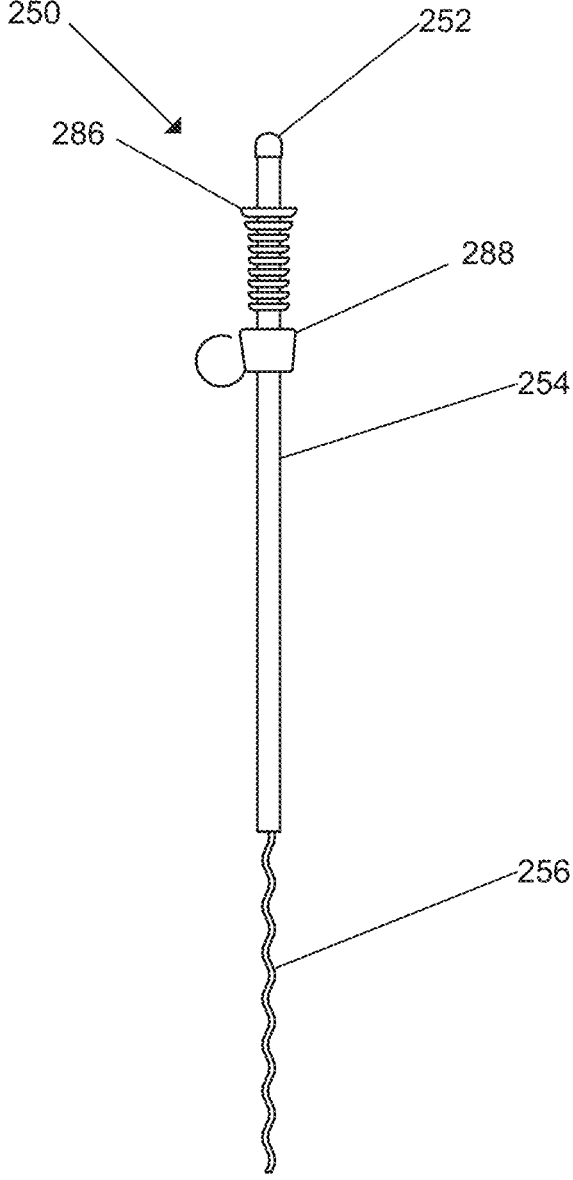
FIG. 17C illustrates one embodiment of an electrical lead.

In some embodiments, as illustrated, by way of example, in FIG. 17C, the lead housing 254 comprises a textured, ribbed and/or other non-smooth surface 286. Such a configuration can help increase the contact surface area and improve localized anchoring of lead in situ with neighboring tissue. For instance, circular or linear substructures can be included that protrude from the surface (e.g., in a winged-like manner). In addition, or in lieu of such embodiments, recessed features may be included. For example, such recessed features can be depressed within the surface of the material. In some embodiments, substructures may be shaped or differently sized as to limit or enhance prevention of movement in certain directions, while facilitating movement in others as to provide improved temporary immobilization of lead in situ. In yet another embodiment, substructures may include a single or multiple rings, hook-shaped structures and/or any other anchoring features or members 288 to improve or otherwise enhance anchoring of the electrode lead with suturing, or similar, to neighboring tissue. Such designs can be advantageous to users in order to affix stimulating leads in close proximity to targeted nerve tissue, ensure minimal or reduced unintended movement, facilitate removal of the lead with minimal disturbance to tissues once stimulation is complete and/or provide one or more other advantages or benefits. By way of an example, a user can place the lead parallel or approximately parallel or tangential to a targeted nerve structure, and if desired, use standard medical sutures and/or other fixation technologies to engage flexible structures on the lead to anchor to tissue.

Figure 17D:
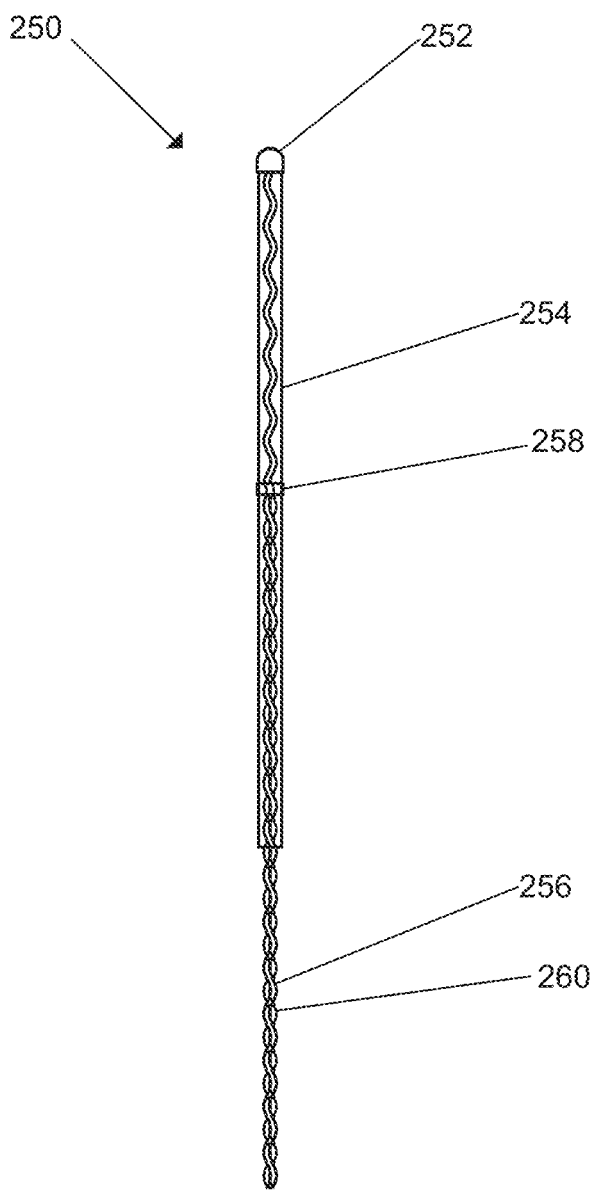
FIG. 17D illustrates one embodiment of an electrical lead.

In some embodiments, as illustrated in FIG. 17D, the percutaneous electrode lead 250 comprises multiple conductive elements, 252, 258. The conductive elements 252, 258 can include different shapes, sizes and/or other characteristics, as desired or required. For example, as illustrated in FIG. 17D, the conductive element at the tip 252 of the electrode lead can be shaped in a manner to cap the electrode lead housing 254 and also provide a larger surface area that may be used to provide stimulus current to tissue such as peripheral nerves. With continued reference to FIG. 17D, a second conductive element 258 can be shaped as a ring with said ring varying in thickness from 0.1-10 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 2-8, 3-6, 1-3, 3-5, 5-8 mm, ranges between the foregoing, etc.) and can be physically coupled to a conductive insulated wire 260. In some arrangements, a second conductive element 258 can be used as a return electrode for the first conductive element essentially creating a bipolar stimulating field. In other arrangements, the second conductive element is used as a signal path for other circuitry and is combined with additional conductive elements placed on the lead. The plurality of conductive elements can also form an electrical stimulation array allowing to shape or otherwise modify or impact the current field.

Figure 18A:
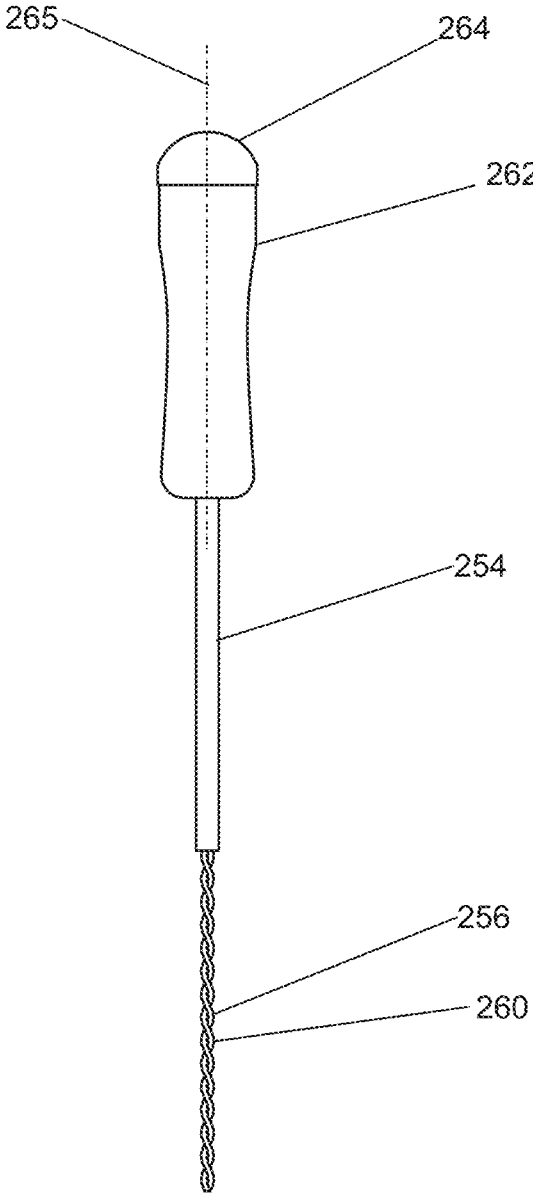
FIG. 18A illustrates one embodiment of an electrical lead coupled to a cap element.

In some embodiments, as illustrated in FIG. 18A, the percutaneous electrode lead 250 is coupled to a cap element that comprises an enclosure 262 (e.g., a shaped, plastic or other elastomeric or electrically non-conductive enclosure or member) and a conductive surface 264. In some arrangements, the conductive surface 264 is larger than the enclosure 262. The plastic enclosure 262 can be greater than one but less than twenty times the diameter of the electrode lead (e.g., 1 to 20 times, such as, 1-5, 2-4, 5-10, 10-20, 5-15, values between the foregoing, etc.), as desired or required. In some arrangements, the percutaneous electrode lead 250 that comprises a conductive element at the tip 252 (as previously described herein), may be in physical contact (e.g., at least partial physical contact) with the larger conductive surface 264 present on the cap, effectively creating a larger stimulating surface. As an example, if the electrode lead is coupled to a pulse generator, covered with the described cap, and said pulse generator outputs a long duration pulse (e.g., a pulse having a wavelength greater than 200 μs), the larger conductive surface of the cap may be used to stimulate muscle tissue. In the context of verifying stimulus output, this may be advantageous since a smaller conductive surface (e.g., as included on an electrode lead) may not create a sufficiently large electric field to elicit a visual muscle contraction. The use of the larger conductive surface on the cap to stimulate muscle can arise, for instance, in situations where an intact uninjured motor nerve is not readily accessible for stimulation. Using the cap to create a visual contraction in the muscle can provide enhanced confirmation to the user that stimulus is being output to the electrode.

In some arrangements, the cap may be shaped similarly to a pen-like structure to facilitate holding, grasping, manipulation, use and/or the like. In such an arrangement, the cap may function as a nerve locator. In some embodiments the cap may include a monopolar probe or a bipolar probe. These probes can be configured to provide a smaller conductive surface for fine resolution of the stimulating field in order to map anatomical location of nerves. These arrangements can advantageously allow for a multi-function system providing both nerve location functionality and neuroregenerative functionality.

In some embodiments, the cap comprises two or more pieces or portions that snap-fit together around the electrode lead. In other embodiments, any other type of connection or attachment method or technology can be used, such as friction or press fit, couplings (e.g., standard or non-standard), mechanical fasteners or other mechanical connections, etc.

Figure 18B:
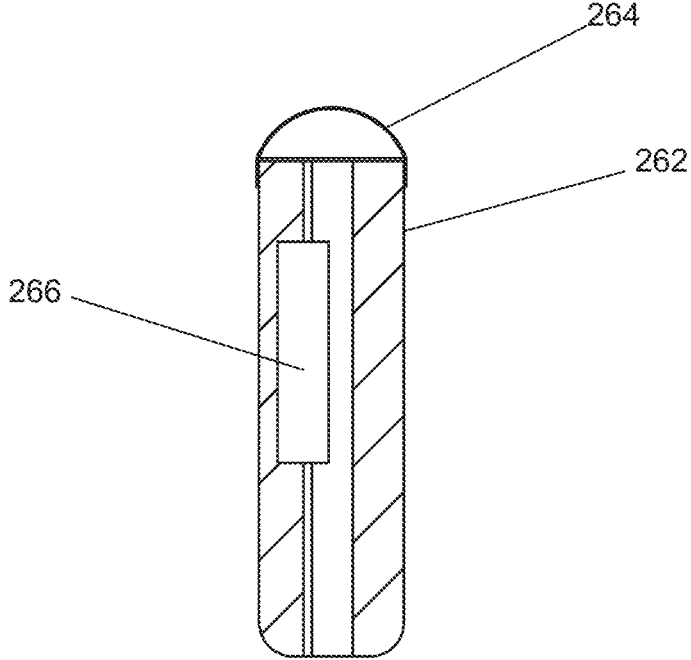
FIG. 18B illustrates one embodiment of a cap element comprising electrical circuitry.
Figure 18C:
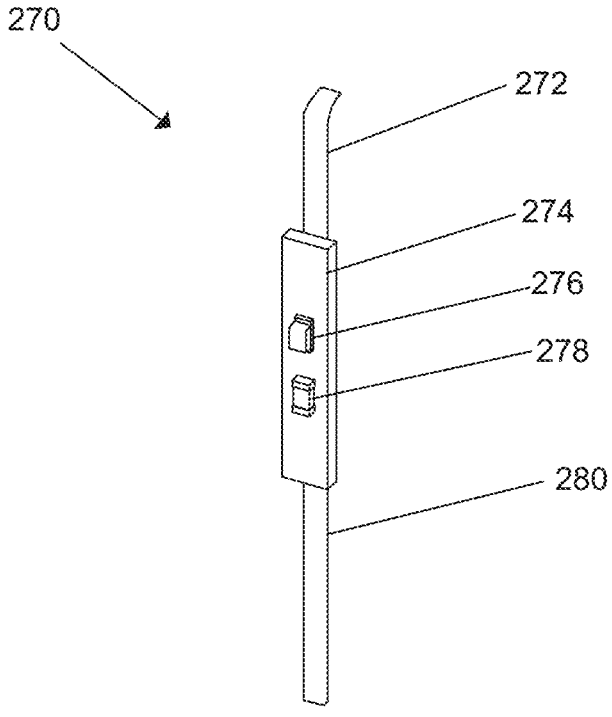
FIG. 18C illustrates one embodiment of an assembly configured to be secured to a cap element.

In some embodiments, the enclosure 262 (e.g., shaped enclosure) includes space for embedded circuitry. In some arrangements, the enclosure comprises a shaped plastic enclosure. FIG. 18B provides a cross-section view of the cap with reference to the plane 265 drawn in FIG. 18A and includes the potential space for circuitry 266. In some embodiments, such circuitry comprises one or more assemblies 270, such as illustrated in FIG. 18C. In one example, as shown, the assembly 270 comprises two conductive components, a distal component 272 and a proximal component 280 that interface with a printed circuit board 274. The printed circuit board can include passive and/or active components. In some embodiments, the printed circuit board 274 comprises a resistor 276 and a LED 278.

In yet other embodiments, the circuitry comprises a combination of indicators and controls, including, by way of example, one or more LEDs (and/or other indicators) and/or one or more buttons or other controls or controllers. Such a design can be advantageous to users in order to activate pulse generation, verify functional output at tip (e.g., by way of an illuminating LED) and/or in one or more other manners. By way of an example, a user can connect the electrode lead 250 to a pulse generator, activate pulse generation using the button on the electrode cap and verify function by observing LED on the electrode cap. Such a button, control or other controller can also be configured to change the stimulus amplitude and/or one or more other stimulus parameters (e.g., frequency, pulse width and/or the like), as desired or required for a particular application or use.

Figure 18D:
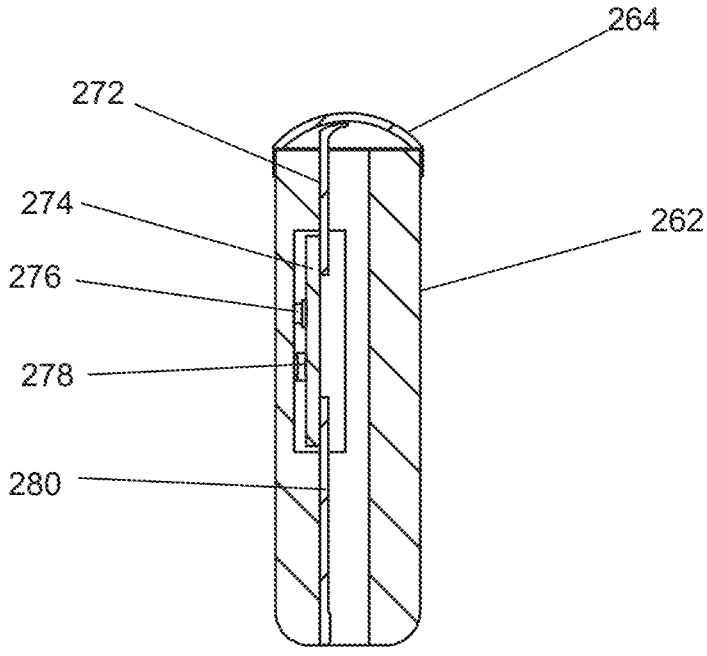
FIG. 18D illustrates the assembly of FIG. 18C secured to the cap element of FIG. 18B.
Figure 18E:
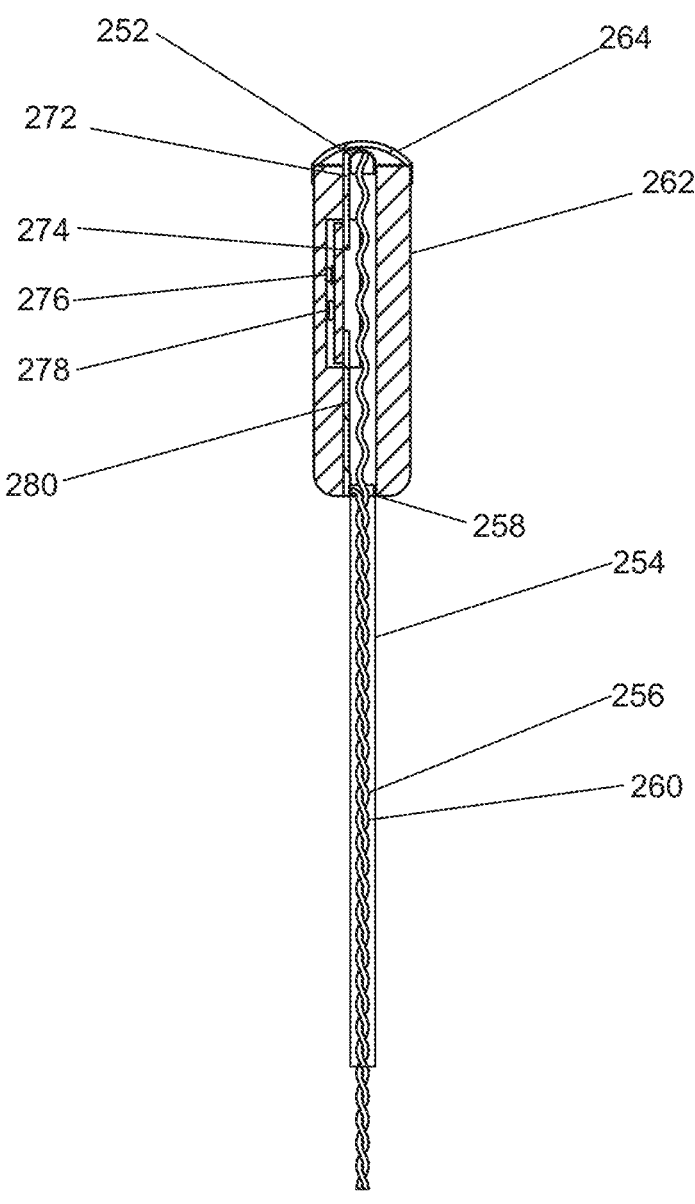
FIG. 18E illustrates one embodiment of an electrical lead comprising a cap element.

FIG. 18D illustrates the electrode cap 261 with the embedded assembly 270 of FIG. 18C. In some embodiments, the distal conductive component 272 is coupled (e.g., physically connected) to the conductive surface 264 on the cap. When the cap is fully assembled relative to the electrode lead 250, the proximal conductive component 280 of the cap can be in physical contact with a conductive element 258 on the electrode lead, as depicted, for example, in FIG. 18E.

In some arrangements, when the cap is appropriately shaped and otherwise configured, connection of the conductive tip 252 of the lead to the distal conductive component 272, along with connection of the secondary conductive element on the lead 258 to the proximal conductive component 280, can allow for current to flow from the lead tip, through the circuitry in the printer circuit board 274 and out to the secondary conductive element 258 on the lead. Such a design can be advantageous to permit users to test if the conductive tip is functional.

By way of an example, a user can connect the electrode lead 250 to a pulse generator. When a pulse is elicited from the generator, provided the conductive tip 252 is not damaged and the cap is interfaced appropriately with both the conductive tip 252 and the secondary conductive element on the lead 258, current may flow through the circuit board and activate the LED or other indicator. Thus, visual confirmation can be provided to the user that current is flowing through the conductive tip 252. In some embodiments, confirmation of current flow to conductive tip may be provided in one or more forms, including, without limitation, visually, audibly, haptically and/or in any other manner, including combinations of the foregoing. Such a configuration can be incorporated into any of the implementations disclosed herein or variations thereof.

Figure 19:
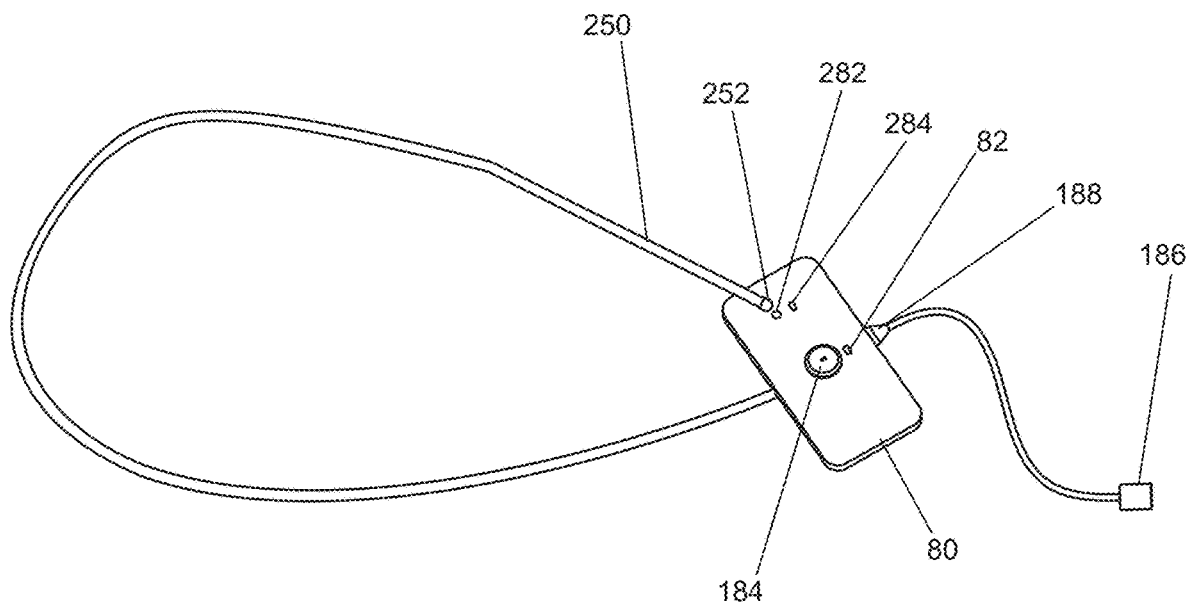
FIG. 19 illustrates one embodiment of an adhesive patch that includes an exposed conductive contact.

According to some embodiments, the adhesive patch 80 includes an exposed (e.g., at least partially) conductive contact 282 as shown in FIG. 19. Additionally, the adhesive patch 80 can include one or more LEDs (and/or other visual indicators) 284 that can be coupled (e.g., directly or indirectly) to the conductive contact through one or more resistive or other elements. By way of an example, as shown in FIG. 19, the adhesive patch 80 can comprise a percutaneous electrode lead 250 (e.g., in accordance with those described herein or equivalents thereof). In some arrangements, for a user to test if the conductive tip of the lead 252 is functional, practitioner or other user can place the tip 252 in physical contact (e.g., at least partial physical contact) with the exposed conductive contact 282 on the adhesive patch. In some embodiments, provided that the patch is outputting a stimulus pulse, a particular action by the user (e.g., depressing a switch 184), the LED or other visual or other indicator 284 can be activated (e.g., illuminated), thereby providing visual confirmation that the conductive tip is functional and is able to pass stimulus current. In some embodiments, confirmation that conductive element is functional may include visual, audible or haptic indication, or a combination thereof.

In some embodiments, the patch 80 comprises a microcontroller and a stimulus generator such that the stimulus generator outputs a low amplitude AC waveform that in some embodiments may be used as a verification signal. In some embodiments, by way of example, the amplitudes are 0.1 μA to 10 μA (e.g., 0.1-0.2, 0.2-0.3, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 0.1-1, 0.5-2, 1-5, 5-10 μA, values between the foregoing, etc.). In other embodiments, the amplitudes are less than 0.1 μA (e.g., 0.01-0.1, 0.005-0.001 μA, less than 0.005 μA, etc.) or greater than 10 μA (e.g., 10-15, 15-20, more than 20 μA, etc.), as desired or required. AC waveforms may include a square wave, sinusoidal wave, or other alternating current waveforms at frequencies greater than 1 Hz (e.g., 1-2, 2-3, 3-4, 4-5, 5-6, 6-7, 7-8, 8-9, 9-10 Hz, frequencies between the foregoing ranges, greater than 10 Hz, etc.) or frequencies smaller than 1 Hz (0.01-0.1, 0.1-0.2, 0.2-0.3, 0.3-0.4, 0.4-0.5, 0.5-1, 0.3-0.7 Hz, frequencies between the foregoing ranges, etc.).

In some embodiments, the stimulus generator is coupled (e.g., physically (e.g., directly or indirectly), operatively, etc.) to the electrode lead. In some embodiments, the microcontroller is programmed to prevent output of stimulus pulses (such as, for example, the pulses that have been described herein) until the verification signal has been applied to an exposed conductive contact 282, as shown, for example, in FIG. 19. Such a "verify to unlock" feature can be advantageous to users as it verifies (e.g., directly) the functionality and integrity of the electrode lead 250 and conductive tip 252.

Figure 20A:
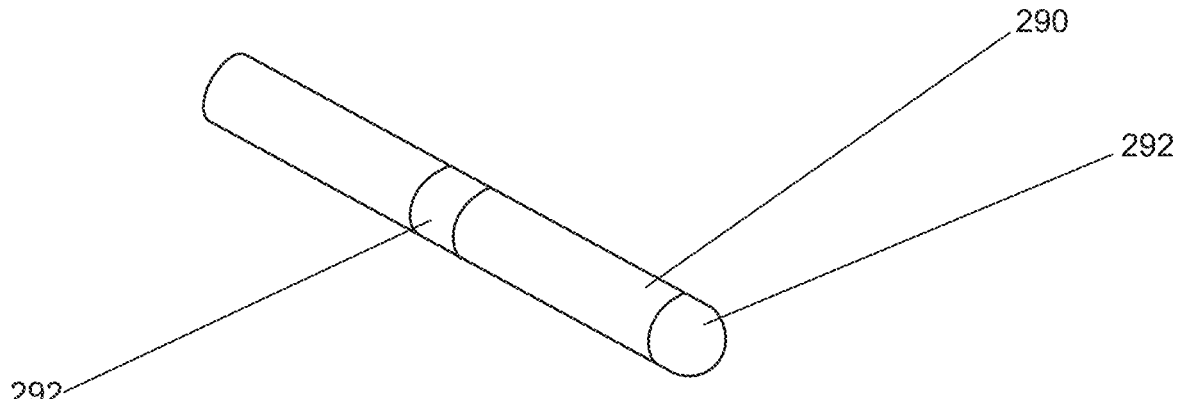
FIG. 20A illustrates one embodiment of a verification assembly that includes a conductive element.

In some embodiments, the electrode lead wire is coupled to cuff electrode apparatus 10 (e.g., such as those apparatuses described herein, variations thereof and/or any other type of cuff electrode). To verify output of the cuff electrode, a verification bar 290, such as the one illustrated in FIG. 20A, can include one or more conductive elements 292 and can be placed within a wrapped or unwrapped cuff electrode.

Figure 20B:
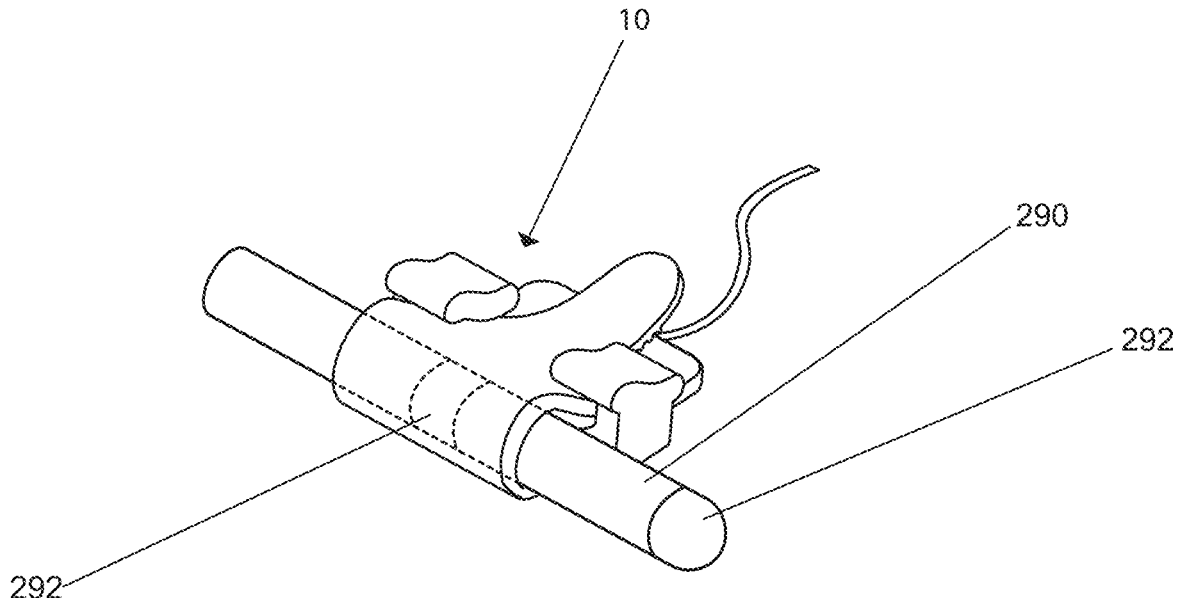
FIG. 20B illustrates one embodiment of a cuff electrode apparatus that is interfaced with the verification bar.

According to some arrangements, as illustrated in FIG. 20B, a cuff electrode apparatus 10 with a monopolar electrode configuration (e.g., such as any of the embodiments thereof described herein) is configured to interface with the verification bar 290 or similar features or portion. In some configurations, a conductive element within the verification bar is in physical contact (e.g., at least in partial physical contact) with the monopolar electrode within the cuff. Further, the conductive element can also be coupled to a conductive element that is at or near the tip of the bar and in an area that is not wrapped by the electrode. In some embodiments, a user can selectively verify stimulus output of the cuff electrode apparatus 10 by placing the exposed conductive tip on an exposed contact surface used for lead testing such as the previously described exposed contact on a patch used for lead testing 282. This process of verification is similar to those described herein when using a percutaneous lead wire with conductive tip and can be applied to any embodiments disclosed herein.

Figure 20C:
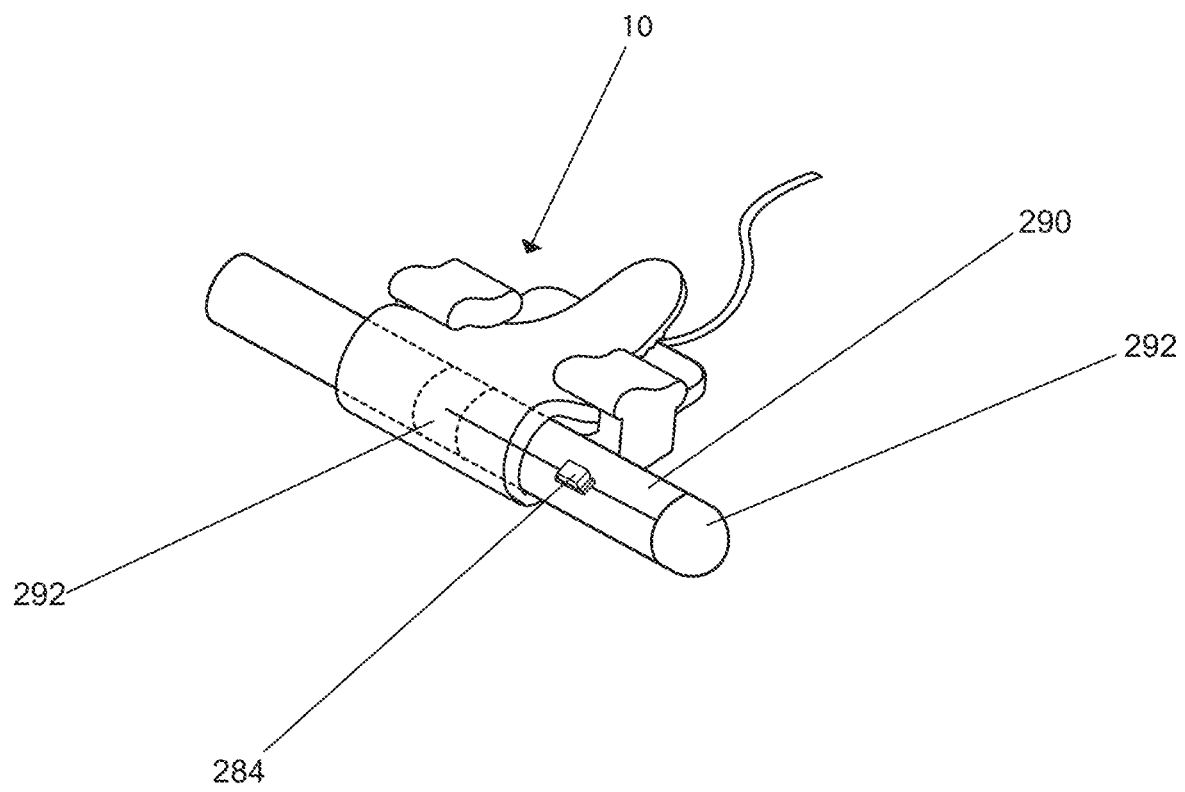
FIG. 20C illustrates one embodiment of a cuff electrode apparatus that is interfaced with the verification bar.

In certain embodiments, the verification bar 290 includes one or more LEDs and/or other visual indicators for testing verification 284. In one example, as illustrated in FIG. 20C, the verification bar 290 comprises a conductive element 292 that is in contact with an electrode of an electrode apparatus 10 (e.g., such as those described previously herein). The conductive element 292 of the verification bar 290 can be coupled to a LED or other visual indicator, which is coupled (e.g., operatively, electrically, etc.) to a second conductive element 292. A user can verify stimulus output of a cuff electrode apparatus 10 by placing the exposed conductive tip on an exposed contact surface used for lead testing (e.g., the previously described exposed contact on a patch used for lead testing 282). In some embodiments, activation of the LED or other indicator 284 within the verification bar can indicate proper current conduction from the electrode apparatus 10.

Figure 20D:
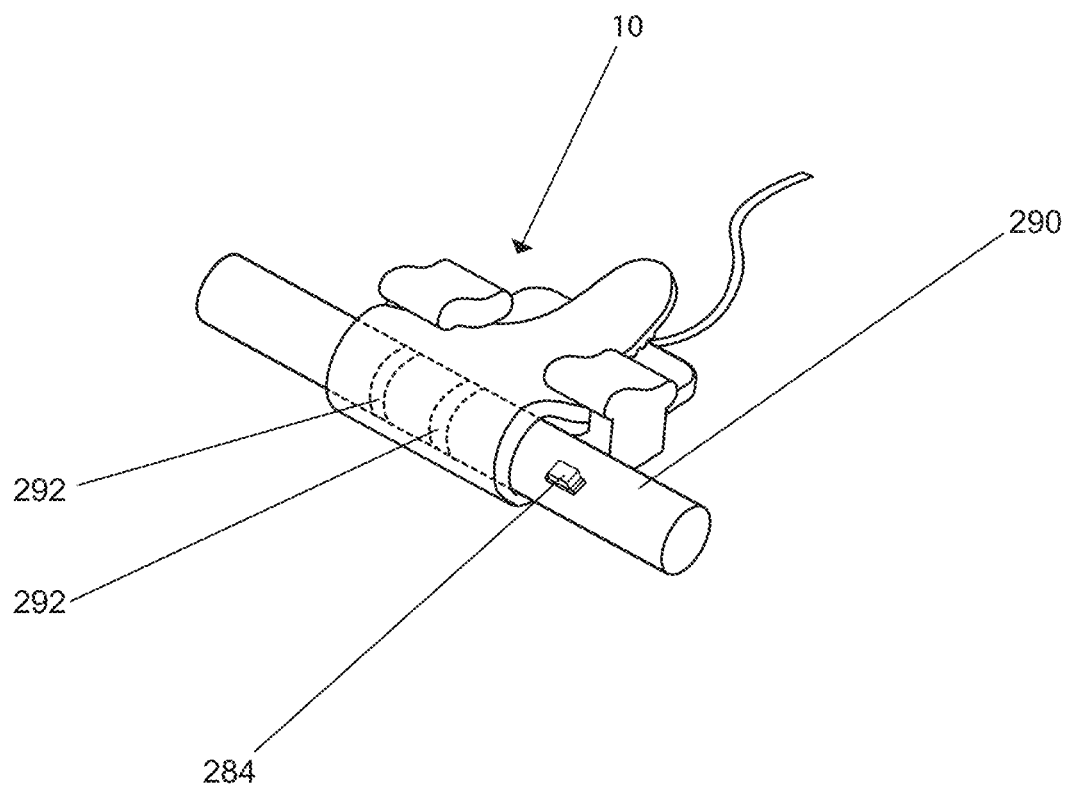
FIG. 20D illustrates one embodiment of a cuff electrode apparatus that is interfaced with the verification bar.

In some embodiments, the verification bar 290 is designed and otherwise configured to interface with a multi-contact electrode apparatus. In one example, as shown in FIG. 20D, the verification bar 290 comprises two conductive elements 292 such that each conductive element 290 of the verification bar is in physical contact (e.g., at least in partial physical contact) with a separate electrode of a cuff electrode apparatus 10. In some embodiments, the verification bar 290 that interfaces with multiple electrodes can include one or more LEDs and/or other visual or other indicators, as desired or required. With continued reference to the example depicted in FIG. 20D, verification of the stimulus output can be advantageously performed directly at the level of the electrode apparatus without use of a separate exposed contact surface for lead testing. In some embodiments, the verification bar 290 may be physically coupled to the adhesive patch 80.

Figure 21A:
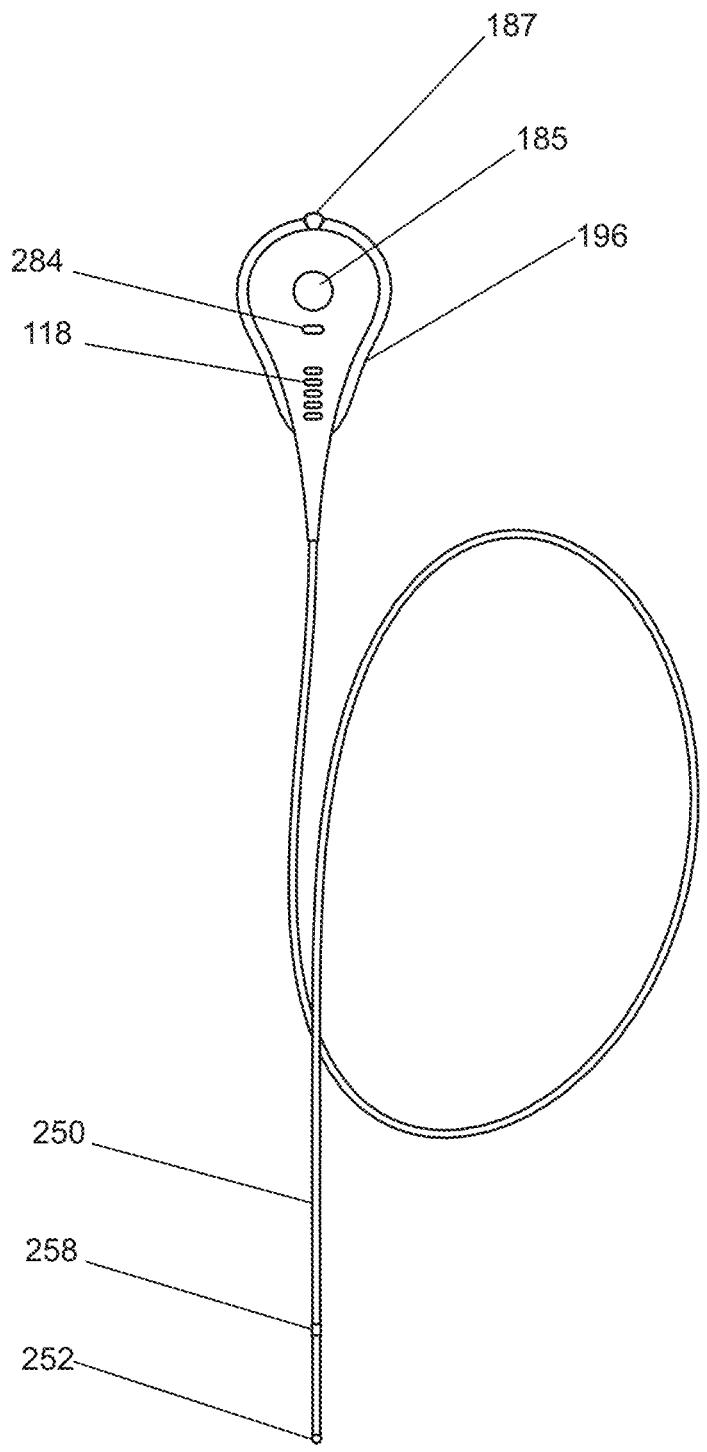
FIGS. 21A and 21B illustrate one embodiment of an electrode comprising of a percutaneous lead coupled to a housing including a stimulation source.
Figure 21B:
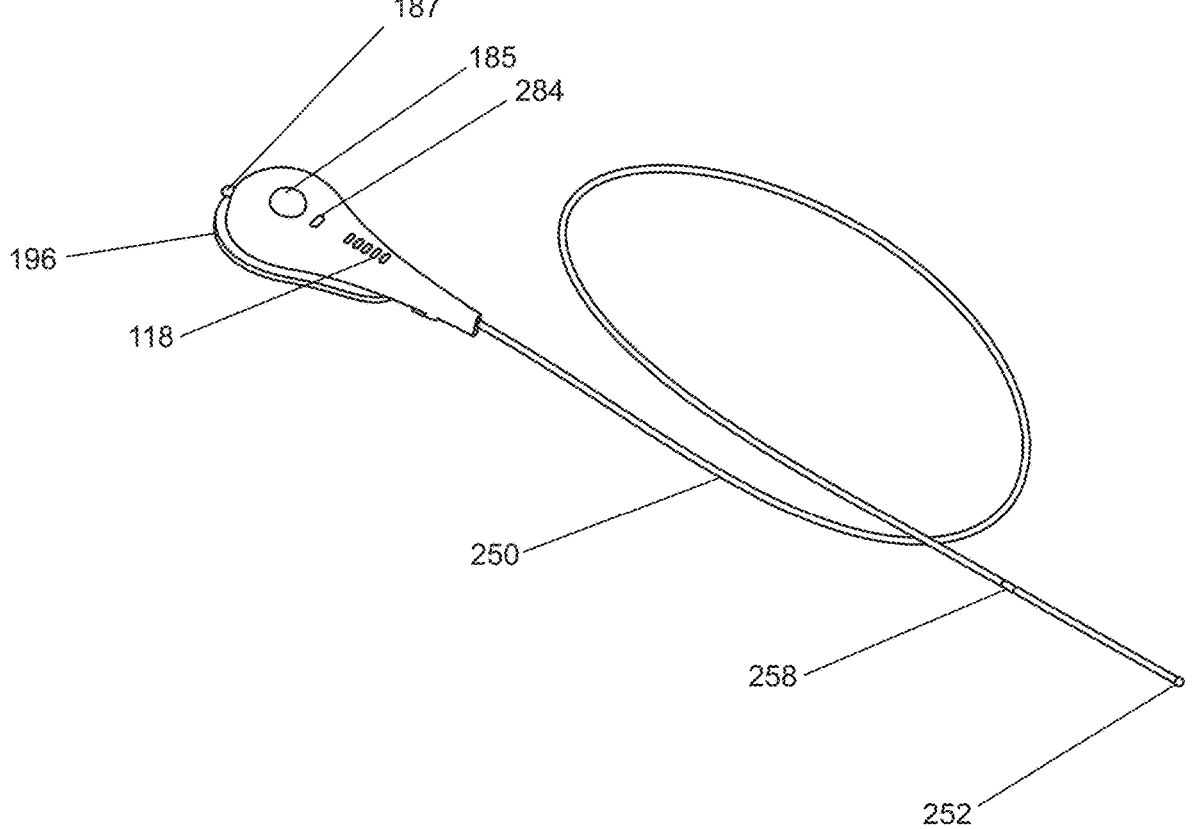

In some embodiments, the percutaneous electrode lead 250 with multiple conductive elements 258 (e.g., as described herein), is coupled (e.g., physically, electrically, operatively, etc.) to a stimulation source that can include circuitry to test the connectivity and placement of the electrode lead. In some arrangements, the stimulation source can also be configured to provide neuroregenerative therapy (e.g., via the delivery of stimulation energy). One such embodiment, which can be termed a functionalized electrode, is illustrated in FIGS. 21A and 21B. In some embodiments, such an electrode can comprise a percutaneous lead coupled to a housing that may include a stimulation source.

Figure 21C:
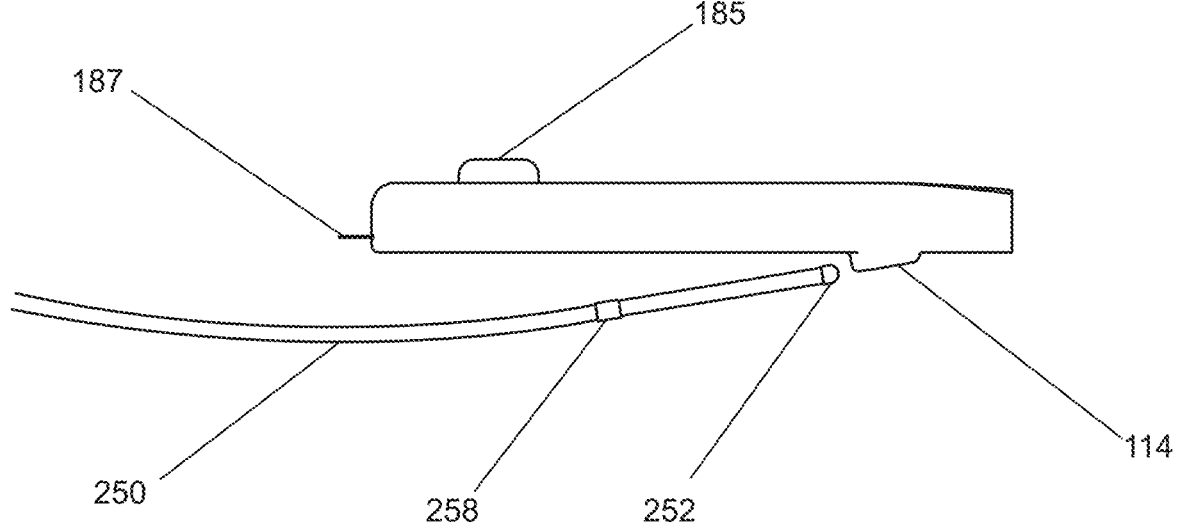
FIG. 21C illustrates one embodiment of an electrode comprising of a percutaneous lead coupled to a housing including a stimulation source.

In some embodiments, as illustrated in FIG. 21C, verification of the stimulus output can be performed by inserting one or more conductive elements of the lead into a housing 114 of an electrical stimulation apparatus that comprises of verification test elements, as described herein. In some embodiments, such a stimulation apparatus can include one or more visual elements 284 and/or can include another type of indication to the user (e.g., audible indication, haptic indication, etc.) to notify a user that the stimulus output is verified.

According to some embodiments, the housing of the electrical stimulation apparatus comprises a pull-tab 187 (e.g., as described herein with reference to other embodiments). In some arrangements, a stimulation apparatus includes one or more verification mechanisms or features to help place the system in an "unlock" mode (e.g., as also described herein). By way of example, a percutaneous electrode lead with multiple conductive elements can be packaged with one or more conductive elements inserted into the housing of a stimulation apparatus with a pull-tab or similar feature. When a user removes the pull-tab, the stimulation apparatus can notify (e.g., immediately notify, such as within less than one second) a user the status of the stimulus output using the indicator that is included in the corresponding device (e.g., visual indicator, audio indicator, haptic indicator, combination thereof, etc.). In other embodiments, notification to a user can take other forms (e.g., other types of indication, within other time frames, etc.), as desired or required. The status may be used to "unlock" or turn on stimulation circuitry or prevent the circuitry from being powered. This may be advantageous to a user in that the appropriate functionality of the pulse generator and the electrode lead integrity may be evaluated in a single step and without the need of placing the lead on or near excitable tissue and delivering stimulus pulses.

In some embodiments, the pull-tab may be replaced by a tactile switch 185 or other type of switch. In some arrangements, the stimulation apparatus includes multiple indicators (e.g., visual, audible, haptic, other indicators, etc.) that may be used to provide (e.g., display) information, including, without limitation, time, relative stimulus amplitude 118 and/or the like.

Figure 22:
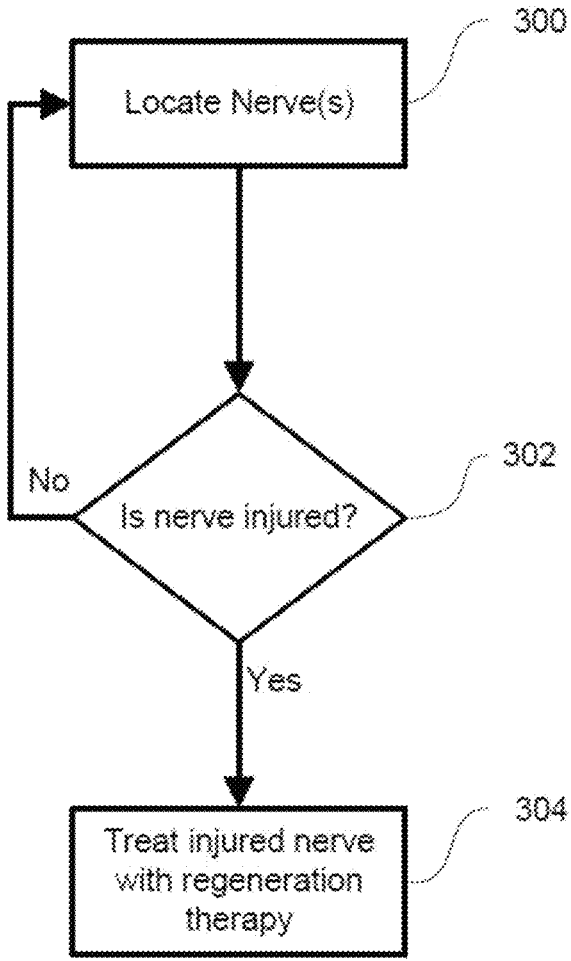
FIGS. 22 and 23 include flow diagrams illustrating two different embodiments of methods for using the systems and devices disclosed herein.
Figure 23:
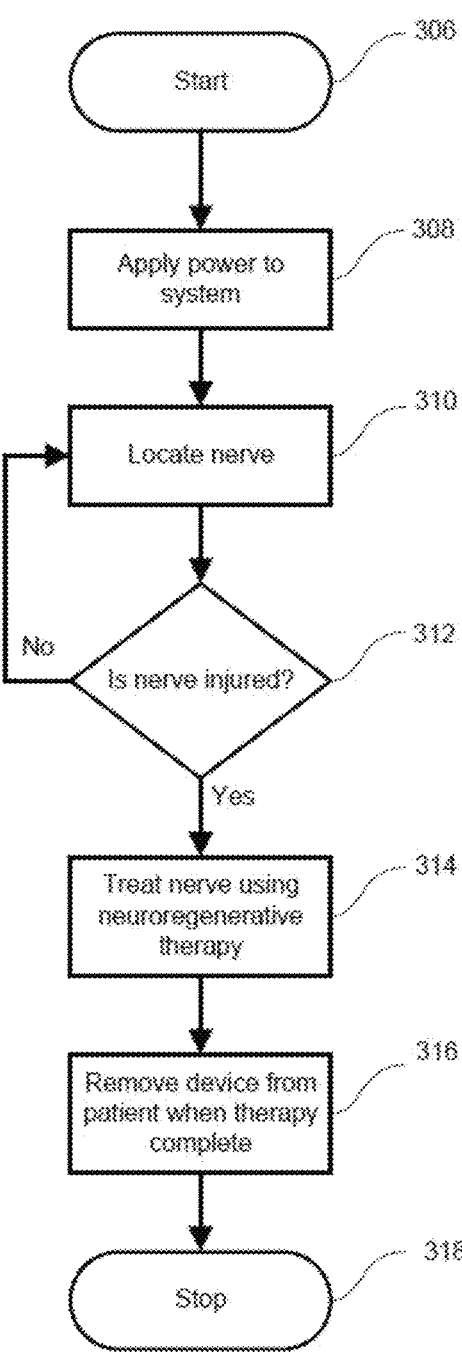

According to some arrangements, shown in FIGS. 22 and 23, the device or system is used to first locate a nerve 300, 310, and if an injured nerve is found or otherwise detected 302, 312, to provide neuroregenerative therapy to it 304, 314. In some embodiments, the device or system is used only as a nerve locator or only as a regenerative therapy system. However, in some configurations, it is advantageous for the device or system to be adapted to do both the detection and subsequent delivery of energy (e.g., for neuroregenerative therapy). Such features can be incorporated into any of the device or system embodiments disclosed herein.

In some embodiments, the device or system comprises a single control button or other control or controller (e.g., which can take the form of something other than a button) used to switch between a first phase of stimulation and a second phase of stimulation. Such a button or other control or controller can also be used to adjust stimulus output parameters and control visual indicators and/or conduct any other function, as desired or required.

Intraoperative Nerve Location and Therapy

According to some arrangements, one intended use of the system is in the operating room. Thus, the system can be designed, customized and otherwise configured with such intended use mind. The various systems disclosed herein can advantageously function and operate as a dual-purpose device serving the needs of both nerve location functionality and nerve (e.g., neuroregenerative) therapy.

In some embodiments, the housing of the system comprises a bipolar probe type electrode used for nerve location purposes with a port used to connect a cuff-type electrode that can be used to interface with an injured nerve to deliver neuroregenerative therapy to injured nerve tissue. The bipolar electrode apparatus may be similar to any of the ones described in greater detail herein. In one embodiment, the injured tissue is a peripheral nerve. However, in other arrangements, the injured tissue can include any other type of nerves, such as autonomic nerves. In other embodiments, a bipolar electrode may be one of various types that are common to those skilled in the art. In such configurations and uses, the surgeon or other practitioner can physically connect an electrode with lead wire and connector to a jack or other coupling location located on the housing unit. A flow diagram of one embodiment of usage of a dual-purpose device is schematically illustrated in FIG. 24 and described in greater detail below.

Figure 24:
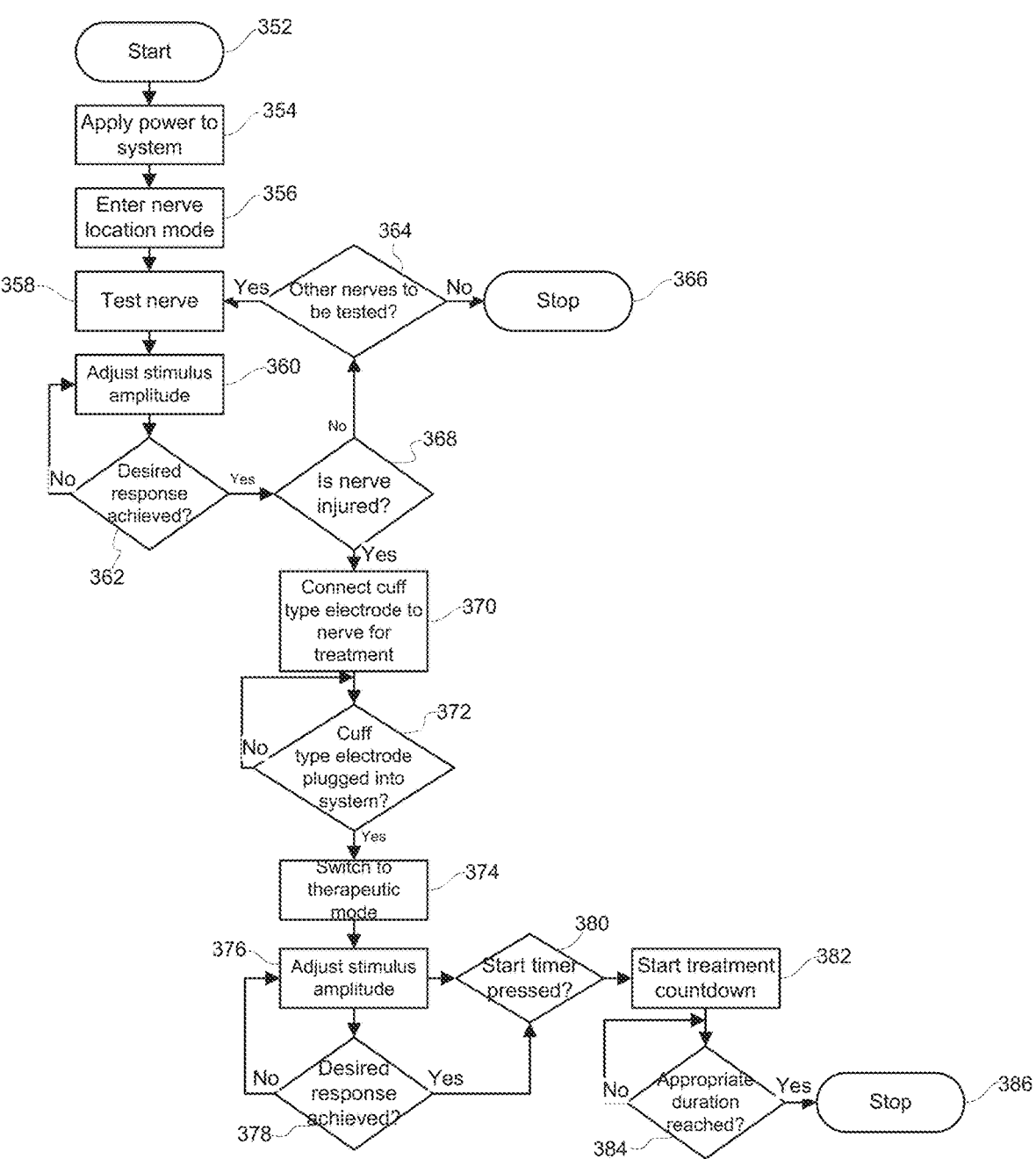
FIG. 24 is a flow diagram illustrating the process of locating and treating an injured nerve in an intraoperative setting using the described system according to one embodiment.

In one embodiment, as illustrated in the example of FIG. 24, when the system is first powered on 354, it is configured to enter a "test" mode. In one example, the test mode is adapted to assist in locating nerves 356. The test mode can comprise pulse trains, with each stimulus pulse comprising a doublet pulse (e.g., separated by a particular inter-pulse interval). For example, in some embodiments, the inter-pulse interval can be 5 ms, as described herein and shown in, for example, FIG. 6A. However, in other arrangements, the inter-pulse interval can be less than or greater than 5 ms, as desired or required (e.g., 0-5 ms, 5-10 ms, greater than 10 ms, etc.). The pulse trains can be applied to a targeted nerve to test the integrity and function of the connected muscle 358. The doublet pulses can be configured to increase (e.g., maximize) or otherwise enhance the torque time interval and reduce stimulus amplitude requirements.

In some embodiments, the pulses are output at a frequency of 10 Hz or lower to provide a tetanic like contraction. The frequency range may include 0.1-40 Hz (e.g., 0.1-0.2, 0.2-0.3, 0.3-0.4, 0.4-0.5, 0.5-1, 1-2, 2-3, 3-4, 4-5, 5-10, 10-15, 15-20, 20-30, 30-40 Hz, frequencies within the foregoing ranges, etc.).

In some embodiments, the amplitude of the stimulus can be configured to be adjusted 360 until a desired response is reached 362. If the user is satisfied with the testing of a targeted nerve, he/she can selectively choose to test other nerves 364, and the process of adjusting amplitudes can be repeated. In some embodiments, once the desired response for a nerve that was to be tested is reached, the user can be done using the system 366.

In some embodiments, with continued reference to FIG. 24, when a user is satisfied with locating nerves and/or when a determination is made that a nerve is injured 368 (e.g., the nerve is injured given a particular threshold level or response), the practitioner can connect an electrode (e.g., a cuff-type electrode, any other type of electrode, etc.) to a nerve port located on the housing 370. Any other type of electrode can be used, as desired or required. The system can be configured to detect the electrode 372 and appropriately direct the stimulus output from the probe to the electrode. When this occurs, the system mode can be switched to neuroregenerative treatment mode 374. The stimulus amplitude can be changed 376 until a desired response is reached 378. The user can then initiate treatment 380 of an injured nerve using neuroregenerative therapy. In some embodiments, the system comprises a timer that limits the duration of neuroregenerative therapy 382 and checks to ensure that the total time was not exceeded 384. In such embodiments, once the prescribed or required time requirement has been reached, the system can be configured to shut off 386 (e.g., automatically, according to a predetermined protocol or algorithm). Further, the system can be configured to provide the practitioner with an appropriate indication or cue (e.g., a visual cue, audio cue and/or any other indication).

In some embodiments, intraoperative use of the system can comprise hands-free usage (full or partial hands-free usage). For example, the system can operate in a mode so that it may be placed within the operative field and require minimal or reduced attention from operative staff during the period of stimulation. As previously discussed, the shape of the housing can be used to prevent the system from rolling off the operative table or sterile towels that are placed on a patient. Additionally, as also discussed herein, the inclusion of a specially-shaped (e.g., hook-shaped) extension element or other feature can assist the user to couple the system to an IV pole or other structure in relative proximity to the subject being treated. Advantageously, these features can permit and facilitate hands-free use with minimal or reduced intervention from operative staff. In some arrangements, the system is single use, and hence, once turned on or otherwise activated, the system can no longer be turned off. For example, in some arrangements, when the pull-tab is removed, engaging power the source, the device has a finite functional period dictated by the battery life. In some embodiments, the pull-tab may be replaced by an on/off switch or similar feature or component, thereby making the device reusable.

Peri-Operative Use

As noted herein and described in greater detail below, any system embodiments disclosed herein can be also be used in a peri-operative setting or application. For example, in some embodiments, a system in accordance with the various arrangements described herein can be configured to connect to a mono-polar electrode (e.g., serving as the active stimulating electrode or cathode). Such a monopolar electrode can comprise various forms including and without limitation, a needle electrode, a catheter or cylindrical type electrode and/or the like that may be placed close to an injured nerve percutaneously or be placed close to the nerve when the injured nerve is exposed. As disclosed herein, any other type of electrode can be incorporated into a device or system design or the execution of a treatment method.

In some embodiments, a monopolar lead is substituted as the nerve probe and a return electrode is connected to the nerve port. In some embodiments, a multi-conductor electrode lead is connected to the nerve port. One of the conductors of the system can connect to a monopolar lead placed within the patient while a second conductor may be connected to a return electrode such as a surface pad or needle. In some embodiments, the nerve probe is not present requiring only connection to the nerve port in order to output electrical stimulation pulses, as shown, for example, in FIG. 21A. Some embodiments of the system can be advantageous in certain indications and for certain uses, such as, for example, carpal tunnel release surgery.

In both use cases outlined above (e.g., both in the intra-operative and peri-operative contexts), the system is not necessarily limited to be used in the manner described for those use cases. For example, the peri-operative use case may also be applied intraoperatively if the end-user decides it more appropriate to stimulate using a monopolar electrode lead or similar lead.

Figure 25:
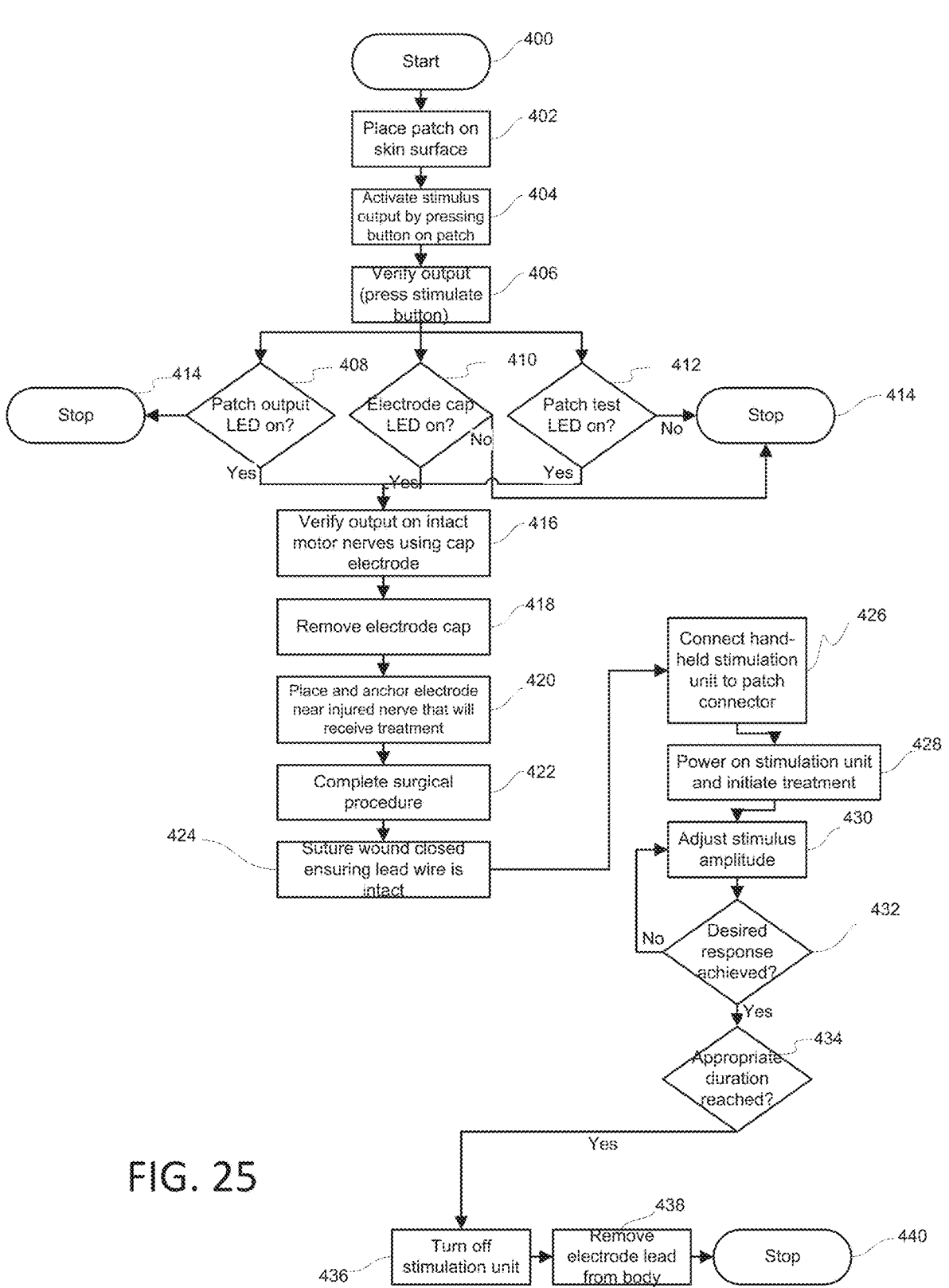
FIG. 25 is a flow diagram illustrating the process of locating and treating an injured nerve in an intraoperative setting using the systems and devices disclosed herein according to another embodiment.

FIG. 25 outlines a flow diagram of one embodiment of usage of a peri-operative system (e.g., such as a patch described herein). In one embodiment, a user places an adhesive patch 80 on the skin of a patient 402. The location of the patch is not specific, and in some embodiments, it is satisfactory as long as it is in at least partial physical contact with the skin of the patient or subject. In one embodiment, the built-in stimulus generator within the patch is activated by pressing a switch or other controller 404. The switch or other controller can be identical or similar to those described herein.

According to some embodiments, the output of the pulse generator comprises single pulses, pulse trains, doublet pulse trains or any other type of pulses. The pulses can be constant voltage or constant current pulses with amplitudes sufficient to depolarize a nerve or muscle provided the appropriate electrode contact and/or other operational parameters are used. In one arrangement, once the stimulus generator is activated, the user may want to verify the stimulus output 406. In some embodiments, such verification is accomplished in one or more steps, in accordance with one or more of the configurations described herein.

In some arrangements, the user may observe the stimulus output LED 82 on the patch itself 408 (and/or be alerted of stimulus output using another type of visual, audible, haptic and/or other indicator or output). If an electrode cap, similar to the embodiments described herein, is assembled with the electrode lead, the user can observe a LED (or other indicator) within the cap turn on when the stimulus is output 410.

According to some arrangements, where no cap is present, the user can touch the electrode lead to a conductive surface used for testing output on the patch itself 412, when connected a LED on the patch will turn on. In some arrangements, where no cap is present, and a cuff electrode apparatus 10 is used, the user may verify the stimulus output by touching the exposed contact on the verification bar within the cuff (if present) to a conductive surface used for testing output on the patch itself. In some arrangements, the cuff apparatus 10 may comprise multiple electrodes in a bipolar or multi-polar configuration. Verification of the stimulus output in this arrangement can include observing if the LED or other indicator of the verification bar is activated (e.g., turns on).

In some embodiments, if any or all of the described verification steps above are negative, the user can stop 414 the procedure and remove the patch as the stimulus generator or electrode lead may be defective. If, however, one or more of the tests are positive, the user can continue with the procedure. In one embodiment, for instance, during a surgical procedure with an open incision, the user can additionally verify the output by either using the larger conductive surface of a cap 416 or the conductive lead tip on to touch exposed intact and uninjured nerves or nearby muscles.

In some configurations, if the user is satisfied with the output and the cap is connected, the user can remove the cap 418 and place the lead adjacent (e.g., next to) an injured nerve that is to be treated with neuroregenerative therapy 420. In some embodiments, the user can complete the surgical procedure 422 and suture the wound closed while maintaining the exposed percutaneous lead 424 is exiting the wound appropriately.

According to some arrangements, a patient may then be removed from the operating room and a user, such as a nurse, can connect a second stimulation unit to the patch connector 426. The second stimulation unit can be turned on and initiates neuroregenerative therapy of the injured nerve 428. The user may adjust stimulus amplitudes throughout the course of the therapeutic time 430. If a desired response is achieved 432, and this may be based on patient feedback, muscle contractile response or other metrics, the user can, in some embodiments, leave the stimulation unit to complete the therapy. When the therapy has been completed 434, the stimulation unit is turned off 436, and the electrode lead is removed from the body 438 and the procedure can be completed 440.

In some embodiments, a first stimulation unit can provide both verification stimulus pulses used to test nerves, muscles, and/or verify functionality of the electrode and/or system and also contain necessary hardware to provide neuroregenerative therapy without requirement of a second stimulation unit.

Figure 26:
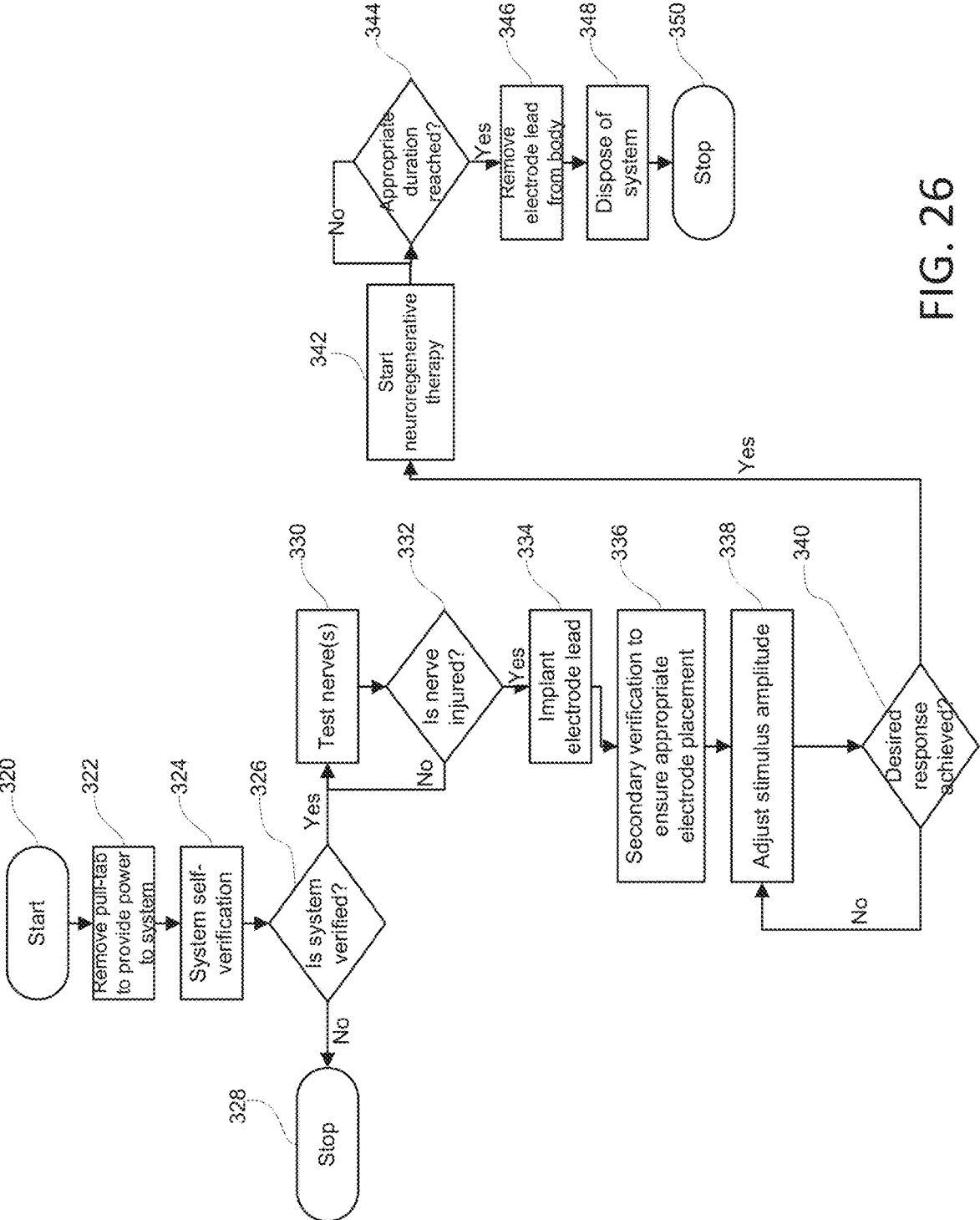
FIG. 26 is a flow diagram illustrating the process of locating and treating an injured nerve using the systems and devices disclosed herein according to another embodiment.

A flow chart of the functionality of such a system is provided in FIG. 26. As illustrated in the example embodiment of FIG. 26, when power is applied to the system, e.g., via removal of a pull-tab 322, the system can be configured to operate in a self-verification state 324. Self-verification can include touching an electrode to an exposed contact on the system housing or placing the lead within the system housing, as described herein. In some embodiments, self-verification comprises placing the electrode on an exposed or recessed contact with a stimulation source providing a characteristic frequency pattern used to "unlock" the system. In some arrangements, when the system has completed self-verification 326, it can be used to locate (e.g., "test") nerves 330. In some arrangements, an accessory or component of the device or system, e.g., such as a cap or hand-held attachment, may be clipped or otherwise attached (e.g., directly or indirectly) to the electrode lead to facilitate grasping and usage as a hand-held nerve locator.

With continued reference to FIG. 26, an injured nerve is located 332, either using the system itself or is determined apriori by a user (e.g., practitioner, medical professional, through some other mechanism or protocol, etc.), the electrode lead may be temporarily implanted 334 using an insertion tool (e.g., in accordance with embodiments disclosed herein). The method of implantation can rely, at least in part, on using tissue (e.g., preferably non-dissect or non-undermined tissue) in the para-incision area to support the anchoring of the lead and reduce or minimize lead movement in the lateral direction (e.g., perpendicular to the longitudinal axis of the lead). Once implanted, the stimulation amplitude and/or stimulation energy delivered can be adjusted, and a secondary verification 336 can take place to ensure adequate electrode placement. This verification step may comprise of measuring current flow between anode and cathode electrodes, measuring action potentials in a nerve, measuring motor or sensory responses and/or any other verification step or method, as desired or required. The stimulus parameters used for this secondary verification step may comprise a repetitive burst sequence with at least two pulses. In some embodiments, the repetitive burst sequence comprises at least three pulses (e.g., 3, 4, 5, more than 5, etc.). When a desired response to the verification has occurred 340, neuroregenerative therapy may commence on the injured nerve 342. The system can be configured to provide neuroregenerative treatment to injured nerves for the appropriate amount of time, as disclosed herein. When such time has elapsed 344, the electrode may be removed from the body 346, and both the electrode and stimulation source may be disposed of 348.

Multiple Nerve Injuries

In cases such as brachial plexus injuries, where multiple nerves are injured, it may be desirable to provide neuroregenerative therapy to all injured nerves at once. In such instances and arrangements, the system can be designed and configured to output to different electrode configurations. See, for example, FIG. 27.

Figure 27:
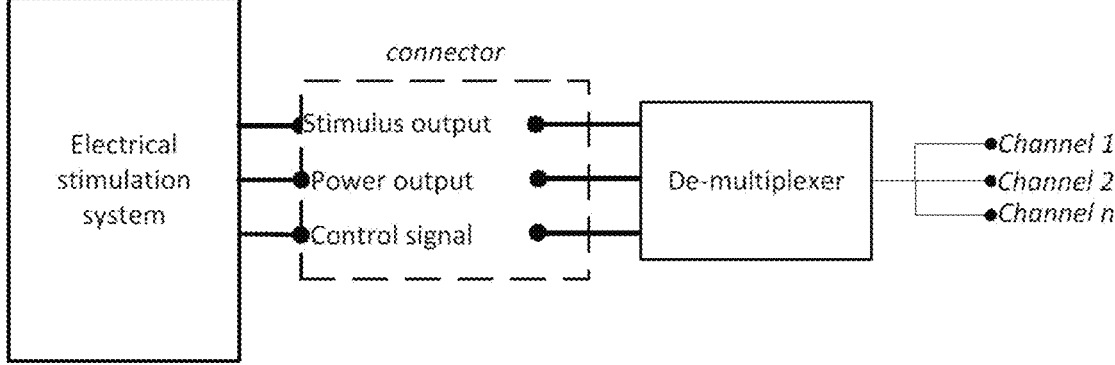
FIG. 27 illustrates a schematic view of how a multichannel electrode may be interfaced with the system according to one embodiment.

In some embodiments, as illustrated in the example of FIG. 27, an electrode apparatus connector 208 with an analog demultiplexer 210 controlled by the system can be connected to the nerve port. In some arrangements, this permits the system to provide output to one channel at a time by switching between channels 212.

In some embodiments, the nerve port comprises additional conductive signal paths or lines for carrying power and control information to the analog demultiplexer. In some embodiments, the connector may feature connections to control an analog demultiplexer using either a parallel configuration where one control signal line is needed for each electrode connected to the system (e.g. ON Semi MC14067B, Analog Devices ADG5412, Maxim Integrated MAX4623, or equivalent). In other arrangements, the connector can include three control signals for interfacing to an analog demultiplexer using the serial peripheral interface (SPI) (e.g. Analog Devices ADGS1412).

According to some embodiments, a cable containing the multiple electrodes can comprise a connector housing unit that include the demultiplexer circuit and indicators, such as, for example, LEDs displaying the active channel. In yet other arrangements, the connector housing unit can include memory and an energy source (e.g., a relatively small energy source, such as, for example, such as a coin cell battery or the like) to power said memory. In some arrangements, the memory is configured to store information, for example, stimulus settings, other operational parameter and/or the like. In some arrangements, the connector housing unit can include memory, energy source, demultiplexer circuitry and/or any other features or components, as desired or required. Each lead wire connected to an electrode apparatus can include a connector housing unit that comprises one or more of the components described in greater detail with reference to any of the embodiments disclosed herein.

Treatment Method Duration

In terms of therapeutic time duration, studies have demonstrated the optimal duration to be as little as 30 minutes. However, most studies utilize a treatment duration of or near 1 hour. The duration of a treatment method can therefore be between 10 and 90 minutes (e.g., 10-20, 20-30, 30-40, 40-50, 50-60, 60-70, 70-80, 80-90, 10-30, 30-60, 40-80 minutes, times within the foregoing ranges, etc.), as desired or required. In other embodiments, a treatment procedure can take longer than 90 minutes or less than 10 minutes.

In some embodiments, the treatment of injured nerves comprises the set-up of an appropriate electrode apparatus and stimulus parameters, the initiation of treatment, and the maintenance of a stimulus amplitude sufficient to depolarize axons. Furthermore, the treatment duration need not be applied continuously for the entire treatment duration so long as a total time of treatment is equivalent to the optimal stimulation duration. For example, if the electrode apparatus needs to be moved during a surgical procedure, the end-user has the ability to pause the treatment using a user-operable control as outlined previously. When paused, the system will stop delivering electrical stimulus output and only resume when the pause control is used again. In this specific example, once treatment has been applied for 1 hour, the previously described indicators may notify the user of treatment completion.

In some arrangements, it may be advantageous to deliver multiple bouts of brief electrical stimulation with each bout comprising of the previously described durations (e.g., 10 to 90 minutes) and stimulus parameters. The timing between subsequent bouts of brief electrical stimulation, or rest periods, may vary from multiple bouts per day to a single bout separated by one or more days and delivered on one or more days. In some embodiments, a single bout of brief electrical stimulation of injured axons transiently upregulates regeneration associated genes and neurotrophic factors in the cell bodies of the injured axons. It is the intention, according to some embodiments, that multiple bouts may prolong, transiently increase, or maintain the upregulated expression of these genes and neurotrophic factors.

The number of bouts to be delivered may vary depending on the distance of type of nerve injury. By way of example, a proximal injury in the shoulder may require a minimum of 450 days for injured axons to regenerate from the site of injury to distal muscle in the hand. In a scenario where daily stimulation is provided, delivering multiple bouts of stimulation would require at least 450 bouts in this scenario. Injuries more distal, such a laceration of the digital nerve in the human finger, may require considerably less bouts, for instance 30-60, in the case of daily stimulation. The number of bouts delivered is injury dependent and cannot be determined apriori. In some cases, only a few bouts are needed as repeated bouts may not be beneficial. The primary effect of stimulation is to enhance nerve outgrowth across an injury site and thus after a certain number of days all injured axons have crossed the injury site and may not benefit from further neuroregenerative treatment.

In some embodiments, implementation of multiple bouts of brief electrical stimulation may require modification of the previously described systems and devices. In one example, a second stimulation system that interfaces with the connector 186 on the adhesive patch 80 may be programmed to monitor, track, or verify if appropriate treatment duration and number of treatments have been performed. In some embodiments, the second stimulation system may save patient information, such as a unique identifier, in order to track patient compliance with the treatment.

In another example, the adhesive patch 80 can be configured with an energy source to last for the duration of delivery of multiple bouts. In such an embodiment, the adhesive patch 80 may comprise of elements allowing it to function as both a validation energy source and stimulation energy source. Additional elements that may be included in the adhesive patch are an indicator or user controls for adjusting stimulus parameters as mentioned herein.

In some embodiments, the adhesive patch includes circuit elements used for wireless communication with an external device or implanted device or a combination thereof. In one example arrangement, such device may include a smart phone or other computing device (e.g., tablet). In such an application, said smart phone may include a software application used to change stimulation parameters and verify appropriate treatment duration and application. In another example, such device may include an implanted electrode lead. In such an application, the electrode lead may include hardware and circuitry to communicate with patch and perform desired functions, like electrical stimulation.

Although several embodiments and examples are disclosed herein, the present application extends beyond the specifically disclosed embodiments to other alternative embodiments and/or uses of the various inventions and modifications, and/or equivalents thereof. It is also contemplated that various combinations or subcombinations of the specific features and aspects of the embodiments may be made and still fall within the scope of the inventions. Accordingly, various features and aspects of the disclosed embodiments can be combined with or substituted for one another in order to form varying modes of the disclosed inventions. Thus, the scope of the various inventions disclosed herein should not be limited by any particular embodiments described above. While the embodiments disclosed herein are susceptible to various modifications, and alternative forms, specific examples thereof have been shown in the drawings and are described in detail herein. However, the inventions of the present application are not limited to the particular forms or methods disclosed, but, to the contrary, cover all modifications, equivalents, and alternatives falling within the spirit and scope of the various embodiments described and the appended claims. Further, the disclosure herein of any particular feature, aspect, method, property, characteristic, quality, attribute, element and/or the like in connection with an implementation or embodiment can be used in all other implementations or embodiments set forth herein.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, any structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

The methods disclosed herein include certain actions taken by a practitioner; however, they can also include any third-party instruction of those actions, either expressly or by implication. For example, actions such as "locating" a nerve, "coupling" an electrode to a nerve, "initiating" a stimulation procedure include "instructing locating," "instructing coupling," and "instructing initiating" etc., respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially rigid" includes "rigid," and "substantially parallel" includes "parallel."

What is claimed is:

1. A method of stimulating a target nerve in a subject, comprising:

positioning at least one electrode assembly of a stimulation device adjacent the target nerve, wherein the at least one electrode is located along an electrode lead of the stimulation device;

wherein the at least one electrode assembly is positioned adjacent the target nerve percutaneously;

delivering stimulation energy to the target nerve of the subject having a first frequency via the at least one electrode to confirm at least one validation condition;

delivering stimulation energy to the target nerve of the subject having a second frequency via the at least one electrode assembly, wherein delivering stimulation energy to the subject to create a regenerative effect to the target nerve;

wherein stimulation energy to confirm at least one validation condition and to create a regenerative effect to the target nerve is provided by the same at least one electrode; and wherein the at least one electrode assembly is configured to be percutaneously removed from the subject through a percutaneous access point following the delivery of stimulation energy; and removing the at least one electrode assembly from the subject.

2. The method of claim 1, wherein the second frequency is 1 Hz to 100 Hz;

wherein the target nerve comprises a peripheral nerve; and wherein the stimulation device is configured to be removably secured to a skin surface of the subject using an adhesive patch.

3. The method of claim 1, wherein the second frequency is 1 Hz to 100 Hz.

4. The method of claim 1, wherein the second frequency is 10 Hz to 100 Hz.

5. The method of claim 1, wherein the at least one electrode assembly comprises a bipolar electrode assembly.

6. The method of claim 1, wherein delivering stimulation energy occurs intraoperatively.

7. The method of claim 1, wherein delivering stimulation energy occurs postoperatively.

8. The method of claim 1, wherein delivering stimulation energy to create a regenerative effect occurs for a particular time period.

9. The method of claim 8, wherein the particular time period is 10 to 90 minutes.

10. The method of claim 1, wherein positioning the at least one electrode assembly adjacent the target nerve is performed with assistance of an insertion tool.

11. The method of claim 1, wherein the stimulation device is configured to be removably secured to a skin surface of the subject using an adhesive patch.

12. The method of claim 1, further comprising modifying at least one operational parameter of the stimulation energy using at least one controller of the stimulation device.

13. The method of claim 1, wherein the target nerve comprises a peripheral nerve.

14. A method of stimulating a target nerve in a subject, comprising:

positioning at least one electrode assembly adjacent the target nerve;

wherein the at least one electrode assembly is positioned adjacent the target nerve percutaneously; and delivering stimulation energy to the target nerve of the subject to confirm at least one validation condition;

delivering stimulation energy to the target nerve of the subject via the at least one electrode assembly, wherein delivering stimulation energy to the subject creates a regenerative effect to the target nerve;

wherein the at least one electrode assembly is configured to be percutaneously removed from the subject through a percutaneous access point following the delivery of stimulation energy; and removing the at least one electrode assembly from the subject.

15. The method of claim 14, wherein delivering stimulation energy occurs intraoperatively.

16. The method of claim 14, wherein delivering stimulation energy occurs postoperatively.

17. The method of claim 14, wherein the at least one electrode assembly comprises a bipolar electrode assembly.

18. The method of claim 14, wherein the stimulation device is configured to be removably secured to a skin surface of the subject using an adhesive patch.

* * * * *